United States Patent
Thanos et al.

(10) Patent No.: US 10,450,353 B2
(45) Date of Patent: *Oct. 22, 2019

(54) PROTEOLYTIC INACTIVATION OF SELECT PROTEINS IN BACTERIAL EXTRACTS FOR IMPROVED EXPRESSION

(71) Applicant: Sutro Biopharma, Inc., South San Francisco, CA (US)

(72) Inventors: Christopher D. Thanos, Tiburon, CA (US); Christopher J. Murray, Soquel, CA (US); Junhao Yang, Palo Alto, CA (US); Heather Stephenson, San Jose, CA (US)

(73) Assignee: Sutro Biopharma, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/483,766

(22) Filed: Apr. 10, 2017

(65) Prior Publication Data

US 2017/0283469 A1     Oct. 5, 2017

Related U.S. Application Data

(63) Continuation of application No. 14/434,391, filed as application No. PCT/US2013/063804 on Oct. 8, 2013, now Pat. No. 9,650,621.

(60) Provisional application No. 61/713,245, filed on Oct. 12, 2012.

(51) Int. Cl.
| | |
|---|---|
| C07K 14/00 | (2006.01) |
| C07K 14/245 | (2006.01) |
| C12P 21/06 | (2006.01) |
| C12N 1/21 | (2006.01) |
| C12N 15/00 | (2006.01) |
| C12P 21/00 | (2006.01) |
| C07K 16/00 | (2006.01) |
| C12P 21/02 | (2006.01) |
| C07K 16/06 | (2006.01) |
| C07K 16/32 | (2006.01) |
| C12N 9/52 | (2006.01) |
| C12Q 1/686 | (2018.01) |
| C12Q 1/689 | (2018.01) |
| G01N 30/02 | (2006.01) |
| G01N 30/06 | (2006.01) |

(52) U.S. Cl.
CPC ............ *C07K 14/245* (2013.01); *C07K 16/00* (2013.01); *C07K 16/065* (2013.01); *C07K 16/32* (2013.01); *C12N 9/52* (2013.01); *C12P 21/00* (2013.01); *C12P 21/02* (2013.01); *C12Q 1/686* (2013.01); *C12Q 1/689* (2013.01); *G01N 30/02* (2013.01); *G01N 30/06* (2013.01); *C07K 2319/50* (2013.01); *C12Y 304/00* (2013.01); *C12Y 304/21* (2013.01)

(58) Field of Classification Search
None
See application file for complete search history.

(56) References Cited

U.S. PATENT DOCUMENTS

| | | | |
|---|---|---|---|
| 7,338,789 B2 * | 3/2008 | Swartz | .................. C12P 21/02 |
| | | | 435/71.2 |
| 7,344,856 B1 | 3/2008 | Okuno et al. | |
| 9,650,621 B2 * | 5/2017 | Thanos | ................ C07K 16/065 |
| 9,657,323 B2 | 5/2017 | Okuno et al. | |
| 2009/0087879 A1 | 4/2009 | Gerrits et al. | |
| 2015/0259664 A1 | 9/2015 | Thanos et al. | |

FOREIGN PATENT DOCUMENTS

| | | |
|---|---|---|
| KR | 20080069993 A | 7/2008 |
| KR | 20080113226 A | 12/2008 |
| WO | 2006082059 A1 | 8/2006 |
| WO | 2005/030956 A1 | 12/2006 |
| WO | 2007047301 A2 | 4/2007 |
| WO | 2007047301 A3 | 4/2007 |
| WO | 2007109035 A2 | 9/2007 |
| WO | 2007109035 A3 | 9/2007 |

OTHER PUBLICATIONS

UniProt Database Accession No. A7ZKY5, Oct. 2011, 2 pages (Year: 2011).*
Yin et al., "RF1 attenuation enables efficient non-natural amino acid incorporation for production of homogeneous antibody drug conjugates", Scientific Reports 7:3026, 2017, 13 pages (Year: 2017).*
Flowers, C.A., "Engineering and Analysis of Protease Fine Specificity via Site-Directed Mutagenesis," Thesis, University of Texas at Austin, 2013.
Korostelev et al., "Recognition of the amber UAG stop codon by release factor RF1", EMBO J. vol. 29, No. 15, Aug. 4, 2010, pp. 2577-2585.
McCarter et al., "Substrate Specificity of the *Escherichia coli* Outer Membrane Protease OmpT", J. of Bacteriology, American Society for Microbiology. Washington, DC; US, vol. 186, No. 17., Sep. 1, 2004, pp. 5919-5925.

(Continued)

*Primary Examiner* — David Steadman
(74) *Attorney, Agent, or Firm* — Kilpatrick Townsend & Stockton LLP

(57) ABSTRACT

The present disclosure provides modified proteins that are capable of being cleaved by the protease OmpT1. The proteins can be modified in an exposed surface motif to incorporate OmpT1 cleavage sites. Also provided are nucleic acids encoding the modified proteins, bacterial cells that express the modified proteins, and cell free synthesis systems containing modified RF1. The disclosure further provides methods for reducing the deleterious activity of a modified protein in a cell free synthesis system by contacting the modified protein with OmpT1. Also provided are methods for reducing RF1 competition at an amber codon in the cell free synthesis system, and methods for expressing a protein in the cell free synthesis system. The modified proteins of the invention can be used to increase the yield of proteins having non-natural amino acids incorporated at an amber codon.

13 Claims, 3 Drawing Sheets

Specification includes a Sequence Listing.

(56) References Cited

OTHER PUBLICATIONS

Okuno et al., "Utilization of *Escherichia coli* Outer-Membrane Endoprotease OmpT Variants as Processing Enzymes for Production of Peptides from Designer Fusion Proteins", Appl. Environ. Microbiol. vol. 70, No. 1, Jan. 2004, pp. 76-86.
PCT/US2013/063804, International Search Report and Written Opinion, dated Dec. 10, 2013, 15 pages.
PCT/US2013/063804, "Written Opinion", dated Sep. 30, 2014, 8 pages.
SG11201502875V, "Written Opinion", dated Feb. 16, 2016, 9 pages.
Diago-Navarro et al., "Novel *Eschericia coil* RF1 mutants with decreased translation termination activity and increased sensitivity to the cytotoxic effect of the bacterial toxins Kid and RelE," Molecular Microbiology (2009) 71(1):66-78.
Short et al., "Effects of Release Factor 1 on in Vitro Protein Translation and the Elaboration of Proteins Containing Unnatural Amino Acids," Biochemistry (1999) 38:8808-8819.
KR10-2015-7012291, "Notice of Decision to Grant", dated May 30, 2019, 3 pages.

\* cited by examiner

PROTEOLYTIC INACTIVATION OF SELECT PROTEINS IN BACTERIAL EXTRACTS FOR IMPROVED EXPRESSION

CROSS-REFERENCES TO RELATED APPLICATIONS

The present patent application is a Continuation of U.S. application Ser. No. 14/434,391, filed Apr. 8, 2015, now U.S. Pat. No. 9,650,621, which is a U.S. National Phase application under 35 U.S.C. 371 of Application No. PCT/US13/63804, filed Oct. 8, 2013, which claims benefit of priority to U.S. Provisional Application No. 61/713,245, filed Oct. 12, 2012, which is incorporated by reference herein in its entirety.

REFERENCE TO SEQUENCE LISTING

This application includes a Sequence Listing as a text file named "091200-1043302-005620US_SEQ.txt" created May 4, 2017, and containing 60,908 bytes. The material contained in this text file is incorporated by reference in its entirety for all purposes.

FIELD OF THE INVENTION

The invention relates to cell free synthesis technology, and particularly to the proteolytic inactivation of select proteins in a bacterial extract. A preferred use is to increase the yield of polypeptides having a non-native amino acid incorporated at a defined amino acid residue.

BACKGROUND OF THE INVENTION

The use of bacterial cell-free extracts for in vitro protein synthesis offers several advantages over conventional in vivo protein expression methods. Cell-free systems can direct most, if not all, of the metabolic resources of the cell towards the exclusive production of one protein. Moreover, the lack of a cell wall and membrane components in vitro is advantageous since it allows for control of the synthesis environment. However, the efficiency of cell-free extracts can be decreased by bacterial proteins that inhibit protein synthesis, either directly or indirectly. Thus, inactivation of undesirable proteins that decrease the efficiency of protein synthesis should increase the yield of desirable proteins in cell-free extracts. For example, the inactivation of proteins that decrease the efficiency of protein synthesis should increase the yield of polypeptides having non-native amino acids incorporated at a defined amino acid residue. The introduction of non-native amino acids (nnAA) into polypeptides is useful for increasing the biological diversity and function of proteins. One approach for producing polypeptides having a nnAA incorporated at a defined amino acid residue is to use an nnAA, aminoacylated orthogonal CUA containing tRNA for introduction of the nnAA into the nascent polypeptide at an amber (stop) codon during protein translation. However, the incorporation of nnAA at an amber codon can be inhibited by the native bacterial termination complex, which normally recognizes the stop codon and terminates translation. Release Factor 1 (RF1) is a termination complex protein that facilitates the termination of translation by recognizing the amber codon in an mRNA sequence. RF1 recognition of the amber stop codon can promote pre-mature truncation products at the site of non-native amino acid incorporation, and thus decreased protein yield. Therefore, attenuating the activity of RF1 may increase nnAA incorporation into recombinant proteins.

It has previously been shown that nnAA incorporation can be increased by attenuating RF1 activity in 3 ways: 1) neutralizing antibody inactivation of RF1, 2) genomic knockout of RF1 (in an RF2 bolstered strain), and 3) site specific removal of RF1 using a strain engineered to express RF1 containing a protein tag for removal by affinity chromatography (Chitin Binding Domain and His Tag). The present disclosure describes a novel method for inactivating RF1 by introducing proteolytic cleavage sites into the RF1 amino acid sequence. The cleavage sites are not accessible to the protease during bacterial cell growth, but are cleaved by the protease when the bacterial cells are lysed to produce cell-free extract. Thus, the yield of full length polypeptides having a nnAA incorporated at an amber codon is increased in bacterial cell extracts expressing modified RF1 variants described herein.

BRIEF SUMMARY OF THE INVENTION

The present invention provides recombinant target proteins that are modified to comprise an Outer Membrane Protein T1 (OmpT1) protease cleavage site. The OmpT1 cleavage site includes a scissile OmpT1 peptide bond. In some embodiments, the target protein is modified to introduce the OmpT1 cleavage site into a surface exposed motif of the target protein. Because OmpT1 cleaves substrates between dibasic residues with high efficiency, the native surface exposed motif is modified to include two adjacent basic amino acids that are positively charged at pH 7.0. The target protein can be an essential protein that is required, for example, for normal cell growth and/or survival.

In some embodiments, the surface exposed motif has a B factor of at least 50 $Å^2$ when the motif region of the protein is uncomplexed. In some embodiments, surface exposed motif has a total solvent accessible surface area of between about 25 $Å^2$ and about 225 $Å^2$. In some embodiments, the target protein is modified such that the scissile OmpT1 peptide bond is located in a position of the protein which exhibits a Phi angle of from 0° to −180° or a Psi angle from 0° to +180° in a Ramachadran Plot.

In one aspect, the invention provides a bacterial cell expressing both OmpT1 and an essential target protein recombinantly modified to include a scissile OmpT1 peptide bond. In some embodiments, the scissile OmpT1 peptide bond is located within a surface exposed motif and the native motif is modified to include two adjacent basic amino acids that are positively charged at pH 7.0. In some embodiments, the bacterial cell expresses an essential target protein recombinantly modified to include a scissile OmpT1 peptide bond where the bond is in a position of the protein which is located within a surface exposed motif having a B factor of at least 50 $Å^2$ when the protein is uncomplexed. In some embodiments, the bacterial cell expresses an essential target protein recombinantly modified to include a scissile OmpT1 peptide bond where the bond is in a position of the protein which is located within a surface exposed motif having a total solvent accessible surface area of between about 25 $Å^2$ and about 225 $Å^2$. In one embodiment, the bacterial cell expresses an essential target protein recombinantly modified to include a scissile OmpT1 peptide bond where the bond is in a position of the protein which exhibits a Phi angle of from 0° to −180° or a Psi angle from 0° to +180° in a Ramachadran Plot. In one embodiment, the bacterial cell is an *E. coli*.

In some embodiments, the essential target protein is selected from RF1, RF2, RNAse, thioredoxin reductase, glutarodoxin reductase, glutathione reductase, amino acid degrading enzymes, polyphosphate kinase, or cold shock proteins.

In a second aspect, the invention provides a method for reducing the deleterious activity of a modified essential target protein in an in vitro cell free synthesis system, the method comprising the steps of:
i) culturing an OmpT1 positive bacteria expressing the modified essential target protein said protein modified to include a scissile OmptT1 peptide bond where the protein is modified to include two adjacent basic amino acids that are positively charged at pH 7.0;
ii) lysing the bacteria to create a cell free synthesis extract;
iii) contacting the essential target protein with OmpT1 in an amount sufficient to reduce intact protein by 50%;
iv) adding a nucleic acid template to the extract where the template codes for a protein of interest; and,
v) allowing the cell free synthesis system to produce the protein of interest.

In some embodiments of the method, the scissile OmptT1 peptide bond is located within a surface exposed motif having a B factor of at least 50 Å$^2$ when the protein is uncomplexed. In some embodiments, the scissile OmpT1 peptide bond is located within a surface exposed motif having a total solvent accessible surface area of between about 25 Å$^2$ and about 225 Å$^2$. In some embodiments, the scissile OmpT1 peptide bond is located in a position of the protein which exhibits a Phi angle of from 0° to −180° or a Psi angle from 0° to +180° in a Ramachadran Plot.

In some embodiments of the method, the oxidative phosphorylation system of the bacteria remains active after cell lysis and during the synthesis of the protein of interest. In one embodiment, the cell free synthesis system places a non-native amino acid at an amber codon of the protein of interest.

In a third aspect, the invention provides a functional Releasing Factor 1 protein (RF1) that is cleavable by an Outer Membrane Protein T1 (OmpT1), where a scissile OmpT1 peptide bond is located within the switch loop region corresponding to amino acids 287-304 of wild type RF1 (SEQ ID NO:1) and where the switch loop region is modified to include two adjacent basic amino acids that are positively charged at pH 7.0. In some embodiments, the two adjacent basic amino acids are independently selected from arginine and lysine. In other embodiments, the switch loop region is modified to have three adjacent basic amino acids. In some embodiments, the native asparagine at position 296 is substituted for one of the three adjacent basic amino acids. The functional, modified RF1 protein is cleaved by OmpT1 at a faster rate than the wild-type RF1. For example, in one embodiment, the cleavage activity of modified RF1 by OmpT1 is greater than 50% of the wild type RF1 (SEQ ID NO:1) after 30 minutes at 30° C. when the modified and wild-type proteins are present at a similar concentration in a cell-free extract from bacteria expressing OmpT1.

In some embodiments, the functional RF1 that is cleavable by OmpT1 contains an OmpT1 cleavage peptide in the switch loop region.

In a fourth aspect, the invention provides a nucleic acid encoding a functional Releasing Factor 1 protein (RF1) that is cleavable by an Outer Membrane Protein T1 (OmpT1) where a scissile OmpT1 peptide bond is located within the switch loop region of RF1 corresponding to amino acids 287-304 of wild type RF1 (SEQ ID NO:1) and where the switch loop region is modified to include two adjacent basic amino acids that are positively charged at pH 7.0.

In a fifth aspect, the invention provides a method for reducing RF1 competition at an amber codon in an in vitro cell free synthesis system, the method comprising the steps of:
i) culturing an OmpT1 positive bacteria expressing a functional Releasing Factor 1 protein (RF1) that is cleavable by an Outer Membrane Protein T1 (OmpT1)
ii) lysing the bacteria to create a cell free synthesis extract;
iii) contacting the RF1 protein in the extract with OmpT1 in an amount to sufficient to reduce intact RF1 protein by 50%;
iv) adding a nucleic acid template to the extract where the template codes for a protein of interest and includes an amber codon; and,
v) allowing the cell free synthesis system to produce the protein of interest,
where the RF1 protein has a scissile OmpT1 peptide bond is located within the switch loop region corresponding to amino acids 287-304 of wild type RF1 (SEQ ID NO:1) and where the switch loop region is modified to include two adjacent basic amino acids that are positively charged at pH 7.0.

In one embodiment of the method, the OmpT1 positive bacteria is from *E. coli*. In some embodiments, the oxidative phosphorylation system of the bacteria remains active after cell lysis and during the synthesis of the protein of interest. In other embodiments, the cell free synthesis system places a non-native amino acid at the amber codon of the protein of interest.

In another aspect, the invention provides a cell free synthesis system comprising, in a single reaction mixture:
i) components from a bacterial lysate sufficient to translate a nucleic acid template encoding a protein;
ii) a nucleic acid template encoding a protein of interest and having at least one amber codon;
iii) tRNA complementary to the amber codon; and,
iv) a functional Releasing Factor 1 (RF1) protein cleavable by an Outer Membrane Protein T1 (OmpT1), where a scissile OmpT1 peptide bond is located within the switch loop region of RF1 corresponding to amino acids 287-304 of wild type RF1 (SEQ ID NO:1) and where the switch loop region is modified to include two adjacent basic amino acids that are positively charged at pH 7.0.

In some embodiments, the cell free synthesis system reaction mixture further comprises a non-natural amino acid and corresponding amino acid synthetase, the synthetase able to charge the tRNA complimentary to the amber codon with the non-natural amino acid. In some embodiments, the cell free synthesis system generates ATP via an active oxidative phosphorylation system.

In yet another aspect, the invention provides a method for expressing protein in a cell-free synthesis system, comprising:
i. combining a nucleic acid template with a bacterial extract comprising an RF1 protein that has been cleaved by OmpT1 at a scissile OmpT1 peptide bond located within the switch loop region corresponding to amino acids 287-303 of wild type RF1 (SEQ ID NO:1) and where the switch loop region has been modified to include two adjacent basic amino acids that are positively charged at pH 7.0 under conditions that permit protein synthesis; and
ii. expressing a protein from the nucleic acid template.

In another aspect, the invention provides a bacterial cell comprising a genomically integrated sequence coding for a functional RF1 that is cleavable by OmpT1.

BRIEF DESCRIPTION OF THE DRAWINGS

FIG. 1 shows that modified RF1 protein variants containing OmpT cleavage sites have wild-type RF1 activity when added to cell-free extracts lacking OmpT activity. The ability of exogenous RF-1 variants to reduce suppression (increase chain termination) when adding a non-native amino acid at an amber codon introduced at position S378 of the Fc protein (Fc_S378TAG) was determined.

DEFINITIONS

Figures 1A, 1B:
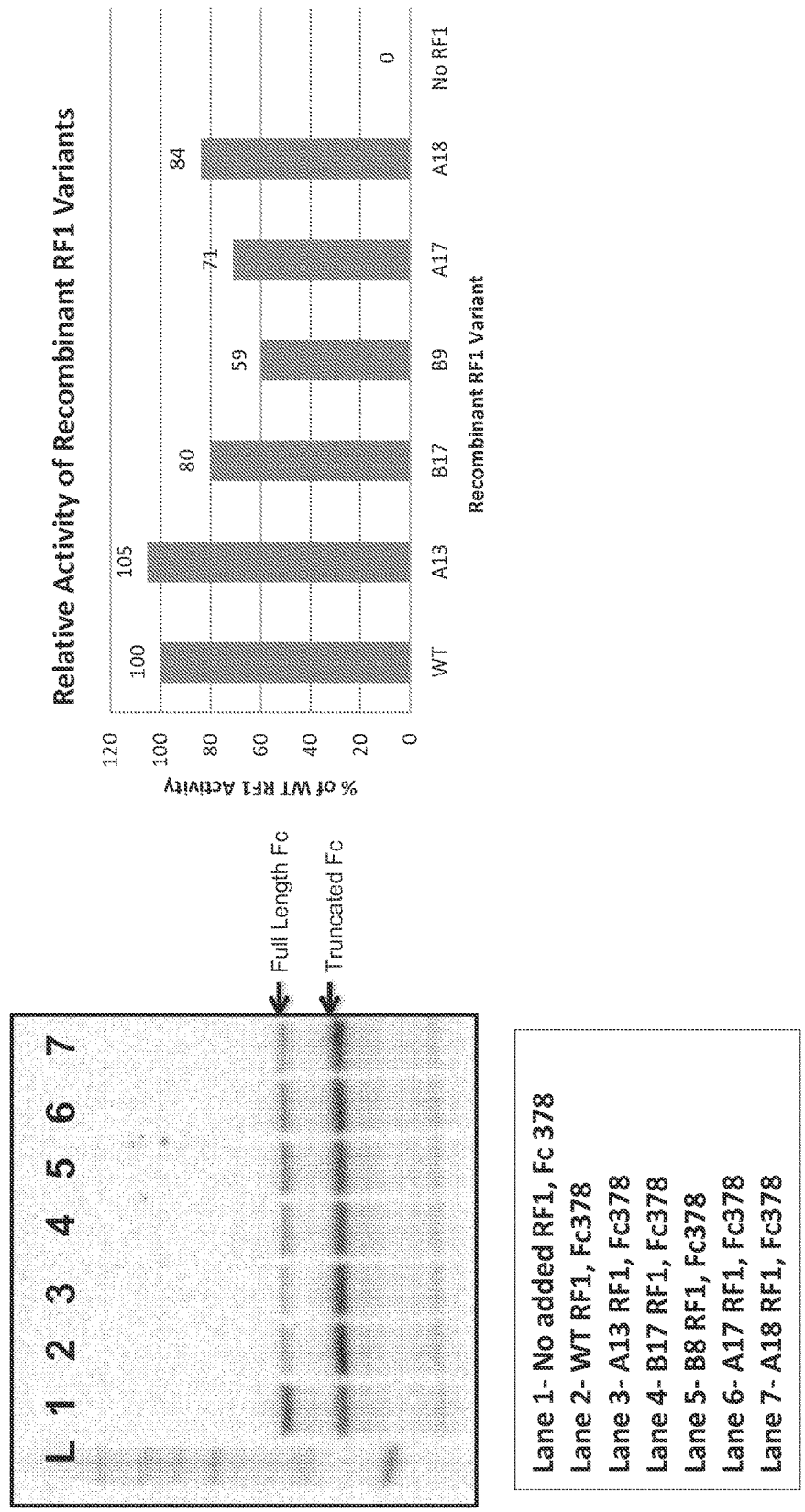
FIG. 1(A) Lane 1 is a control extract with no exogenously added RF1. The extract contains wild-type RF1, which results in reduced amber suppression, producing a truncated Fc (lower band in gel). Lane 2 is a control extract containing exogenously added wild-type (WT) RF1. The addition of wild-type RF1 results in a further reduction in amber suppression, which produces relatively more truncated Fc. Lanes 3-7 show cell-free extracts containing different RF1 variants of the invention. All five variants possess RF1 activity.
FIG. 1(B) shows the relative activity of RF1 variants, where added WT RF1 activity is set at 100 percent, and no added RF1 is set at zero percent.

"Aminoacylation" or "aminoacylate" refers to the complete process in which a tRNA is "charged" with its correct amino acid that is a result of adding an aminoacyl group to a compound. As it pertains to this invention, a tRNA that undergoes aminoacylation or has been aminoacylated is one that has been charged with an amino acid, and an amino acid that undergoes aminoacylation or has been aminoacylated is one that has been charged to a tRNA molecule.

"Aminoacyl-tRNA synthetase" or "tRNA synthetase" or "synthetase" or "aaRS" or "RS" refers to an enzyme that catalyzes a covalent linkage between an amino acid and a tRNA molecule. This results in a "charged" tRNA molecule, which is a tRNA molecule that has its respective amino acid attached via an ester bond.

"Codon" refers to a group of 3 consecutive nucleotides in a nucleic acid template that specify a particular naturally occurring amino acid, non-native amino acid, or translation stop (polypeptide chain termination) signal. Due to the degeneracy of the genetic code, an amino acid can be specified by more than one codon.

An amber codon is a polypeptide chain-termination sequence (UAG) in RNA (TAG in DNA) that acts to terminate polypeptide translation in most organisms. The amber codon can also encode the proteinogenic amino acid pyrrolysine if the appropriate tRNA is charged by its cognate aminoacyl-tRNA synthetase.

"Amber codon tRNA" or "amber suppressor tRNA" or "amber anti-codon tRNA" refers to a tRNA that binds to an amber codon.

"Adjacent amino acids" refers to amino acids that immediately precede or follow each other in the amino acid sequence of a polypeptide. For example, the amino acid at position two of a polypeptide's primary amino acid sequence is adjacent to amino acids at positions one and three. "Two adjacent basic amino acids" refers to one basic amino acid that immediately precedes or follows another basic amino acid in the primary amino acid sequence of a polypeptide. For example, the basic amino acid Arg (R) at position 295 of the RF1 amino acid sequence can be adjacent to a basic amino acid such as K or R introduced at position 296 of the RF1 amino acid sequence.

"Bacterial derived cell free extract" refers to preparation of in vitro reaction mixtures able to translate mRNA into polypeptides. The mixtures include ribosomes, ATP, amino acids, and tRNAs. They may be derived directly from lysed bacteria, from purified components or combinations of both.

"Basic amino acids" are polar and positively charged at pH values below their $pK_a$'s, and are very hydrophilic. Examples of basic amino acids at neutral pH include Arginine (Arg=R), Lysine (Lys=K), and Histidine (His=H).

"Cell-free synthesis system" refers to the in vitro synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc.; and co-factors, enzymes and other reagents that are necessary for the synthesis, e.g. ribosomes, uncharged tRNAs, tRNAs charged with unnatural amino acids, polymerases, transcriptional factors, etc.

The term "cleavage activity is greater than 50% of the wild type RF1" refers to the cleavage rate of a modified protein described herein being greater than 50% of the cleavage rate of wild-type protein under specified conditions. For example, the cleavage rate can be greater than 50% of the cleavage rate of wild-type protein after 30 minutes at 30° C. when the modified and wild-type proteins are present at a similar concentration (e.g., a concentration of 0.1-1.0 micromolar) in a cell-free extract from bacteria expressing OmpT1.

The term "deleterious activity" refers to an activity that decreases the yield of proteins during protein synthesis in cell free extracts. For example, the deleterious activity can inhibit cellular transcription and/or translation in cell free synthesis systems. The deleterious activity can include enzymatic reduction of GSSG that is required for efficient protein folding of disulfide bonded proteins produced in a cell-free synthesis reaction. The deleterious activity can also include premature chain termination by a releasing factor, such that polypeptide elongation is prematurely terminated at an introduced stop codon.

A "target protein" is a protein that has been modified to include a protease cleavage site, or a protein that is modified to include a nnAA. An "essential target protein" is a protein that is required for normal growth and/or survival of a cell, such as a bacterial cell or eukaryotic cell.

A "functional Releasing Factor 1 (RF1) protein" refers to RF1 that retains activity equal to or substantially similar to wild-type or unmodified RF1 protein. Functional RF1 activity can be tested, for example, by measuring the growth rate of bacteria expressing the modified RF1 protein, and comparing the growth rate to bacteria expressing wild-type or unmodified RF1. The functional activity of other proteins modified to contain OmpT cleavage sites can be similarly determined, for example, by measuring the growth rate of bacteria expressing the modified protein, and comparing the growth rate to bacteria expressing wild-type or unmodified protein. Functional RF1 activity can also be tested, for example, by the ability of the modified RF1 protein to reduce orthogonal tRNA incorporation of a nnAA at a specified position in an mRNA encoding a target protein, thereby increasing the amount of premature chain termination (i.e., increasing the amount of truncated protein).

The term "modified to include" in the context of the present invention refers to amino acid substitutions, additions, or deletions in a protein or polypeptide sequence, or the corresponding substitutions, additions, or deletions in a nucleic acid sequence that encodes the modified protein. The modified protein can include amino acid substitutions that replace an equal number of amino acids from the wild-type protein sequence, amino acids added to the wild-type sequence, or amino acids deleted from the wild-type sequence. For example, the protein can be modified to include basic amino acids that replace the wild-type amino acid(s) at the corresponding position in the amino acid sequence. The protein can also be modified to include amino acid sequences that are known protease cleavage sequences, such as OmpT cleavage sequences.

"Non-natural" or "non-native" amino acid refers to amino acids that are not one of the twenty naturally occurring amino acids that are the building blocks for all proteins that are nonetheless capable of being biologically engineered such that they are incorporated into proteins. Non-native amino acids may include D-peptide enantiomers or any post-translational modifications of one of the twenty naturally occurring amino acids. A wide variety of non-native amino acids can be used in the methods of the invention. The non-native amino acid can be chosen based on desired characteristics of the non-native amino acid, e.g., function of the non-native amino acid, such as modifying protein biological properties such as toxicity, biodistribution, or half-life, structural properties, spectroscopic properties, chemical and/or photochemical properties, catalytic properties, ability to react with other molecules (either covalently or noncovalently), or the like. Non-native amino acids that can be used in the methods of the invention may include, but are not limited to, an non-native analogue of a tyrosine amino acid; an non-native analog of a glutamine amino acid; an non-native analog of a phenylalanine amino acid; an non-native analog of a serine amino acid; an non-native analog of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analog containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid, e.g., a sugar substituted serine or the like; a carbon-linked sugar-containing amino acid; a redox-active amino acid; an alpha-hydroxy containing acid; an amino thio acid containing amino acid; an alpha,alpha-disubstituted amino acid; a beta-amino acid; a cyclic amino acid other than praline, etc.

"Nucleic acid template" includes a DNA or RNA polynucleotide from which a polypeptide will be translated. It will be understood by those of skill in the art that a DNA nucleic acid template must first be transcribed into RNA, and that the RNA is translated into a polypeptide. DNA can be transcribed into RNA either in vivo or in vitro. The methods of in vitro transcription of a DNA template are well known in the art. In some embodiments, the DNA template is subject to simultaneous in vitro transcription and translation.

"Outer Membrane Protein T1" (OmpT1) is a surface membrane serine protease and belongs to the omptin family of gram-negative bacteria. OmpT1 is known to cleave antimicrobial peptides, activate human plasminogen, and degrade some heterologous recombinant proteins. OmpT1 and its homologs cleave synthetic substrates between dibasic residues with high catalytic efficiency. The cleavage of sequences containing dibasic residues has been shown to be important for the inactivation of antibiotic peptides and colicins, the proteolysis of bacterial membrane proteins in trans, and the degradation of recombinant proteins expressed E. coli. In the context of this invention, OmpT1 has certain advantages in that it is located on the outer membrane of the cell, and thus is not in contact with potential substrate proteins that are located inside the intact bacterial cell.

The term "oxidative phosphorylation system of the bacteria remains active" refers to a bacterial lysate that exhibits active oxidative phosphorylation during protein synthesis. For example, the bacterial lysate can generate ATP using ATP synthase enzymes and reduction of oxygen. It will be understood that other translation systems known in the art can also use an active oxidative phosphorylation during protein synthesis. The activation of oxidative phosphorylation can be demonstrated by inhibition of the pathway using specific inhibitors, such as electron transport chain inhibitors.

"Translation" refers to the process whereby an RNA template is converted into a polypeptide containing natural and/or non-native amino acids, and is well known in the art. Translation involves the initiation step, whereby a ribosome attaches to the RNA template, generally at the FMet codon (e.g., AUG), and the elongation step, whereby the anticodon of a charged tRNA molecule is paired with a codon in the RNA template, this step being repeated as the ribosome moves down the RNA template. As each tRNA anticodon is paired with its corresponding codon, the amino group of the amino acid charged to each tRNA molecule is covalently linked to the carboxyl group of the preceding amino acid via peptide bonds. Generally, translation also involves the termination step, whereby the ribosome encounters a translation stop codon, thus ending chain elongation and release of the polypeptide from the ribosome. However, in the methods described herein, the RNA template can comprise an ORF having an amber stop codon UAG, which is recognized by the anti-codon CUA of a tRNA charged with a nnAA. Therefore, in the present methods, the amber codon does not necessarily function to terminate translation.

"Translation system" refers to a mixture of components that is able to translate mRNA into polypeptides in vitro. A translation system can be a cell free extract, reconstituted cell lysate, or a purified mixture of components that is able to translate mRNA into polypeptides in vitro. For example, the cell free extract or cell lysate used in the methods described herein can be derived from *Escherichia coli* (*E. coli*). The translation system can also comprise a purified and reconstituted in vitro translation system. The methods described herein can also utilize a translation system that exhibits active oxidative phosphorylation during protein synthesis. For example, the translation system can generate ATP using ATP synthetase enzymes. The translation system can also comprise at least one nucleic acid template. The nucleic acid template can be simultaneously transcribed and translated into protein using the translation system.

"Reconstituted ribosomal translation system" refers to a mixture of purified components which is capable of translating a nucleic acid molecule such as mRNA in vitro, as described in Tan et al., *Methods* 36, 279-290 (2005), and Forster et al., U.S. Pat. No. 6,977,150, which are incorporated by reference herein in their entirety.

A "scissile OmpT1 peptide bond" is a peptide bond that is capable of being cleaved by OmpT1.

A "surface exposed motif" is a domain that is present on the outside of a protein molecule. Surface exposed motifs are generally more accessible to proteolytic cleavage, for example by a serine protease such as OmpT1. One of skill in the art would understand that a surface exposed motif can be defined in several ways. For example, a surface exposed motif often lacks secondary structure, such as alpha helix or beta sheet. Further, surface exposed motifs often do not share a significant amount of amino acid sequence homology, even between homologous protein sequences. However, one of skill in the art can calculate relative surface accessible area for regions of a protein of interest using the GetArea algorithm embedded in pymol molecular modeling software (See the internet at pymolwiki.org/index.php/Get_Area).

A "surface exposed motif having a B factor of at least 50 $Å^2$" refers to the mobility of individual atoms in the surface exposed motif Atoms in surface exposed motifs can have more mobility than atoms in the core of a protein. B-factors generally indicate the relative vibrational motion of different parts of a structure, such as a protein. Atoms with low B-factors belong to a part of the protein that is well-ordered and thus have relatively low mobility. Atoms with large B-factors generally belong to part of the protein that is relatively flexible, and thus have relatively high mobility. The higher the B-factor, the more likely that positional errors of an individual atom in a protein structure will be observed. For example, a B factor of between 40 and 60 suggests that positional errors up to 1.0 Ångstrom can be observed. A B-factor of greater than 60 suggests that the atom is not likely to be within 1.0 Ångstrom of its observed position. (See, e.g., the internet at wiki.cmbi.ru.nl/index.php/B-factor). The B-factor is calculated as:

$$B_i = 8\pi^2 U_i^2$$

where $U_i^2$ is the mean square displacement of atom i. This produces a weighting factor on the contribution of atom i to the Fourier transform by:

$$\exp\left(-B_j \frac{\sin^2\Theta}{\lambda^2}\right)$$

As U increases, B increases and the contribution of the atom to the scattering is decreased. See, e.g., the internet at: pldserver1.biochem.queensu.ca/~rlc/work/teaching/definitions.shtml. The B-factor is measured in units of $Å^2$.

The term "Ramachandran Plot" refers to a method for visualizing backbone dihedral angles ψ (Psi) versus φ (Phi) for each amino acid residue in a protein structure. Methods for calculating Phi and Psi angles are described, e.g., in Lovell, S. C. et al., Proteins: Structure, Function, and Genetics, 50:437-450 (2003), and Chen, V. B. et al., MolProbity: all-atom structure validation for macromolecular crystallography, Acta Crystallographica D66: 12-21 (2010). One can determine the Phi and Psi angles in a Ramachandran plot by referring to the above references, or, for convenience, one can use software programs freely available on the internet. For example, one can upload a coordinate file or a PDB file to the MOLPROBITY server at kinemage.biochem.duke.edu (see Chen, V. B. et al., supra). Alternatively, one can use the Ramachandran Plot Explorer available on the internet at boscoh.com/ramaplot.

The term "total solvent accessible surface area" (SASA) refers to the surface area of a protein or polypeptide that is accessible to a solvent. Solvent accessible surface area can be described in units of square ångstroms, and can be calculated using the 'rolling ball' algorithm developed by Shrake & Rupley (Shrake, A; Rupley, J A. (1973). "Environment and exposure to solvent of protein atoms. Lysozyme and insulin". *J Mol Biol* 79 (2): 351-71.). Solvent accessible surface area can also be calculated as described in Fraczkiewicz, R. and Braun, W., "Exact and efficient analytical calculation of the accessible surface areas and their gradients for macromolecules," J. Comp. Chem., 19:319-333 (1998). For convenience, one can calculate total solvent accessible surface area using software programs freely available on the internet. For example, one can use the software routine GETAREA found at the University of Texas Medical Branch website curie.utmb.edu/getarea.html to calculate solvent accessible surface area (solvation energy) of a protein molecule, as described in Fraczkiewicz, R. and Braun, W. (Id), by entering atomic coordinates in PDB (protein database) format, and specifying the desired radius of the water probe (parameters: radius of the water probe=1.4).

The term "switch loop region" refers to a surface exposed motif that links domains three and four of RF1 and forms a rigid connection that places the GGQ motif of domain 3 in contact with the peptidyl-tRNA ester linkage in the peptidyl transferase center (PTC) of the 50S subunit. Recognition of the stop codon by the termination complex stabilizes a rearranged conformation of the switch loop region, which directs domain 3 into the PTC. Rearrangement of the switch loop results in reorientation and extension of helix α7 so that the GGQ motifs docks in the PTC. See, Korostelev, A. et al., "Recognition of the amber UAG stop codon by release factor RF1," *EMBO Journal* (2010) 29, 2577-2585. The switch loop region of RF1 corresponds to amino acids 287 to 304 of SEQ ID NO:1, and comprises the following amino acid sequence: 287-QQAEASTRRNLLGSGDRS-304 (SEQ ID NO:4).

A "wild-type" protein is an unmodified protein having the amino acid sequence and/or functional activity of a native or naturally occurring protein. For example, a wild-type RF1 protein can have the sequence of SEQ ID NO:1. A "control protein" can be a wild-type protein or a previously modified protein.

"Native amino acid" refers to one or more naturally occurring amino acids encoded by the genetic code. An "endogenous native amino acid" refers to a native amino acid produced by the host cells used to generate the lysate.

"Non-native amino acids" ("nnAA") refers to chemical structures having the formula $NH_3-(CR)-COOH$ where R is not any of the 20 most common substituents defining the natural amino acids.

The terms "identical" or percent "identity," in the context of two or more nucleic acids or polypeptide sequences, refer to two or more sequences or subsequences that are the same or have a specified percentage of nucleotides or amino acid residues that are the same (e.g., 60% identity, optionally 65%, 70%, 75%, 80%, 85%, 90%, 95%, 97% or 99% identity over a specified region), when compared and aligned for maximum correspondence over a comparison window, or designated region, as measured using the BLAST and PSI-BLAST algorithms, which are described in Altschul et al. (J. Mol. Biol. 215:403-10, 1990), and Altschul, et al. (Nucleic Acids Res., 25:3389-3402, 1997), respectively. Software for performing BLAST analyses is publicly available through the National Center for Biotechnology Information (see the internet at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=-4, and a comparison of both strands.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well-known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using the algorithm described in Pearson et al. (*Meth. Mol. Biol.* 24:307-331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein.

Furthermore, it will be recognized that individual substitutions, deletions or additions that alter, add or delete a single amino acid or a small percentage of amino acids (typically less than 10%, and generally less than 1%) in an encoded sequence can be considered conservatively modified variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another:

1) Alanine (Ala, A), Serine (Ser, S), Threonine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K)
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, W).

Two or more amino acid sequences or two or more nucleotide sequences are considered to be "substantially similar" if the amino acid sequences or the nucleotide sequences share at least 50%, 60%, 70%, 80%, 90%, 95% or 99% sequence identity with each other, or with a reference sequence over a given comparison window. Two or more proteins are also considered substantially similar if they incorporate conservative amino acid substitutions providing functionally similar amino acids into the amino acid sequence.

"Promoter" refers to sequence elements in the nucleic acid template located upstream or downstream from the start of transcription. Promoter sequences are involved in recognition and binding of RNA polymerase and other proteins that initiate transcription. Examples of promoters include T7, SP6 and T3 bacteriophage promoters.

"5' untranslated region" refers to the nucleic acid sequence located upstream or 5' of the open reading frame in a nucleic acid template. In RNA, the 5' untranslated region precedes the translation start codon present in the nucleic acid template. In DNA, the 5' untranslated region refers to nucleic acid sequences that are transcribed into RNA and are located 5' to the translation start codon. In DNA, the translation start codon is typically ATG, and in RNA the translation start codon is typically AUG.

"Primary amino acid sequence" refers to the order of amino acid residues that are joined together by peptide bonds into a polypeptide. The order of amino acid residues is generally referenced starting at the amino terminal end of the polypeptide and proceeding to the carboxy terminal end of the polypeptide. The primary amino acid sequence is determined by the nucleotide sequence of RNA codons in the nucleic acid template.

"Open reading frame" refers to the nucleotide sequence of a nucleic acid template that is translated into a polypeptide of interest. As used herein, the open reading frame (ORF) can include at least one codon corresponding to a defined amino acid residue that binds to a tRNA charged with a nnAA. The at least one codon can be an amber codon.

"Isoaccepting sense tRNA" refers to different tRNA species that bind to alternate codons for the same amino acid.

"tRNA" or "transfer RNA" refers to a small RNA molecule that transfers a specific amino acid to a growing polypeptide chain at the ribosomal site of protein synthesis during translation. tRNAs contain a three base codon that pairs to the corresponding mRNA codon. As a result of the degeneracy of the genetic code, an amino acid can associate with multiple tRNAs, while each type of tRNA molecule can only associate with one type of amino acid.

The terms "polypeptide" and "protein" are used interchangeably, and refer to a compound containing two or more amino acids joined by peptide bonds. Proteins can contain one or more polypeptide chains.

The term "when the protein is uncomplexed" refers to the structure of a protein in solution, or a portion, region or domain of the structure of the protein in solution, and not the structure of the protein, or portion, region or domain of the structure of the protein, when it is part of a complex with other molecules such as proteins, ligands, enzyme substrate or inhibitor complexes, ribosomes, bound antibodies or antibody fragments, RNA, and DNA. The term also refers to the structure of a protein domain, such as the amino acids comprising a surface exposed motif, that is in solution.

As used herein, the term "about," when modifying any amount, refers to the variation in that amount typically encountered by one of skill in the art, e.g., in protein synthesis or X-ray crystallography experiments. For example, the term "about" refers to the normal variation encountered in measurements for a given analytical technique, both within and between batches or samples. Thus, the term about can include variation of 1-10% of the measured value, such as 5% or 10% variation. The amounts disclosed herein include equivalents to those amounts, including amounts modified or not modified by the term "about."

DETAILED DESCRIPTION OF THE INVENTION

Introduction

The present invention provides target proteins that are recombinantly modified to include OmpT1 protease cleavage sites that are capable of being cleaved by OmpT1. The OmpT1 cleavage site includes a scissile OmpT1 peptide bond. In one embodiment, the target protein is modified to include two adjacent basic amino acids that are positively charged at pH 7.0. In some embodiments, the target protein is modified to introduce the OmpT1 cleavage site into a surface exposed motif of the target protein. In some embodiments, the scissile OmpT1 peptide bond is located in a surface exposed motif having a B factor of at least 50 Å$^2$ when the protein or the surface exposed motif is uncomplexed (i.e., free in solution and/or not part of a macromolecular structure comprising other molecules). In some embodiments, the scissile OmpT1 peptide bond is located in a surface exposed motif having a total solvent accessible surface area (SASA) of between about 25 Å$^2$ and about 225 Å$^2$. In some embodiments, the target protein is modified such that the scissile OmpT1 peptide bond is located in a position of the protein which exhibits a Phi angle of from 0° to −180° or a Psi angle from 0° to +180° in a Ramachadran Plot.

As is understood by one of skill in the art, the above embodiments require structural information for the protein domain(s) of interest. However, surface loops often are disordered, and therefore no crystal structure may be available for the target protein of interest. Thus, in some embodiments, a homology model can be made using similar structures to predict a SASA of between about 25 Å$^2$ and about 225 Å$^2$, or a Phi angle of from 0° to −180° or a Psi angle from 0° to +180° in a Ramachadran Plot, in the absence of structural information.

The invention further provides a bacterial cell that express both OmpT1 and the recombinantly modified target protein. In some embodiments, the recombinantly modified target protein is an essential protein, for example, a protein that is required for normal cell growth and/or survival.

The target proteins described herein are selected because they have deleterious activity in an in vitro cell-free synthesis system. For example, the target protein can inhibit transcription and/or translation of nucleic acid templates that encode proteins of interest. Thus, the invention provides methods for reducing the deleterious activity of a modified essential target protein in an in vitro cell-free synthesis system by inactivating the target protein with an OmpT1 protease. In some embodiments, the method comprises culturing an OmpT1 positive bacteria expressing the modified essential target protein, where the target protein is modified to include an OmpT1 cleavage site comprising a scissile OmpT1 peptide bond in a surface exposed motif; lysing the bacteria to create a cell free synthesis extract; contacting the modified essential target protein with OmpT1 in an amount sufficient to reduce the amount of intact target protein by 50%; adding a nucleic acid template to the extract, where the template codes for a protein of interest; and allowing the cell free synthesis system to produce the protein of interest. The method takes advantage of the spatial separation of the modified target protein and the OmpT1 protease during cell growth, when the target protein may be important for cell growth and/or survival, whereas the target protein is cleaved by OmpT1 when the bacterial cells are disrupted and lysed to produce a cell-free extract.

In some embodiments of the method, the scissile OmpT1 peptide bond is located within a surface exposed motif having a B factor of at least 50 Å$^2$ when the protein or the surface exposed motif is uncomplexed. For example, the surface exposed motif can have a B factor of 50, 55, 60, 65, 70, 75, 80, 85, 90, 95, 100, 110, 120, 130, 140, 150, 160, 170, 180, 190, or 200 Å$^2$ or greater, or can be in a range of between about 50 and about 200 Å$^2$, between about 50 and about 150 Å$^2$, between about 50 and about 100 Å$^2$, between about 60 and about 200 Å$^2$, between about 60 and about 150 Å$^2$, or between about 60 and about 100 Å$^2$. In some embodiments of the method, the scissile OmpT1 peptide bond is located within a surface exposed motif having a total solvent accessible surface area of between about 25 Å$^2$ and about 225 Å$^2$. For example, in some embodiments, the total solvent accessible surface area is about 25, 30, 35, 40, 45, 50, 55, 60, 65, 70, 75, 80, 85, 90, 95, 100, 110, 120, 130, 140, 150, 160, 170, 180, 190, 200, 210, 220, or 225 Å$^2$ (where the term "about" modifies each of the preceding values). In one embodiment of the method, the scissile OmpT1 peptide bond is located in a position of the protein which exhibits a Phi angle of from 0° to −180° or a Psi angle from 0° to +180° in a Ramachadran Plot. As described above, in the absence of structural information, a homology model can be made using similar structures to predict a SASA of between about 25 Å$^2$ and about 225 Å$^2$, or a Phi angle of from 0° to −180° or a Psi angle from 0° to +180° in a Ramachadran Plot.

The proteins of interest referred to above include proteins that are engineered to incorporate non-native amino acids (nnAA) at a defined location of the amino acid sequence. The introduction of nnAA into proteins can result in proteins with preferred properties. One method for introducing nnAA into proteins or polypeptides of interest uses aminoacylated orthogonal tRNAs that recognize an amber (stop) codon for introducing the nnAA into the nascent polypeptide chain during protein translation. However, the yield of proteins having nnAA introduced therein can be decreased by proteins of the translation termination complex that facilitate the termination of translation by recognizing the termination or stop codons in an mRNA sequence. Release Factor 1 (RF1) is part of the termination complex, and recognizes the UAG (amber) stop codon. RF1 recognition of the amber codon can promote pre-mature chain termination at the site of nnAA incorporation, which reduces the yield of desired proteins. The methods described herein solve this problem by decreasing the functional activity of RF1 in bacterial cell lysates. Thus, in some embodiments, the essential target protein is RF1. The functional activity of RF1 is decreased by introducing OmpT1 protease cleavage sites into RF1. OmpT1 is an enzyme located on the outer cell membrane of intact bacteria. Thus, the modified RF1 is not available as a substrate for OmpT1 in intact cells. When the bacterial membrane is disrupted, for example, as in a bacterial lysate, the OmpT1 enzyme is able to contact and cleave the modified RF1 at the introduced cleavage site, thereby decreasing the functional activity of RF1. The methods are applicable to other releasing factors found in the translation termination complex, such as RF2, which recognizes the UGA stop codon. The methods are also applicable to proteins that degrade mRNA during in vitro translation, such as RNase enzymes. Further, the methods are generally applicable to any protein in a bacterial extract that inhibits transcription and/or translation of a protein of interest.

General Methods

Unless defined otherwise, all technical and scientific terms used herein have the meaning commonly understood by one of ordinary skill in the art to which this invention belongs. Practitioners are particularly directed to Green, M. R., and Sambrook, J., eds., Molecular Cloning: A Laboratory Manual, 4th ed., Cold Spring Harbor Laboratory Press, Cold Spring Harbor, N.Y. (2012), and Ausubel, F. M., et al., Current Protocols in Molecular Biology (Supplement 99), John Wiley & Sons, New York (2012), which are incorporated herein by reference, for definitions and terms of the art. Standard methods also appear in Bindereif, Schön, & Westhof (2005) Handbook of RNA Biochemistry, Wiley-VCH, Weinheim, Germany which describes detailed methods for RNA manipulation and analysis, and is incorporated herein by reference. Examples of appropriate molecular techniques for generating recombinant nucleic acids, and instructions sufficient to direct persons of skill through many cloning exercises are found in Green, M. R., and Sambrook, J., (Id.); Ausubel, F. M., et al., (Id.); Berger and Kimmel, Guide to Molecular Cloning Techniques, Methods in Enzymology (Volume 152 Academic Press, Inc., San Diego, Calif. 1987); and PCR Protocols: A Guide to Methods and Applications (Academic Press, San Diego, Calif. 1990), which are incorporated by reference herein.

Methods for protein purification, chromatography, electrophoresis, centrifugation, and crystallization are described in Coligan et al. (2000) Current Protocols in Protein Science, Vol. 1, John Wiley and Sons, Inc., New York. Methods for cell-free synthesis are described in Spirin & Swartz (2008) Cell-free Protein Synthesis, Wiley-VCH, Weinheim, Germany. Methods for incorporation of non-native amino acids into proteins using cell-free synthesis are described in Shimizu et al (2006) FEBS Journal, 273, 4133-4140.

PCR amplification methods are well known in the art and are described, for example, in Innis et al., PCR Protocols: A Guide to Methods and Applications, Academic Press Inc. San Diego, Calif., 1990. An amplification reaction typically includes the DNA that is to be amplified, a thermostable DNA polymerase, two oligonucleotide primers, deoxynucleotide triphosphates (dNTPs), reaction buffer and magnesium. Typically a desirable number of thermal cycles is between 1 and 25. Methods for primer design and optimization of PCR conditions are well known in the art and can be found in standard molecular biology texts such as Ausubel et al., Short Protocols in Molecular Biology, 5$^{th}$ Edition, Wiley, 2002, and Innis et al., PCR Protocols, Academic Press, 1990. Computer programs are useful in the design of primers with the required specificity and optimal amplification properties (e.g., Oligo Version 5.0 (National Biosciences)). In some embodiments, the PCR primers may additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers may also contain an RNA polymerase promoter site, such as T7 or SP6, to allow for subsequent in vitro transcription. Methods for in vitro transcription are well known to those of skill in the art (see, e.g., Van Gelder et al., Proc. Natl. Acad. Sci. U.S.A. 87:1663-1667, 1990; Eberwine et al., Proc. Natl. Acad. Sci. U.S.A. 89:3010-3014, 1992).

OmpT1 Cleavable Proteins

The present invention provides target proteins that are capable of being cleaved and inactivated by proteolytic enzymes such as OmpT1. In order to be cleaved by the protease, the proteins are modified to introduce proteolytic cleavages sites into the protein. In some embodiments, the cleavage site introduced into the modified target protein is a scissile OmpT1 peptide bond, and the scissile OmpT1 is introduced into a surface exposed motif of the target protein. The cleavage site recognized by OmpT1 comprises two adjacent basic residues. Thus, the target proteins described herein are modified to comprise two adjacent basic residues that are positively charged at pH 7.0.

Modification of Proteins to Introduce an OmpT1 Cleavage Site in a Surface Exposed Motif Having a B Factor of at Least 50 Å$^2$ In some embodiments, the target protein is modified to introduce the scissile OmpT1 peptide bond into a surface exposed motif having a B factor of at least 50 Å$^2$ when the amino acid sequence of the target protein or motif region is uncomplexed. The location of a surface exposed motif having a B factor of at least 50 Å$^2$ can be determined in several ways. B-factors are given for each atom in crystallographic Protein Data Bank (PDB) files. The B factor of a surface exposed motif can be calculated using the GetArea algorithm embedded in pymol molecular modeling software (See the internet at pymolwiki.org/index.php/Get_Area). Alternatively, if an X-ray crystallographic structure of the protein is not available, but an NMR structure of the protein is available, the random coil index (RCI) may be used in place of a large B-factor (See Berjanskii, M. V., et al., Application of the random coil index to studying protein flexibility, J Biomol NMR. 2008 January;40(1):31-48. Epub 2007 Nov. 6).

In order to modify a target protein to introduce an OmpT1 cleavage site into a surface exposed motif having a B factor of at least 50 Å$^2$, the B-factors from X-ray crystallographic structures of the protein can be mapped to the amino acid sequence, and the sequence recombinantly modified to include a scissile OmptT1 peptide bond at site(s) with large B-factors. The recombinantly modified target protein can then be tested for degradation of the protein in a cell-extract containing OmpT1. In some embodiments, the B factor is at least 50, 60, 70, 80, 90 or 100 Å$^2$. In some embodiments, the B factor is between about 50 and about 200 Å$^2$, or between about 50 and about 150 Å$^2$, or between about 50 and 120 Å$^2$. It is understood that ranges described herein include all values in between the end points.

Modification of Proteins to Introduce an OmpT1 Cleavage Site in a Surface Exposed Motif Having a Total Solvent Accessible Surface Area of Between About 25 Å$^2$ and About 225 Å$^2$.

In some embodiments, the target protein is modified to introduce the scissile OmpT1 peptide bond into a surface exposed motif having a total solvent accessible surface area of between about 25 Å$^2$ and about 225 Å$^2$. The location of a surface exposed motif having a total solvent accessible surface area of between about 25 Å$^2$ and about 225 Å$^2$ can be determined using methods known in the art. For example, the software routine GETAREA can be used to locate solvent-exposed vertices of intersecting atoms, as described in Fraczkiewicz, R. and Braun, W., "Exact and efficient analytical calculation of the accessible surface areas and their gradients for macromolecules," J. Comp. Chem., 19, 319-333 (1998). Thus, one can calculate solvent accessible surface area (solvation energy) of a protein molecule using the GETAREA software by entering atomic coordinates in PDB (protein database) format, specifying the desired radius of the water probe, and specifying the desired level of output using a form provided on the internet at the University of Texas Medical Branch website curie.utmb.edu/getarea.html (parameters: radius of the water probe=1.4). Other methods for determining total solvent accessible surface area are described in Eisenberg, D. and McLachlan, A. D. (1986) *Nature,* 319, 199; Markley, J. L.; et al. (1998) *Pure & Appl. Chem.,* 70, 117; and Wesson, L. and Eisenberg, D. (1992) *Protein Sci.,* 1, 227.

Modification of Proteins to Introduce an OmpT1 Cleavage Site in a Position of the Protein which Exhibits a Phi Angle of from 0° to −180° or a Psi Angle from 0° to +180° in a Ramachadran Plot In some embodiments, the target protein is modified to introduce the scissile OmpT1 peptide bond in a position of the protein which exhibits a Phi angle of from 0° to −180° or a Psi angle from 0° to +180° in a Ramachadran Plot. The location of the position in a protein which exhibits a Phi angle of from 0° to −180° or a Psi angle from 0° to +180° in a Ramachadran Plot can be determined using methods known in the art. Methods for calculating Phi and Psi angles are described, e.g., in Lovell, S. C. et al., Proteins: Structure, Function, and Genetics, 50:437-450 (2003). One can determine the Phi and Psi angles in a Ramachandran plot by uploading a coordinate file or a PDB file on the MOLPRO-BITY server on the internet at kinemage.biochem.duke.edu (see Chen, V. B., et al., (2010) MolProbity: all-atom structure validation for macromolecular crystallography. Acta Crystallographica D66: 12-21.). Alternatively, one can use the Ramachandran Plot Explorer available on the internet at boscoh.com/ramaplot.

The modified proteins described herein are selected because they can inhibit production of proteins in cell-free synthesis systems. Thus, in some embodiments, the modified proteins described herein decrease the production of full length proteins in bacterial cell-free extracts. For example, the proteins RF1 and RF2 are part of the termination complex that recognizes a stop codon in the mRNA and terminates translation of the polypeptide chain. Premature termination of translation is undesirable when incorporating non-native amino acids into a protein using cell free translation systems as described herein. Reducing recognition of the stop codon by the termination complex can increase the yield of proteins incorporating nnAA. Thus, in some embodiments, the RF1 and/or RF2 protein, or a function homolog thereof, is modified to contain OmpT1 cleavage sites in a surface exposed motif having a B Factor of at least 50 Å$^2$ when the RF1 and/or RF2 protein, or functional homolog thereof, is uncomplexed. In some embodiments, the RF1 and/or RF2 protein, or a function homolog thereof, is modified to contain OmpT1 cleavage sites in a surface exposed motif having a total solvent accessible surface area of between about 25 Å$^2$ and about 225 Å$^2$. In some embodiments, the RF1 and/or RF2 protein, or a function homolog thereof, is modified to contain OmpT1 cleavage sites in a position of the protein which exhibits a Phi angle of from 0° to −180° or a Psi angle from 0° to +180° in a Ramachadran Plot. In some embodiments, the functional modified protein is substantially similar to RF1 (SEQ ID NO:1) or RF2 (SEQ ID NO:2).

The RF1 protein includes the RF1 wildtype prototype protein (SEQ ID NO:1) from E. coli as well as polymorphic variations and recombinantly created muteins. RF1 proteins are defined as having substantially the same biological activity or functional capacity as the wild type (e.g., at least 80% of either), have at least 60%, 70%, 80%, 90% or 95% sequence identity to the prototype protein RF1, and/or bind to polyclonal antibodies generated against the prototype protein SEQ ID NO:1.

With regard to the binding of an RF1 protein to polyclonal antibodies, the RF1 protein will bind under designated immunoassay conditions to the specified antibodies with a specificity at least two times the background, where the antibodies do not substantially bind in a significant amount to other proteins present in the sample. For example, polyclonal antibodies raised to RF1 (SEQ ID NO:1), or isoforms or portions thereof, can be selected to obtain only those polyclonal antibodies that are specifically immunoreactive with RF1 and not with other proteins, except for polymorphic variants of RF1. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically a specific or selective reaction will be at least twice background signal or noise and more typically more than 10 to 100 times background.

As described in the Examples, RF1 was successfully modified to introduce functional OmpT1 cleavage sites in a surface exposed motif. However, the introduction of putative dibasic OmpT1 cleavage sites into RF1 did not always result in a protein that could be efficiently cleaved by OmpT1. For example, the single amino acid substitutions M74R, E76K, E84K, A85R, E87R, E108R, T293R and S304K were introduced into the loop regions of RF1 beside an existing Arg or Lys, thereby creating dibasic cleavage sites. However, these variants were not efficiently cleaved when the RF1 variants were expressed in OmpT positive cell extracts. The present invention therefore provides the unexpected result that proteins such as RF1 can be modified such that the protein is capable of being cleaved by a protease such as OmpT1.

As will be understood by persons of skill in the art, the introduced cleavage site can be cleaved by an enzyme with OmpT1-like enzyme activity, where the enzyme activity results from a functional homolog or fragment of OmpT1, or from a protein that is modified to have OmpT1-like activity.

Cleavage of Unmodified Proteins by OmpT1

The proteins described herein can also contain endogenous OmpT1 protease cleavage sites. For example, in some embodiments, the unmodified or wild-type protein contains a dibasic amino acid sequence comprising a scissile OmpT1 peptide bond that is cleavable by OmpT1. Cleavage of the protein by OmpT1 can be tested by incubating the purified protein with bacterial cell-free extracts that express OmpT1, and comparing the amount of cleavage therein with the amount of cleavage detected in cell-free extracts that do not express OmpT1. In some embodiments, the unmodified proteins containing endogenous OmpT1 cleavage sites are necessary or required for normal cell growth or function, but inhibit the translation of proteins in cell-free extracts. Thus, the invention provides methods for selectively inactivating unmodified proteins by cleavage with OmpT1, where the timing of inactivation can be controlled such that the proteins are functional during cell growth, but are inactivated in cell-extracts expressing OmpT1.

Template

In order to produce the proteins of this invention, one needs a nucleic acid template. Templates for the invention are used to produce the proteins modified to comprise a scissile OmpT1 cleavage site. Templates for the invention are also used to produce proteins of interest that are expressed in cell-free systems. The templates for cell-free protein synthesis can be either mRNA or DNA. The template can comprise sequences for any particular gene of interest, and may encode a full-length polypeptide or a fragment of any length thereof. Nucleic acids that serve as protein synthesis templates are optionally derived from a natural source or they can be synthetic or recombinant. For example, DNAs can be recombinant DNAs, e.g., plasmids, viruses or the like.

In one embodiment, the DNA template comprises an ORF encoding a target protein comprising an OmpT1 cleavage site. For example, the ORF can encode a modified target protein that is required for normal cell growth and survival, but whose activity decreases the yield of proteins in cell-free extracts, either directly or indirectly. Thus, the ORF may encode a protein component of the termination complex, such as RF1 or RF2 or modified variants thereof. The ORF may also encode an RNase that degrades RNA templates.

In another embodiment, the DNA template comprises an ORF encoding a protein of interest that is modified to incorporate a non-native amino acid. Thus, the ORF may encode any protein having biological importance that incorporates a nnAA at a defined position of the amino acid sequence. Non-limiting examples of such proteins of interest include antibodies, hormones, cytokines, and viral proteins. The invention uses sense codons for the incorporation of non-native amino acids, and circumvents the requirement of orthogonal components as is commonly found in the art. In these embodiments, the ORF comprises at least one isoaccepting sense codon. The ORF further comprises one codon corresponding to a defined amino acid residue that recognizes a tRNA charged with a non-native amino acid. In some embodiments, the ORF comprises an amber codon (UAG) that binds a tRNA charged with a non-native amino acid. In other embodiments, the template is capable of translating a complete and functional protein regardless of whether non-native amino acids are chosen to be incorporated into the protein of interest.

A DNA template that comprises the ORF of interest will be operably linked to at least one promoter and to one or more other regulatory sequences including without limitation repressors, activators, transcription and translation enhancers, DNA-binding proteins, etc. Suitable quantities of DNA template for use herein can be produced by amplifying the DNA in well known cloning vectors and hosts, or by polymerase chain reaction (PCR).

The DNA template can further comprise the ORF of interest joined in frame to nucleic acid sequences that encode amino acid sequences that are useful for isolating and purifying the expressed protein, such as poly-amino acid tags that bind with high affinity to chromatography media. The poly-amino acid tag can be located at the 5' end or 3' end of the ORF, resulting in an amino-terminal or carboxyl terminal tag in the expressed protein, respectively. In one embodiment, the ORF is joined in frame to sequences that encode a poly-Histidine tag.

One embodiment uses a bacterial lysate. A DNA template can be constructed for bacterial expression by operably linking a desired protein-encoding DNA to both a promoter sequence and a bacterial ribosome binding site (Shine-Delgarno sequence). Promoters suitable for use with the DNA template in the cell-free transcription-translation methods of the invention include any DNA sequence capable of promoting transcription in vivo in the bacteria from which the bacterial extract is derived. Preferred are promoters that are capable of efficient initiation of transcription within the host cell. DNA encoding the desired protein and DNA containing the desired promoter and Shine-Dalgarno (SD) sequences can be prepared by a variety of methods known in the art. Alternatively, the desired DNA sequences can be obtained from existing clones or, if none are available, by screening DNA libraries and constructing the desired DNA sequences from the library clones.

RNA templates encoding the protein of interest can be conveniently produced from a recombinant host cell transformed with a vector constructed to express a mRNA with a bacterial ribosome binding site (SD sequence) operably linked to the coding sequence of the desired gene such that the ribosomes in the reaction mixture are capable of binding to and translating such mRNA. Thus, the vector carries any promoter capable of promoting the transcription of DNA in the particular host cell used for RNA template synthesis.

Because it is difficult to extract un-degraded RNA from bacteria, higher eukaryotic cell culture is preferred for the production of the RNA template. In principle, any higher eukaryotic cell culture is workable, including both vertebrate and invertebrate cell cultures. The RNA template can be conveniently isolated in a total cellular RNA fraction extracted from the host cell culture. Total cellular RNA can be isolated from the host cell culture by any method known in the art. The desired RNA template can be isolated along with most of the cellular mRNA if the RNA template is designed to contain at its 3' end a polyadenylation signal recognized by the eukaryotic host cell. Thus, the host cell will produce the RNA template with a polyadenylate (poly (A)) tail. Polyadenylated mRNAs can be separated from the bulk of cellular RNA by affinity chromatography on oligodeoxythymidylate (oligo (dT))-cellulose columns using any methods known in the art. If the size of the mRNA encoding the desired protein is known, the mRNA preparation can be further purified for mRNA molecules of the particular size by agarose gel electrophoresis of the RNA.

Expression of Modified Proteins Having OmpT1 Cleavage Sites

Once the nucleic acid template is produced, the template is used to express the recombinant target protein comprising an OmpT1 cleavage site in a cell, or to synthesize a modified recombinant target protein in a cell-free translation system. For example, the template can be added to a cell lysate under conditions sufficient to translate the template into protein. The cell lysate can be from bacterial cells or eukaryotic cells. The expressed protein can then be purified using methods known in the art, as described below.

Purifying Proteins to Test for Activity

Proteins containing OmpT1 cleavage sites can be purified as is standard in the art. Proteins of the invention can be recovered and purified by methods including, but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis, etc. For example, proteins comprising N-terminal Histidine tags can be purified using affinity media containing metal ions such as nickel and cobalt. The affinity media is then washed to remove unbound protein, and the bound proteins eluted and recovered. In some embodiments, the poly-histidine tagged proteins are purified using Immobilized Metal Affinity Chromatography (IMAC). The modified proteins can also be purified using high performance liquid chromatography (HPLC), or other suitable methods where high purity is desired. A preferred purification method is provided in Example 1.

Following purification, proteins containing OmpT1 cleavage sites can possess a conformation different from the desired conformations of the relevant polypeptides. Thus, the purified proteins can be subjected to conditions that result in the preferred protein conformation. A variety of purification/protein folding methods are known in the art, e.g., Deutscher, Methods in Enzymology Vol. 182: Guide to Protein Purification (Academic Press, Inc. N.Y. 1990); Bollag et al., Protein Methods, 2nd Edition, (Wiley-Liss, N.Y. 1996). In general, it is occasionally desirable to denature and reduce expressed polypeptides and then to cause the polypeptides to re-fold into the preferred conformation. For example, guanidine, urea, DTT, DTE, and/or a chaperone can be added to a translation product of interest. Methods of reducing, denaturing and renaturing proteins are well known to those of skill in the art. See, e.g. Debinski et al., J. Biol. Chem. 268:14065-70 (1993); Buchner et al., Anal. Biochem. 205:263-70 (1992).

Confirmation of Functional Biological Activity of Modified Proteins Having OmpT1 Cleavage Sites Depending on the desired use of the modified proteins described herein, it can be important for the modified proteins to have biological activity comparable to an unmodified, wild-type protein. For example, if the protein to be modified is important for normal growth of bacteria, it is desirable to retain the normal activity levels of the protein until the cells are lysed to produce the cell-free lysate for translation. Thus, the methods of the present invention provide for modified proteins containing OmpT1 cleavage sites that have biological activity comparable to the native or wild-type protein. Modified proteins that retain wild-type levels of activity, or activity levels that are comparable to wild-type, are referred to herein as a functional proteins. One may determine the specific activity of a protein by determining the level of activity in a functional assay. Alternatively, one may determine the specific activity of a protein by quantitating the amount of protein present in a non-functional assay, e.g. immunostaining, ELISA, quantitation on coomasie or silver stained gel, etc., and determining the ratio of biologically active protein to total protein. Generally, a modified protein is comparable to a wild-type protein if the specific activity as thus defined is at least about 50% of the wild-type protein, or at least about 60%, about 70%, about 80%, about 90% or greater than that of the wild-type protein. See, e.g., Sambrook et al., Molecular Cloning: A Laboratory Manual (Cold Spring Harbor Press, Cold Spring Harbor, N.Y. 1989).

The functional activity of modified proteins can be tested in a variety of ways. For example, the growth rate of bacteria expressing the modified protein can be compared to the growth rate of bacteria expressing a wild-type, control or unmodified protein. The functional activity of modified proteins can also be tested by determining the ability of the modified protein to terminate translation at a stop codon in the mRNA template. Termination of translation results in truncated proteins, and thus the relative activities of modified proteins can be quantitated by measuring the amount of truncated and full length protein, and comparing the ratio of truncated to full length protein with that resulting from wild-type protein, as described in the Examples and shown in FIG. 1. A modified protein has comparable activity to a wild-type protein if the ratio of truncated to full length protein is at least about 50%, 60%, 70%, 80%, 90%, 95%, or greater than the ratio of truncated to full length protein using a wild-type protein.

Confirmation that Modified Proteins are Cleavable by OmpT1

Once the modified proteins are determined to have comparable biological activity to the wild-type or unmodified protein, the modified proteins are tested to determine that they are cleaved by OmpT1. One method for testing that the modified proteins of the invention are cleaved by OmpT1 is to add recombinant protein containing OmpT1 cleavage sites to a cell-free extract containing functional OmpT1. If the modified protein is cleaved by OmpT1, it will migrate at an apparent lower molecular weight than the intact protein during gel electrophoresis (e.g., SDS-PAGE). The modified protein can be detected by including a radioactive label such as $^{14}C$ in the translation reaction under conditions suitable for incorporation of the radioactive label into the modified protein. The migration of the radioactively labeled protein can be visualized, for example, on an autoradiograph of the gel. Cleavage of the modified protein by OmpT1 can also be detected by Western blot analysis, for example, by transferring the proteins from the gel to a solid support, contacting the support with antibodies that bind to the intact and cleaved protein, and visualizing the bound antibodies using a detectable label.

The cleavage activity by OmpT1 can be determined by comparing the amount or rate of cleavage of a modified protein by OmpT1 to that of an unmodified protein. For example, the cleavage rate of the modified protein by OmpT1 can be greater than 50% of the cleavage rate of the wild-type protein under specified conditions. In some embodiments, the cleavage rate of a modified protein described herein is greater than 50% of the cleavage rate of wild-type protein after 30 minutes at 30° C. when the modified and wild-type proteins are present at a similar concentration (e.g., a concentration of 0.1-1.0 micromolar) in a cell-free extract from bacteria expressing OmpT1. In some embodiments, greater than 90% of the modified protein is cleaved by OmpT1 after 60 minutes at 30° C. when the modified protein is present at a concentration of 0.1-1.0 micromolar in a cell-free extract from bacteria expressing OmpT1.

It will be understood that the OmpT cleavage sites introduced into the modified proteins described herein are cleavable by any protein or polypeptide that possesses OmpT-like enzyme activity. All that is required is that the OmpT1-like enzyme be capable of cleaving a protein modified to contain OmpT cleavage sites. For example, the OmpT-like proteolytic activity can be provided by wild-type or native OmpT1, or a functional homolog or fragment thereof. The OmpT-like activity can also be provided by a protein that is substantially identical or substantially similar to OmpT1. For example, the protein with OmpT-like activity can have at least 60%, 70%, 80%, 90%, 95% or 99% sequence identity to OmpT1. In some embodiments, the protein having OmpT-like activity is at least 60%, 70%, 80%, 90%, 95% or 99% identical to SEQ ID NO:3. In some embodiments, the protein having OmpT1 activity is specifically bound by a polyclonal antibody that binds to OmpT1 and variants thereof. Selection of polyclonal antibodies that bind to OmpT1 and functional variants thereof can be performed as described herein for selecting polyclonal antibodies that bind RF1.

Transforming Bacteria with the OmpT1 Cleavable Proteins

Once the modified essential target proteins are determined to retain wild-type function and to be susceptible to cleavage by OmpT1, as described above, nucleic acids encoding the modified proteins are transformed into bacteria. The bacteria can be transformed with the nucleic acid under conditions suitable for incorporation of the nucleic acid into the genome of the bacteria. For example, the bacteria can be transformed with oligonucleotides having sequences that encode the OmpT1 cleavage sites described herein using oligonucleotide-mediated allelic replacement, as described in the Examples. Incorporation of the desired mutations in the bacterial genome can be determined, for example, by screening transformed colonies using Mismatch Amplification Mutation Assay (MAMA) PCR, as described in the Examples.

Use of OmpT1 Cleavable Proteins to Increase the Yield of Proteins in Cell-Free Translation Systems The modified target proteins having OmpT1 cleavage sites are efficiently degraded when expressed in a bacterial cell extract that contains active OmpT1 protease. Among the various uses of this invention, careful selection of inhibitory proteins that are modified to be cleavable by OmpT1 can enhance the productivity of cell-free synthesis systems. For example, in one preferred use, the cleavage of selected target proteins by OmpT1 can improve the translation efficiency of full length proteins incorporating non-native amino acids in cell-free extracts. In certain embodiments, the non-native amino acid is incorporated at an amber codon introduced into the mRNA template. As described above, the incorporation of non-native amino acids at an amber codon can be inhibited by termination complex proteins such as RF1 and RF2. Thus, in a particularly desirable embodiment, cleavage and inactivation of RF1 and/or RF2 by OmpT1 can increase the yield of proteins engineered to incorporate a non-native amino acid at an amber codon.

Non-Native Amino Acids

As described above, in one preferred use, degradation of the modified target protein by OmpT1 increases the yield of proteins incorporating non-native amino acids in cell-free synthesis systems. The non-native amino acids used in the present invention typically comprise one or more chemically modified derivatives or analogues of amino acids, wherein the chemical structures have the formula NH3-(CR)—COOH, where R is not any of the 20 canonical substituents defining the natural amino acids. Suitable non-native amino acid derivatives are commercially available from vendors such as, e.g., Bachem Inc., (Torrance, Calif.); Genzyme Pharmaceuticals (Cambridge, Mass.); Senn Chemicals (Dielsdorf, Switzerland); Sigma-Aldrich (St. Louis, Mo.); Synthetec, Inc (Albany, Oreg.). Preferably, the non-native amino acids include but are not limited to derivatives and/or analogs of glycine, tyrosine, glutamine, phenyalanine, serine, threonine, proline, tryptophan, leucine, methionine, lysine, alanine, arginine, asparagine, valine, isoleucine, aspartic acid, glutamic acid, cysteine, histidine, as well as beta-amino acids and homologs, BOC-protected amino acids, and FMOC-protected amino acids.

The generation of non-native amino acid derivatives, analogs and mimetics not already commercially available can be accomplished in several ways. For example, one way is to synthesize a non-native amino acid of interest using organic chemistry methods known in the art, while another way is to utilize chemoenzymatic synthesis methods known in the art. See, e.g., Kamphuis et al., *Ann. N. Y. Acad. Sci.,* 672:510-527, 1992; Ager D J and Fotheringham I G, *Curr. Opin. Drug Discov. Devel.,* 4:800-807, 2001; and Weiner et al., *Chem. Soc. Rev.,* 39:1656-1691, 2010; Asymmetric Syntheses of Unnatural Amino Acids and Hydroxyethylene Peptide Isosteres, Wieslaw M. Kazmierski, ed., *Peptidomimetics Protocols,* Vol. 23, 1998; and Unnatural Amino Acids, Kumar G. Gadamasetti and Tamim Braish, ed., *Process Chemistry in the Pharmaceutical Industry,* Vol. 2, 2008.

One skilled in the art will recognize that many procedures and protocols are available for the synthesis of non-native amino acids, for example, as described in Wieslaw M. Kazmierski, ed., *Peptidomimetics Protocols,* Vol. 23, 1998; Wang L et al., *Chemistry and Biology,* 16:323-336, 2009; and Wang F, Robbins S, Guo J, Shen W and Schultz P G., *PLoS One,* 5:e9354, 2010.

The non-native amino acids may include non-native L- and D-alpha amino acids. L-alpha amino acids can be chemically synthesized by methods known in the art such as, but not limited to, hydrogen-mediated reductive coupling via rhodium-catalyzed C—C bond formation of hydrogenated conjugations of alkynes with ethyl iminoacetates (Kong et al., *J. Am. Chem. Soc.,* 127:11269-11276, 2005). Alternatively, semisynthetic production by metabolic engineering can be utilized. For example, fermentation procedures can be used to synthesize non-native amino acids from *E. coli* harboring a re-engineered cysteine biosynthetic pathway. (see Maier T H, Nature, 21:422-427, 2003). Racemic mixtures of alpha-amino acids can be produced using asymmetric Strecker syntheses (as described in Zuend et al., Nature, 461;968-970 (2009)) or using transaminase enzymes for large-scale synthesis (as found in Taylor et al., *Trends Biotechnol.,* 16:412-419, 1998. Bicyclic tertiary alpha-amino acids may be produced by alkylation of glycine-derived Schiff bases or nitroacetates with cyclic ether electrophiles, followed by acid-induced ring opening and cyclization in $NH_4OH$ (see Strachan et al., *J. Org. Chem.,* 71:9909-9911 (2006)).

The non-native amino acids may further comprise beta-amino acids, which are remarkably stable to metabolism, exhibit slow microbial degradation, and are inherently stable to proteases and peptidases. An example of the synthesis of beta amino acids is described in Tan C Y K and Weaver D F, *Tetrahedron,* 58:7449-7461, 2002.

In some instances, the non-native amino acids comprise chemically modified amino acids commonly used in solid phase peptide synthesis, including but not limited to, tert-butoxycarbonyl-(Boc) or (9H-fluoren-9-ylmethoxy)carbonyl (Fmoc)-protected amino acids. For example, Boc derivatives of leucine, methionine, threonine, tryptophan and proline can be produced by selective 3,3-dimethyldioxirane side-chain oxidation, as described in Saladino et al., *J. Org. Chem.,* 64:8468-8474, 1999. Fmoc derivatives of alpha-amino acids can be synthesized by alkylation of ethyl nitroacetate and transformation into derivatives (see Fu et al., *J. Org Chem.,* 66:7118-7124, 2001).

Non-native amino acids that can be used in the present invention may include, but are not limited to, non-native analogues or derivatives of the 20 canonical amino acid substituents. One of skill in the art will appreciate that the synthesis of various non-native amino acids may involve an array of chemical and chemo-enzymatic methods known in the art. In some embodiments, non-native amino acids may be synthesized according to procedures known in the art specific to a particular derivative of each non-native amino acid. Sycheva et al., *Microbiology,* 76:712-718, 2007 describes a procedure for synthesizing the non-native amino acids norvaline and norleucine. Diallylated proline derivatives can be produced by practical stereoselective synthesis (see Belvisi et al., *Tetrahedron,* 57:6463-6473, 2001). For example, tryptophan derivatives can be synthesized by ytterbium triflate catalyzed electrophilic substitution of indo as described in Janczuk et al., *Tetrahedron Lett.,* 43:4271-4274, 2002, and synthesis of 5-aryl tryptophan derivatives is detailed in Wang et al., *Tetrahedron,* 58:3101-3110, 2002. Non-native serine analogs can be produced by beta-fragmentation of primary alkoxyl radicals (see Boto et al., *J. Org. Chem.,* 72:7260-7269, 2007). Alternatively, a procedure for phenylserine synthesis is described in Koskinen et al., *Tetrahedron Lett.,* 36:5619-5622, 1995. The procedure for the synthesis of L-phenylglycine is described in Cho et al., *Biotechnol. Bioprocess. Eng.*, 11;299-305, 2006. And a chemo-enzymatic method of synthesizing D-4-hydroxyphenylglycine is described in Yu et al., *Folia Microbiol* (Praha), 54:509-15; 2009. A non-limiting example of the production of 2-naphthylalanine or Boc-protected 2-naphthylalanine is detailed in Boaz et al., *Org. Process Res. Dev.*, 9:472-478; 2005. Synthesis of iodo-L-tyrosine and p-benzoyl-L-phenylalanine are described in Hino N, *Nat. Protoc.*, 1:2957-2962, 2007.

Charged tRNA

In order to incorporate the non-native amino acids described herein into the desired polypeptide, the nnAA described above need to be charged to isoaccepting sense or amber codon tRNAs. The tRNA charging reaction, as used herein, refers to the in vitro tRNA aminoacylation reaction in which desired isoaccepting sense codon or amber codon tRNAs are aminoacylated with their respective amino acid of interest. The tRNA charging reaction comprises the charging reaction mixture, an isoaccepting sense tRNA, and as used in this invention, may include either natural or non-native amino acids. The tRNA charging reaction can occur in situ in the same reaction as the cell-free translation reaction, or can occur in a separate reaction, where the charged tRNA is then added to the cell-free translation reaction.

tRNA molecules to be used in the tRNA charging reaction can be synthesized from a synthetic DNA template for any tRNA of choice following amplification by PCR in the presence of appropriate 5' and 3' primers. The resulting double-stranded DNA template, containing a T7-promoter sequence, can then be transcribed in vitro using T7 RNA polymerase to produce the tRNA molecule, which is subsequently added to the tRNA charging reaction.

The tRNA charging reaction can be any reaction that aminoacylates a sense codon or amber codon tRNA molecule with a desired amino acid separate from the protein synthesis reaction. This reaction can take place in an extract, an artificial reaction mixture, or a combination of both. Suitable tRNA aminoacylation reaction conditions are well known to those of ordinary skill in the art. Typically, tRNA aminoacylation is carried out in a physiological buffer with a pH value ranging from 6.5 to 8.5, 0.5-10 mM high energy phosphate (such as ATP), 5-200 mM $MgCl_2$, 20-200 mM KCl. Preferably, the reaction is conducted in the presence of a reducing agent (such as 0-10 mM dithiothreitol). Where the aminoacyl-tRNA synthetase is exogenously added, the concentration of the synthetase is typically 1-100 nM. One skilled in the art would readily recognize that these conditions can be varied to optimize tRNA aminoacylation, such as high specificity for the pre-selected amino acids, high yields, and lowest cross-reactivity.

In other embodiments of the invention, isoaccepting or amber tRNAs are charged by aminoacyl-tRNA synthetases. The tRNA charging reactions can utilize either the native aminoacyl-tRNA synthetase specific to the isoaccepting sense tRNAs to be charged, an engineered aminoacyl-tRNA synthetase, or a "promiscuous" aminoacyl tRNA synthetase capable of charging a tRNA molecule with more than one type of amino acid. Promiscuous aminoacyl-tRNA synthetases may either themselves be engineered, or may include endogenously produced aminoacyl-tRNA synthetases that are sometimes found in nature. Methods of charging isoaccepting tRNAs with native and non-native amino acids using aminoacyl-tRNA synthetases are described in WO2010/081110, the contents of which are incorporated by reference herein.

Translation Systems

The above described charged isoaccepting sense or amber tRNAs are now combined with a translation system which can comprise a cell free extract, cell lysate, or reconstituted translation system, along with the nucleic acid template for synthesis of the desired polypeptide or protein having non-native amino acids at preselected (defined) positions. The reaction mixture will further comprise monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. In addition to the above components such as a cell-free extract, nucleic acid template, and amino acids, materials specifically required for protein synthesis may be added to the reaction. The materials include salts, folinic acid, cyclic AMP, inhibitors for protein or nucleic acid degrading enzymes, inhibitors or regulators of protein synthesis, adjusters of oxidation/reduction potentials, non-denaturing surfactants, buffer components, spermine, spermidine, putrescine, etc. Various cell-free synthesis reaction systems are well known in the art. See, e.g., Kim, D. M. and Swartz, J. R. Biotechnol. Bioeng. 66:180-8 (1999); Kim, D. M. and Swartz, J. R. Biotechnol. Prog. 16:385-90 (2000); Kim, D. M. and Swartz, J. R. Biotechnol. Bioeng. 74:309-16 (2001); Swartz et al, Methods MoL Biol. 267:169-82 (2004); Kim, D. M. and Swartz, J. R. Biotechnol. Bioeng. 85:122-29 (2004); Jewett, M. C. and Swartz, J. R., Biotechnol. Bioeng. 86:19-26 (2004); Yin, G. and Swartz, J. R., Biotechnol. Bioeng. 86:188-95 (2004); Jewett, M. C. and Swartz, J. R., Biotechnol. Bioeng. 87:465-72 (2004); Voloshin, A. M. and Swartz, J. R., Biotechnol. Bioeng. 91:516-21 (2005). Additional conditions for the cell-free synthesis of desired polypeptides are described in WO2010/081110, the contents of which are incorporated by reference herein in its entirety.

In some embodiments, a DNA template is used to drive in vitro protein synthesis, and RNA polymerase is added to the reaction mixture to provide enhanced transcription of the DNA template. RNA polymerases suitable for use herein include any RNA polymerase that functions in the bacteria from which the bacterial extract is derived. In other embodiments, an RNA template is used to drive in vitro protein synthesis, and the components of the reaction mixture can be admixed together in any convenient order, but are preferably admixed in an order wherein the RNA template is added last, thereby minimizing potential degradation of the RNA template by nucleases.

Cell Free Translation Systems

Cell-free protein synthesis can exploit the catalytic power of the cellular machinery. Obtaining maximum protein yields in vitro requires adequate substrate supply, e.g. nucleoside triphosphates and amino acids, a homeostatic environment, catalyst stability, and the removal or avoidance of inhibitory byproducts. The optimization of in vitro synthetic reactions benefits from recreating the in vivo state of a rapidly growing organism. In some embodiments of the invention, cell-free synthesis is therefore performed in a reaction where oxidative phosphorylation is activated, i.e. the CYTOMIM™ system. The CYTOMIM™ system is defined by using a reaction condition in the absence of polyethylene glycol with optimized magnesium concentration. The CYTOMIM™ system does not accumulate phosphate, which is known to inhibit protein synthesis, whereas conventional secondary energy sources result in phosphate accumulation. Various other features of the CYTOMIM™ system are described in U.S. Pat. No. 7,338,789, the contents of which are incorporated by reference herein in its entirety.

The presence of an active oxidative phosphorylation pathway can be demonstrated by the lack of a requirement for secondary energy sources, such as phosphoenolpyruvate, creatine phosphate, acetyl phosphate, or glycolytic intermediates such as glucose, glucose-6-phosphate, and pyruvate. The presence of an active oxidative phosphorylation pathway can also be determined by sensitivity of the pathway to inhibitors, such as electron transport chain inhibitors. Examples of electron transport chain inhibitors include 2-heptyl-4-hydroxyquinoline-N-oxide (HQNO), 2,4-dinitrophenol, cyanide, azide, thenoyltrifluoroacetone, and carbonyl-cyanide-m-chlorophenylhydrazone. Alternatively, in one embodiment, the cell-free translation system does not comprise an active oxidative phosphorylation pathway.

In vitro, or cell-free, protein synthesis offers several advantages over conventional in vivo protein expression methods. Cell-free systems can direct most, if not all, of the metabolic resources of the cell towards the exclusive production of one protein. Moreover, the lack of a cell wall and membrane components in vitro is advantageous since it allows for control of the synthesis environment. For example, tRNA levels can be changed to reflect the codon usage of genes being expressed. The redox potential, pH, or ionic strength can also be altered with greater flexibility than with in vivo protein synthesis because concerns of cell growth or viability do not exist. Furthermore, direct recovery of purified, properly folded protein products can be easily achieved.

The productivity of cell-free systems has improved over 2-orders of magnitude in recent years, from about 5 µg/ml-hr to about 500 µg/ml-hr. Such improvements have made in vitro protein synthesis a practical technique for laboratory-scale research and provides a platform technology for high-throughput protein expression. It further indicates the feasibility for using cell-free technologies as an alternative means to in vivo large-scale, commercial production of protein pharmaceuticals.

Generating a Lysate

The present invention utilizes a cell lysate for in vitro translation of a target protein. For convenience, the organism used as a source for the lysate may be referred to as the source organism or host cell. Host cells may be bacteria, yeast, mammalian or plant cells, or any other type of cell capable of protein synthesis. A lysate comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), any transcription activators that are required for initiation of transcription of DNA encoding the desired protein, transfer ribonucleic acids (tRNAs), aminoacyl-tRNA synthetases, 70S ribosomes, $N^{10}$-formyltetrahydrofolate, formylmethionine-tRNAf$^{met}$ synthetase, peptidyl transferase, initiation factors such as IF-1, IF-2, and IF-3, elongation factors such as EF-Tu, EF-Ts, and EF-G, release factors such as RF-1, RF-2, and RF-3, and the like.

An embodiment uses a bacterial cell from which a lysate is derived. A bacterial lysate derived from any strain of bacteria can be used in the methods of the invention. The bacterial lysate can be obtained as follows. The bacteria of choice are grown up overnight in any of a number of growth media and under growth conditions that are well known in the art and easily optimized by a practitioner for growth of the particular bacteria. For example, a natural environment for synthesis utilizes cell lysates derived from bacterial cells grown in medium containing glucose and phosphate, where the glucose is present at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as E. coli, using both defined and undefined sources of nutrients. Cells that have been harvested overnight can be lysed by suspending the cell pellet in a suitable cell suspension buffer, and disrupting the suspended cells by sonication, breaking the suspended cells in a French press, continuous flow high pressure homogenization, or any other method known in the art useful for efficient cell lysis The cell lysate is then centrifuged or filtered to remove large DNA fragments.

EXAMPLES

Example 1

This example describes the modification of RF1 protein to introduce amino acid sequences that are cleavable by OmpT1 protease.

Methods:

Construction of a Template to Introduce OMPT1 Cleavage Sites into RF1

A PCR based strategy was used to introduce desired nucleotide sequence changes into nucleic acid templates that encode the modified RF1 proteins described herein. The PCR reaction was carried out using Phusion Hot Start Flex 2X Master Mix (NEB) according to the protocols suggested by the manufacturer. Generally a two-step overlapping PCR was carried out to introduce OmpT cleavage mutations into the RF1 encoding gene, as described in more detail below. PCR generated DNA templates were purified using QIAquick PCR purification kit (QIAGEN) for application in cell-free expression. After PCR purification the variants were sequenced by Mclab (South San Francisco, Calif.) to confirm the presence of the expected mutations.

Preparation of GamS Protein to Prevent Degradation of DNA Templates in Cell-Free Reactions The efficiency of transcription from a DNA template can be decreased due to degradation of the template by endogenous bacterial exonucleases present in cell-free extracts. The short form of λ phage Gam protein (GamS) is known to protect DNA templates from degradation by inhibiting the activity of RecBCD (Exonuclease V) (see Sitararman, K., Esposito, D., Klarmann, G., Grice, S. F. L., Hartley, J. L. and Chatterjee, D. K. 2004, A Novel Cell-free Protein Synthesis System. J Biotechnol. 110: 257-263. Therefore, GamS protein was used in this example to stabilize PCR templates during cell-free transcription reactions. To produce recombinant GamS protein, the GamS gene was amplified to include a C-terminal poly-histidine tag, GGSHHHHHH (SEQ ID NO:50), by primers, 5'-ATATATCATAT-GAACGCTTATTACATTCAGGATCGTCTTGAG-3' (SEQ ID NO:51), and 5'-ATATATGTCGACTTAATGATGAT-GATGATGATGAGAACCCCCTACCTCTGAATCAATAT-CAACCTGGTGGTG-3' (SEQ ID NO:52) using pKD46 (Datsenko, K. A. and Wanner, B. 2000, One-step Inactivation of Chromosomal Genes in Escherichia coli K-12 Using PCR Products. Proc. Natl. Acad. Sci. USA 97: 6640-6645) as template. The GamS gene was subcloned into the cell-free expression plasmid pYD317 at NdeI/SalI restriction sites. GamS was expressed in vitro and purified by Immobilized Metal Affinity Chromatography (IMAC) with purity higher than 90% (data not shown). GamS protein was stored at −70° C. before application in 100 mM Tris-Acetate buffer (pH 8.2), which also contained 160 mM potassium acetate, 200 mM sodium chloride and 10% sucrose.

Bacterial Strains and Plasmids

SBJY001 is an E. coli K12 derivative optimized for open cell free protein production. SBJY001 was transformed with the plasmid pKD46 (Coli Genetic Stock Center) which contains the phage λ Red recombinase genes under an inducible arabinose promoter.

Construction of SBHS002

SBHS002 is an ompT deletion E. coli strain created using P1 transduction. P1 lysate was made from JW0554-1 (CGSC#8680), a Keio collection strain containing the ompT::Kan$^R$ mutation flanked by FRT sites. The JW0554-1 P1 lysate was then used to introduce the mutation into SBJY001 by P1 transduction. Colonies were grown on LB with 30 μg/ml of kanamycin to select for kanamycin resistance. SBJY001ompT::Kan$^R$ was transformed with the 708-FLPe Cm$^R$ expression plasmid (Gene Bridges). FLP synthesis was induced and colonies were screened for the loss of kanamycin resistance. Kanamycin resistant colonies were sequenced to confirm the deletion of ompT. The ompT deleted strain is referred to as SBHS002.

Cloning and Expression of N-Terminal His-Tagged RF1

RF1 was amplified from E. coli strain A19 genomic DNA using primers 5His-RF1: CATATGCATCACCATCACCAT-CACGGTGGTGGCTCTAAGCCTTCTATCGTTGC-CAAACTGGAAGCC (SEQ ID NO:138) and 3RF1: GTC-GACTTATTCCTGCTCGGACAACGCCGCCAG (SEQ ID NO:139) that introduced an N-terminal His-Tag and NdeI/SalI restriction sites. The insert was ligated into the expression vector pYD317 and confirmed by sequencing. RF1 was expressed in a 25 mL cell free reaction using the plasmid, purified by IMAC, and buffer exchanged into PBS.

Cleavage of Recombinant RF1 Variants Using Cell-Free Extracts

To test if the modified RF1 proteins described herein were cleavable by OmpT, recombinant RF1 variants were incubated with cell extracts with or without OmpT. SBJY001 cells, which have intact ompT protease on the outer membrane, and SBHS002, in which ompT was deleted, were grown up in 5 mL of LB overnight at 37° C. 50 μL of each culture was spun down at 8,000 rpm for 2 minutes and washed twice with 10 mM Tris, 20 mM ammonium chloride and 10 mM magnesium chloride. The cell pellets were then resuspended in 50 uL of the buffer and 10 μg of purified recombinant E. coli RF1 protein was added. The samples were incubated at 37° C. The samples were spun down at 8,000 rpm for 2 minutes. The supernatant containing the RF1 protein was removed and run on a SDS-PAGE gel.

Cell-Free Expression of RF1 Variants

The cell free transcription/translation reactions were carried out in a volume of 60 μl at 30° C. in 24 deep well plates (Cat. No.95040470, Thermo Scientific) for 4.5 hours. The PCR template concentration for RF1 variant expression was 10 μg/ml. The reaction composition also included 8 mM magnesium glutamate, 130 mM potassium glutamate, 35 mM sodium pyruvate, 1.2 mM AMP, 0.86 mM each of GMP, UMP and CMP, 4 mM sodium oxalate, 1 mM putrescine, 1.5 mM spermidine, 15 mM potassium phosphate, 1 mM tyrosine, 2 mM of each 19 other amino acids, 100 nM T7 RNA polymerase, 30% (V/V) S30 cell-extract. To facilitate disulfide formation, S30 cell-extract was treated with 50 μM IAM at room temperature for 30 min before cell-free reaction. A mixture of 2 mM oxidized glutathione (GSSG) and 1 mM reduced glutathione (GSH) was also added with 4.3 μM E. coli disulfide isomerase DsbC. To analyze cell-free expressed RF1 variants with SDS-PAGE and autoradiogram, reactions were performed in the presence of trace amounts of [$^{14}$C]-leucine (300 μCi/mole; GE Life Sciences, N.J.). The RF1 variants were expressed in either an OmpT-positive (OmpT+) cell-extract, which was prepared from bacterial strain SBJY001, or an OmpT-negative (OmpT−) cell-extract, which was prepared from bacterial strain SBHS002 (SBJY001ΔompT). To stabilize PCR templates in the cell-free reaction, 1.4 μM GamS protein was also added to inhibit the activity of RecBCD.

SDS-PAGE and Autoradiography

In order to determine if the modified RF1 proteins were cleavable by OmpT, the RF1 proteins translated in the cell free reactions described above were analyzed by SDS-PAGE and autoradiography. The cell-free reaction samples labeled with $^{14}$C were centrifuged at the maximum speed in a bench top centrifuge and 4 μL of supernatant was mixed with Invitrogen SDS-PAGE sample loading buffer and water. The samples were loaded on 4~12% Bis-Tris SDS-PAGE gels and run with MES running buffer for about 45 minutes. Then the gels were dried and exposed to phosphor screen (63-0034-86, GE healthcare, USA) overnight, and then scanned using Storm 460 (GE healthcare, USA).

Introduction of OmpT Cleavage Sites into RF1

To identify potential OmpT cleavage sites in the RF1 sequence, single Arg or Lys mutations were introduced into different loop regions of RF1 beside an existing Arg or Lys. The loop regions were predicted based on sequence alignment of prokaryotic class I release factors (see Graille, M., Heurgue-Hamard, V., Champ, S., Mora, L., Scrima, N., Ulryck, N., Tilbeurgh, H. and Buckingham, R. H. 2005, Molecular Basis for Bacterial Class I Release Factor Methylation by PrmC. Molecular Cell. 20: 917-927.) To generate the desired variants, the mutation sequences were designed in the middle of the forward and reverse oligo primers (Table 1). In the first step PCR, the 5'-fragment was amplified by PCR using 5chiT2PT7, 5'-GCGTACTAGCGTAC-CACGTGGCTGGTGGCCGATTCATTAATGCAGCTG-GCACGACAGG-3' (SEQ ID NO:53), and the reverse primers (Table 1). The 5'fragment included T7 promoter, the constant region of the N-terminal sequence and the mutation site. The 3'-fragment was also amplified in the first step using forward primers (Table 1) and 3chiT2TT7, 5'-GCG-TACTAGCGTACCACGTGGCTGGTGGCGGT-GAGTTTTCTCCTTCATTACAGAAACGGC-3' (SEQ ID NO:54). The 3' fragment included the mutation site, the constant C-terminal region and T7 terminator sequences. In the second step PCR, the 5'-fragment and 3'-fragment DNA were assembled by overlapping PCR using a single primer 5chiT2,5'-GCGTACTAGCGTACCACGTGGCTGGTGG-3' (SEQ ID NO:55).

First, 9 single mutations, M74R, E76R, E84R, A85R, E87R, E108R, T293R, N296K and S304R, were introduced in the loop regions beside an existing Arg or Lys (Table 2). These RF1 variants and WT RF1 were expressed using PCR templates in cell-free extracts with or without OmpT. The RF1 proteins were analyzed by SDS-PAGE and autoradiography. When expressed in an OmpT negative cell-extract, all 10 RF1 variants showed complete full-length protein on SDS-PAGE. However, when expressed in cell-extracts containing OmpT, variant N296R was partially digested while the other variants migrated as expected for full-length, undigested proteins. N296 is located in the switch loop region of RF1, which is flexible and easy to access by protease digestion.

In the first round screening, N296K was selected for partial digestion by OmpT in cell-extract. In the second round screening, PCR templates of double mutant and triple mutant variants were generated using the same method as described above with primers listed in Table 1. Six double mutants, N296K/L297V, N296K/L297K, N296K/L297R, N296R/L297V, N296R/L297K, N296R/L297R, and 2 triple mutants, N296K/L297R/L298K and N296K/L297R/L298R (Table 2), were tested in cell-free expression with or without OmpT. All eight double and triple RF1 mutant variants were cleaved by OmpT1 (data not shown). Among these variants, N296K/L297R/L298R was most sensitive to digestion by OmpT.

TABLE 1

Forward and reverse primer sequences used in OmpT cleavage site screening

| RF1 Variants | | SEQ ID NO: |
|---|---|---|
| | Forward | |
| WT | GCTCGATGATCCTGAAATGCGTGAGATGGCGCAGG | 56 |
| M74R | GCTCGATGATCCTGAACGCCGTGAGATGGCGCAGG | 57 |
| E76K | CGATGATCCTGAAATGCGTAAGATGGCGCAGGATGAAC | 58 |
| E84K | CAGGATGAACTGCGCAAAGCTAAAGAAAAAAGCGAGCAAC | 59 |
| A85R | CAGGATGAACTGCGCGAACGTAAAGAAAAAAGCGAGCAAC | 60 |
| E87R | GGATGAACTGCGCGAAGCTAAACGTAAAAGCGAGCAACTGGAAC | 61 |
| E108R | GCCAAAAGATCCTGATGACCGTCGTAACGCCTTCCTCG | 62 |
| T293R | CAACAGGCCGAAGCGTCTCGCCGTCGTAACCTGC | 63 |
| N296K | GCGTCTACCCGTCGTAAACTGCTGGGGAGTGGCG | 64 |
| S304K | GGGAGTGGCGATCGCAAGGACCGTAACCGTACTTAC | 65 |
| N296K/L297V | CGAAGCGTCTACCCGTCGTAAAGTTCTGGGGAGTGGCGATCGCAGC | 66 |
| N296K/L297K | CGAAGCGTCTACCCGTCGTAAAAAGCTGGGGAGTGGCGATCGCAGC | 67 |
| N296K/L297R | CGAAGCGTCTACCCGTCGTAAACGTCTGGGGAGTGGCGATCGCAGC | 68 |
| N296R/L297V | CGAAGCGTCTACCCGTCGTCGCGTTCTGGGGAGTGGCGATCGCAGC | 69 |
| N296R/L297K | CGAAGCGTCTACCCGTCGTCGCAAGCTGGGGAGTGGCGATCGCAGC | 70 |
| N296R/L297R | CGAAGCGTCTACCCGTCGTCGCCGTCTGGGGAGTGGCGATCGCAGC | 71 |
| N296K/L297R/L298K | CAGGCCGAAGCGTCTACCCGTCGTAAACGTAAGGGGAGTGGCGATCGCAGCGACC | 72 |
| N296K/L297R/L298R | CAGGCCGAAGCGTCTACCCGTCGTAAACGTCGCGGGAGTGGCGATCGCAGCGACC | 73 |
| | Reverse | |
| WT | CCTGCGCCATCTCACGCATTTCAGGATCATCGAGC | 74 |
| M74R | CCTGCGCCATCTCACGGCGTTCAGGATCATCGAGC | 75 |
| E76K | GTTCATCCTGCGCCATCTTACGCATTTCAGGATCATCG | 76 |
| E84K | GTTGCTCGCTTTTTTCTTTAGCTTTGCGCAGTTCATCCTG | 77 |
| A85R | GTTGCTCGCTTTTTTCTTTACGTTCGCGCAGTTCATCCTG | 78 |
| E87R | GTTCCAGTTGCTCGCTTTTACGTTTAGCTTCGCGCAGTTCATCC | 79 |
| E108R | CGAGGAAGGCGTTACGACGGTCATCAGGATCTTTTGGC | 80 |
| T293R | GCAGGTTACGACGGCGAGACGCTTCGGCCTGTTG | 81 |
| N296K | CGCCACTCCCCAGCAGTTTACGACGGGTAGACGC | 82 |
| S304K | GTAAGTACGGTTACGGTCCTTGCGATCGCCACTCCC | 83 |
| N296K/L297V | GCTGCGATCGCCACTCCCCAGAACTTTACGACGGGTAGACGCTTCG | 84 |
| N296K/L297K | GCTGCGATCGCCACTCCCCAGCTTTTTACGACGGGTAGACGCTTCG | 85 |
| N296K/L297R | GCTGCGATCGCCACTCCCCAGACGTTTACGACGGGTAGACGCTTCG | 86 |

TABLE 1-continued

Forward and reverse primer sequences used in OmpT cleavage site screening

| RF1 Variants | | SEQ ID NO: |
|---|---|---|
| N296R/L297V | GCTGCGATCGCCACTCCCCAG<u>AACGCG</u>ACGACGGGTAGACGCTTCG | 87 |
| N296R/L297K | GCTGCGATCGCCACTCCCCAG<u>CTTGCG</u>ACGACGGGTAGACGCTTCG | 88 |
| N296R/L297R | GCTGCGATCGCCACTCCCCAG<u>ACGGCG</u>ACGACGGGTAGACGCTTCG | 89 |
| N296K/L297R/L298K | GGTCGCTGCGATCGCCACTCCC<u>CTTACGTTT</u>ACGACGGGTAGACGCTTCGGCCTG | 90 |
| N296K/L297R/L298R | GGTCGCTGCGATCGCCACTCCC<u>GCGACGTTT</u>ACGACGGGTAGACGCTTCGGCCTG | 91 |

*Mutation sequences are underlined.

TABLE 2

Single, double and triple substitution variants of RF1

| No. | |
|---|---|
| | Single Substitution Variants |
| A-1 | M74R |
| A-2 | E76K |
| A-3 | E84K |
| A-4 | A85R |
| A-5 | E87R |
| A-6 | E108R |
| A-7 | T293R |
| A-8 | N296K |
| A-9 | S304K |
| | Double Substitution Variants |
| A-11 | N296K/L297V |
| A-12 | N296K/L297K |
| A-13 | N296K/L297R |
| A-14 | N296R/L297V |
| A-15 | N296R/L297K |
| A-16 | N296R/L297R |
| | Triple Substitution Variants |
| A-17 | N296K/L297R/L298K |
| A-18 | N296K/L297R/L298R |

Inserting OmpT Cleavage Peptides into the Switch Loop Region of RF1

In addition to introducing the amino acid mutations described above, RF1 was also modified to replace wild-type sequences in the switch loop region with known OmpT protease-susceptible peptide sequences (see Hwang, B., Varadarajan, N., Li, H., Rodriguez, S., Iverson, B. L. and Georgiou, G. 2007, Substrate Specificity of the *Escherichia coli* Outer Membrane Protease OmpP. *J. Bacteriol.* 189: 522-530; McCarter, J. D., Stephens, D., Shoemaker, K., Rosenberg, S., Kirsch, J. F. and Georgiou, G. 2004, Substrate Specificity of the *Escherichia coli* Outer Membrane Protease OmpT. *J. Bacteriol.* 186: 5919-5925). 22 RF1 variants were constructed, and are listed in Table 3. Variant Nos. 1 to 14 contained ARRG (SEQ ID NO:47) for OmpT digestion. Variant No. 15 contained ARR instead of ARRG (SEQ ID NO:47) since it is at the end of switch loop. Variant No. 16 contained a single mutation N296R. Variant Nos. 17, 18 and 19 contained an OmpT cleavage peptide WLAAR-RGRG (SEQ ID NO:48). Variant Nos. 20, 21 and 22 contained another OmpT cleavage peptide WGGRWARK-KGTI (SEQ ID NO:49).

The mutation sequences were designed in the forward and reverse oligo primers listed in Table 4. In the first step PCR, the 5'-fragment was amplified by PCR using the primer 5chiT2PT7 and the reverse primers (Table 4). The 5'fragment included T7 promoter, the constant region of the N-terminal sequence and the mutation site. The 3'-fragment was also amplified in the first step using forward primers (Table 3) and 3chiT2TT7. The 3' fragment included the mutation site, the constant C-terminal region and T7 terminator sequences. In the second step PCR, the 5'-fragment and 3'-fragment DNA were assembled by overlapping PCR using a single primer 5chiT2 as described above.

22 RF1 variants (Table 3) were expressed using PCR templates in cell-extracts with or without OmpT. Among the ARRG (SEQ ID NO:47) insertion variants, No.9 showed the highest sensitivity to OmpT digestion. Variant Nos. 17, 18 and 19, which contained the OmpT cleavage peptide WLAARRGRG (SEQ ID NO:48), were partially digested by OmpT. However, they were much less sensitive than variant Nos. 20, 21 and 22, which contained the OmpT cleavage peptide WGGRWARKKGTI (SEQ ID NO:49). Variant Nos. 9, 20, 21 and 22 were selected as the most sensitive RF1 variants to OmpT digestion in these 22 constructs.

TABLE 3

OmpT cleavage peptide sequences inserted in the switch loop of RF1

| No, | Peptide** | SEQ ID NO: |
|---|---|---|
| *0 | QQAEASTRRNLLGSGDRS | 4 |
| 1 | Q<u>ARRG</u>STRRNLLGSGDRS | 26 |
| 2 | QQ<u>ARRG</u>TRRNLLGSGDRS | 27 |
| 3 | QQA<u>ARRG</u>RRNLLGSGDRS | 28 |
| 4 | QQAE<u>ARRG</u>RNLLGSGDRS | 29 |
| 5 | QQAEA<u>ARRG</u>NLLGSGDRS | 30 |
| 6 | QQAEAS<u>ARRG</u>LLGSGDRS | 31 |
| 7 | QQAEAST<u>ARRG</u>LGSGDRS | 32 |
| 8 | QQAEASTR<u>ARRG</u>GSGDRS | 33 |
| 9 | QQAEASTRR<u>ARRG</u>GSGDRS | 34 |
| 10 | QQAEASTRRN<u>ARRG</u>GDRS | 35 |

TABLE 3-continued

OmpT cleavage peptide sequences inserted in the switch loop of RF1

| No, | Peptide** | SEQ ID NO: |
|---|---|---|
| 11 | QQAEASTRRNLARRGDRS | 36 |
| 12 | QQAEASTRRNLLARRGRS | 37 |
| 13 | QQAEASTRRNLLGARRGS | 38 |
| 14 | QQAEASTRRNLLGSARRG | 39 |
| 15 | QQAEASTRRNLLGSGARR | 40 |
| 16 | QQAEASTRRRLLGSGDRS | 6 |
| 17 | QQAWLAARRGRGGSGDRS | 41 |
| 18 | QQAEWLAARRGRGSGDRS | 42 |
| 19 | QQAEAWLAARRGRGGDRS | 43 |
| 20 | QQWGGRWARKKGTIGDRS | 44 |
| 21 | QQAWGGRWARKKGTIDRS | 45 |
| 22 | QQAEWGGRWARKKGTIRS | 46 |

*WT switch loop peptide sequence (Q287 to S304)
**The inserted amino acid or peptide sequences are underlined

TABLE 4

Forward and reverse primer sequences for OmpT cleavage peptide insertion

| No. | | SEQ ID NO: |
|---|---|---|
| | Forward | |
| 0 | GCCGAAGCGTCTACCCGTCGTAACCTGCTGGGGAGTGGCGATCGCAGCGACCGTAACCGTACTTACAACTTCCCG | 92 |
| 1 | CGCCGTGGTTCTACCCGTCGTAACCTGCTGGGGAGTGGCGATCGCAGCGACCGTAACCGTACTTACAACTTCCCG | 93 |
| 2 | GCACGCCGTGGTACCCGTCGTAACCTGCTGGGGAGTGGCGATCGCAGCGACCGTAACCGTACTTACAACTTCCCG | 94 |
| 3 | GCCGCACGCCGTGGTCGTCGTAACCTGCTGGGGAGTGGCGATCGCAGCGACCGTAACCGTACTTACAACTTCCCG | 95 |
| 4 | GCCGAAGCACGCCGTGGTCGTAACCTGCTGGGGAGTGGCGATCGCAGCGACCGTAACCGTACTTACAACTTCCCG | 96 |
| 5 | GCCGAAGCGGCACGCCGTGGTAACCTGCTGGGGAGTGGCGATCGCAGCGACCGTAACCGTACTTACAACTTCCCG | 97 |
| 6 | GCCGAAGCGTCTGCACGCCGTGGTCTGCTGGGGAGTGGCGATCGCAGCGACCGTAACCGTACTTACAACTTCCCG | 98 |
| 7 | GCCGAAGCGTCTACCGCACGCCGTGGTCTGGGGAGTGGCGATCGCAGCGACCGTAACCGTACTTACAACTTCCCG | 99 |
| 8 | GCCGAAGCGTCTACCCGTGCACGCCGTGGTGGGAGTGGCGATCGCAGCGACCGTAACCGTACTTACAACTTCCCG | 100 |
| 9 | GCCGAAGCGTCTACCCGTCGTGCACGCCGTGGTAGTGGCGATCGCAGCGACCGTAACCGTACTTACAACTTCCCG | 101 |
| 10 | GCCGAAGCGTCTACCCGTCGTAACGCACGCCGTGGTGGCGATCGCAGCGACCGTAACCGTACTTACAACTTCCCG | 102 |
| 11 | GCCGAAGCGTCTACCCGTCGTAACCTGGCACGCCGTGGTGATCGCAGCGACCGTAACCGTACTTACAACTTCCCG | 103 |
| 12 | GCCGAAGCGTCTACCCGTCGTAACCTGCTGGCACGCCGTGGTCGCAGCGACCGTAACCGTACTTACAACTTCCCG | 104 |
| 13 | GCCGAAGCGTCTACCCGTCGTAACCTGCTGGGGGCACGCCGTGGTAGCGACCGTAACCGTACTTACAACTTCCCG | 105 |
| 14 | GCCGAAGCGTCTACCCGTCGTAACCTGCTGGGGAGTGCACGCCGTGGTGACCGTAACCGTACTTACAACTTCCCG | 106 |
| 15 | GCCGAAGCGTCTACCCGTCGTAACCTGCTGGGGAGTGGCGCACGCCGTGACCGTAACCGTACTTACAACTTCCCG | 107 |

TABLE 4-continued

Forward and reverse primer sequences for OmpT cleavage peptide insertion

| No. | | SEQ ID NO: |
|---|---|---|
| | CCCG | |
| 16 | GCCGAAGCGTCTACCCGTCGT<u>CGT</u>CTGCTGGGGAGTGGCGATCGCAGCGACCGTAACCGTACTTACAACTTCCCG | 108 |
| 17 | GCC<u>TGGCTGGCAGCGCGTCGCGGTCGTGGC</u>GGGAGTGGCGATCGCAGCGACCGTAACCGTACTTACAACTCCCG | 109 |
| 18 | GCCGAA<u>TGGCTGGCAGCGCGTCGCGGTCGTGGC</u>AGTGGCGATCGCAGCGACCGTAACCGTACTTACAACTCCCG | 110 |
| 19 | GCCGAAGCG<u>TGGCTGGCAGCGCGTCGCGGTCGTGGC</u>GGCGATCGCAGCGACCGTAACCGTACTTACAACTCCCG | 111 |
| 20 | <u>TGGGGTGGCCGTTGGGCTCGCAAGAAAGGTACTATT</u>GGCGATCGCAGCGACCGTAACCGTACTTACAACTCCCG | 112 |
| 21 | GCC<u>TGGGGTGGCCGTTGGGCTCGCAAGAAAGGTACTATT</u>GATCGCAGCGACCGTAACCGTACTTACAACTTCCCG | 113 |
| 22 | GCCGAA<u>TGGGGTGGCCGTTGGGCTCGCAAGAAAGGTACTATT</u>CGCAGCGACCGTAACCGTACTTACAACTTCCCG | 114 |
| | Reverse | |
| 0 | GCTGCGATCGCCACTCCCCAGCAGGTTACGACGGGTAGACGCTTCGGCCTGTTGGCGTTTTGCCATTTCAGCAGC | 115 |
| 1 | GCTGCGATCGCCACTCCCCAGCAGGTTACGACGGGTAGA<u>ACCACGGCGTGC</u>TTGGCGTTTTGCCATTTCAGCAGC | 116 |
| 2 | GCTGCGATCGCCACTCCCCAGCAGGTTACGACGGGT<u>ACCACGGCGTGC</u>CTGTTGGCGTTTTGCCATTTCAGCAGC | 117 |
| 3 | GCTGCGATCGCCACTCCCCAGCAGGTTACGACG<u>ACCACGGCGTGC</u>GGCCTGTTGGCGTTTTGCCATTTCAGCAGC | 118 |
| 4 | GCTGCGATCGCCACTCCCCAGCAGGTTACG<u>ACCACGGCGTGC</u>TTCGGCCTGTTGGCGTTTTGCCATTTCAGCAGC | 119 |
| 5 | GCTGCGATCGCCACTCCCCAGCAGGTT<u>ACCACGGCGTGC</u>CGCTTCGGCCTGTTGGCGTTTTGCCATTTCAGCAGC | 120 |
| 6 | GCTGCGATCGCCACTCCCCAGCAG<u>ACCACGGCGTGC</u>AGACGCTTCGGCCTGTTGGCGTTTTGCCATTTCAGCAGC | 121 |
| 7 | GCTGCGATCGCCACTCCCCAG<u>ACCACGGCGTGC</u>GGTAGACGCTTCGGCCTGTTGGCGTTTTGCCATTTCAGCAGC | 122 |
| 8 | GCTGCGATCGCCACTCCC<u>ACCACGGCGTGC</u>ACGGGTAGACGCTTCGGCCTGTTGGCGTTTTGCCATTTCAGCAGC | 123 |
| 9 | GCTGCGATCGCCACT<u>ACCACGGCGTGC</u>ACGACGGGTAGACGCTTCGGCCTGTTGGCGTTTTGCCATTTCAGCAGC | 124 |
| 10 | GCTGCGATCGCC<u>ACCACGGCGTGC</u>GTTACGACGGGTAGACGCTTCGGCCTGTTGGCGTTTTGCCATTTCAGCAGC | 125 |
| 11 | GCTGCGATC<u>ACCACGGCGTGC</u>CAGGTTACGACGGGTAGACGCTTCGGCCTGTTGGCGTTTTGCCATTTCAGCAGC | 126 |
| 12 | GCTGCG<u>ACCACGGCGTGC</u>CAGCAGGTTACGACGGGTAGACGCTTCGGCCTGTTGGCGTTTTGCCATTTCAGCAGC | 127 |
| 13 | GCT<u>ACCACGGCGTGC</u>CCCAGCAGGTTACGACGGGTAGACGCTTCGGCCTGTTGGCGTTTTGCCATTTCAGCAGC | 128 |
| 14 | <u>ACCACGGCGTGC</u>ACTCCCCAGCAGGTTACGACGGGTAGACGCTTCGGCCTGTTGGCGTTTTGCCATTTCAGCAGC | 129 |
| 15 | <u>ACGGCGTGC</u>GCCACTCCCCAGCAGGTTACGACGGGTAGACGCTTCGGCCTGTTGGCGTTTTGCCATTTCAGCAGC | 130 |
| 16 | GCTGCGATCGCCACTCCCCAGCAG<u>ACG</u>ACGACGGGTAGACGCTTCGGCCTGTTGGCGTTTTGCCATTTCAG | 131 |

TABLE 4-continued

Forward and reverse primer sequences for OmpT cleavage peptide insertion

| No. | | SEQ ID NO: |
|---|---|---|
| | CAGC | |
| 17 | GCTGCGATCGCCACTCCCGCCACGACCGCGACGCGCTGCCAGCCAGGCCTGTTGGCGTTTTGCCATTTCAGCAGC | 132 |
| 18 | GCTGCGATCGCCACTGCCACGACCGCGACGCGCTGCCAGCCATTCGGCCTGTTGGCGTTTTGCCATTTCAGCAGC | 133 |
| 19 | GCTGCGATCGCCGCCACGACCGCGACGCGCTGCCAGCCACGCTTCGGCCTGTTGGCGTTTTGCCATTTCAGCAGC | 134 |
| 20 | GCTGCGATCGCCAATAGTACCTTTCTTGCGAGCCCAACGGCCACCCCACTGTTGGCGTTTTGCCATTTCAGCAGC | 135 |
| 21 | GCTGCGATCAATAGTACCTTTCTTGCGAGCCCAACGGCCACCCCAGGCCTGTTGGCGTTTTGCCATTTCAGCAGC | 136 |
| 22 | GCTGCGAATAGTACCTTTCTTGCGAGCCCAACGGCCACCCCATTCGGCCTGTTGGCGTTTTGCCATTTCAGCAGC | 137 |

*Mutation sequences are underlined.

Example 2

Having demonstrated that RF1 was successfully modified to be cleavable by OmpT1 protease, this example describes the construction of recombinant bacterial strains that express both modified RF1 and intact OmpT1. The purpose of this example is to show that RF1 variants expressed by the recombinant strains are cleaved in cell-free extracts from the recombinant strains that express OmpT1.

Oligonucleotide-Mediated Allelic Replacement

In order to generate bacterial strains that express the modified RF1 proteins described herein, oligonucleotide-mediated allelic replacement (OMAR) was used to insert the RF1 mutations into the bacterial genome. The OMAR protocol was adapted from a previously reported protocol (Wang and Church, *Methods in Enzymology*, 2011, 498, 409-426). Briefly, SBJY001 containing the pKD46 plasmid were grown in 3 ml LB and 50 µg/mL ampicillin at 30° C. to $OD_{600}$ 0.3. The cells were then induced with 1 mM L-arabinose at 37° C. for 45 min. The cell pellet was washed 2× with cold 10% glycerol and resuspended in 30 µL cold 10% glycerol. 5 µM of each oligo was added to the resuspended cells. Synthetic oligos (Integrated DNA Technologies) were 90 base pairs long and designed to anneal to the lagging strand during DNA replication (see Table 5). The cells were electroporated at 1800V for 5 ms in a 1 mm cuvette. They were then recovered in 3 mL LB and 50 µg/ml Amp. This process was repeated for 13 cycles. Cells were diluted and plated on LB agar plates and grown at 37° C. overnight.

MAMA PCR to Identify Bacterial Strains with the Desired Mutations

Bacterial colonies were screened using an adaptation of Mismatch Amplification Mutation Assay (MAMA) PCR to identify strains with the desired mutations in RF1 (Cha et. Al, *PCR Methods and Applications*, 1992, 2, 14-20). Briefly, a universal 5' primer was used in conjunction with a 3' primer that was specific for each mutation to differentiate between a mutant and a WT colony (see Table 5). The oligos were ordered from Eurofins MWG Operon. Platinum® Blue PCR Supermix (Invitrogen) was used to run the MAMA PCR. The PCR was run at 95° C. 3 min, 30× (95° C. 15 sec, 58° C. 20 sec, 72° C. 1 min) and 72° C. 5 min. The PCR products were run on a 96 well E-gel (Invitrogen) to visualize any bands.

Extract Preparation and Western Blot

Strains SBHS015, SBHS016 and SBHS017, that were engineered to contain modified RF1 variants, were grown up in 500 mL TB at 37° C. shaking overnight in Tunair shake flasks. The cells were pelleted at 6000×g for 15 minutes. The cell pellet was washed 2× with 6 mL S30 Buffer (10 mM Tris, 14 mM magnesium acetate and 60 mM potassium acetate): 1 g cell pellet. The cells were then resuspended in 2 mL S30 Buffer: 1 g cell pellet. The resuspended cells were lysed using a homogenizer. The extract was then clarified 2× at 15,000×g for 30 minutes. The extract was activated for 1, 2 or 3 hrs in a 30° C. water bath. An anti-RF1 antibody was made by inoculating rabbits with purified recombinant *E. coli* RF1 protein that was then purified using an affinity matrix (YenZym Antibodies LLC). The specificity of the antibody was confirmed using ELISAs and Western Blots of the recombinant protein. The cell pellet, lysate and extract samples were run on a SDS-PAGE gel and transferred to a PVDF membrane using the iBlot® system (Invitrogen). The primary anti-RF1 antibody was used followed by a secondary anti-rabbit alkaline-phosphatase conjugated antibody (Invitrogen). The bands were visualized using an alkaline-phosphatase chromogenic substrate solution containing 5-bromo-4-chloro-3-indolyl-1-phosphate and nitroblue tetrazolium (Invitrogen).

TABLE 5

Sequences of oligonucleotides for OMAR and MAMA PCR.

| Oligo name | Oligo Sequence (5' to 3') | SEQ ID NO: |
|---|---|---|
| 1opRF1 KR (OMAR) | GGGAAGTTGTAAGTACGGTTACGGTCGCTGCGATCcCCtgaaCCaAGac GcTTtCGACGGGTAGACGCTTCGGCCTGTTGGCGTTTTGCC | 140 |
| 1opRF1 KRR (OMAR) | GGGAAGTTGTAAGTACGGTTACGGTCGCTGCGATCcCCtgaaCCacgacG cTTtCGACGGGTAGACGCTTCGGCCTGTTGGCGTTTTGCC | 141 |
| 1opRF1 KRK (OMAR) | GGGAAGTTGTAAGTACGGTTACGGTCGCTGCGATCcCCtgaaCCottacG cTTtCGACGGGTAGACGCTTCGGCCTGTTGGCGTTTTGCC | 142 |
| 3KR op-PCR (MAMA) | GCG ATC CCC TGA ACC AAG ACG C | 143 |
| 3 KRR op-PCR (MAMA) | CGATCcCCtgaaCCacgacGc | 144 |
| 3 KRK op-PCR (MAMA) | TGCGATCcCCtgaaCCcttacGc | 145 |
| 5 RF1 op-PCR (MAMA) | CGTGACGGGGATAACGAACGCC | 146 |

Three recombinant bacterial strains were identified that successfully incorporated mutations of RF1 into their genomes. Strain SBHS015 contains the N296K/L297R double mutation variant of RF1, referred to as variant A13. Strain SBHS016 contains the N296K/L297R/L298R triple mutation variant of RF1, referred to as variant A18. Strain SBHS017 contains the N296K/L297R/L298K triple mutation variant of RF1, referred to as variant A17. All three strains also express intact OmpT1, as they are derived from the parent strain SBJY001. When the recombinant strains were lysed and incubated for various time periods (0, 1, 2 and 3 hours), the modified RF1 protein variants were efficiently cleaved at all time points tested by the cell-free extract, as determined by Western blot analysis (data not shown). In contrast, cleavage of unmodified, wild-type RF1 by strain SBJY001 was not detected over the same time periods, indicating that wild-type RF1 is not efficiently cleaved in cell-free extracts containing intact OmpT1.

This example demonstrates that recombinant bacterial strains were engineered to express modified RF1 variants, and that the RF1 variants were cleaved by cell-free extracts from OmpT1 positive strains.

EXAMPLE 3

Example 3 demonstrates that intact RF1 proteins modified to include OmpT1 cleavage sites in the switch loop region have wild-type RF1 function.
Functional Test of Recombinant RF1 Variants In order to test the function of the recombinant RF1 variants described herein, the ability of the RF1 variants to terminate translation at an amber codon was determined. An Fc protein with a TAG mutation was expressed in the presence of 500 nM of purified recombinant E. coli wild-type or mutant RF1 and 2 µM non-natural amino acid in SBHS002 extract (an OmpT deleted strain). The 60 µL cell free reactions were run at 30° C. for 5 hrs in the presence of $^{14}$C-Leu. The final reactions were centrifuged to obtain the soluble fraction, run on a reducing SDS-PAGE gel, transferred to a PVDF membrane (Invitrogen), and exposed to a phosphoscreen overnight. The phosphoscreen was visualized using a Storm Imager and ImageQuant was used to determine the relative band intensities. Relative activities of mutants were determined by comparing the amount of truncated Fc protein to the negative control (no exogenous RF1 added) and the positive control (WT RF1 added). The percent truncated protein was determined using the equation: (truncated protein counts/total protein counts)×100%. Relative RF1 activity was determined using the equation: [(variant truncated protein−negative control truncated protein)/(WT RF1 truncated protein−negative control truncated protein)]×100%.

As shown in FIG. 1, RF1 variants described herein have RF1 activity, as demonstrated by truncation of translation when incorporating a non-native amino acid (pAzF) at an amber codon introduced at position S378 of the Fc protein. In particular, the RF1 variant A13 (having N296K/L297R substitutions) possessed similar activity levels as wild-type RF1.

This example demonstrates that intact RF1 proteins modified to include OmpT cleavage sites in the switch loop region have functional RF1 activity (e.g., reduced amber suppression).

Example 4

Example 4 demonstrates increased incorporation of non-natural amino acids into the IgG heavy chain of Herceptin protein using cell free extracts comprising RF1 variants having OmpT1 cleavage sites in the switch loop region. The cell free extracts are from the bacterial strains described in Example 2.
Methods
Site Directed Mutagenesis of Herceptin Heavy Chain To introduce a nnAA into the heavy chain of Herceptin, the DNA template encoding Herceptin was mutated to introduce amber codons at different positions of the coding sequence. Site directed mutagenesis was performed using a pYD plasmid containing the coding region of Herceptin6× His at the C-terminus as the DNA template and synthetic oligonucleotides (Operon) containing amber codons in both sense and antisense directions (Table 6). Oligonucleotides of each mutation were mixed with the DNA template and Phusion® polymerase (Thermo, Cat# F531s) to a final volume of 20 µL. The final concentration of each component was 0.16 µM of each oligonucleotide, 0.5 ng/µL template DNA, 0.02 U/µL Phusion® polymerase in HF buffer (Thermo) containing 1.5 mM MgCl$_2$ and 200 µM dNTP. Mixture was incubated at 98° C. 5 m, 18 PCR cycles (98° C. 30 s, 55° C. 1 m, 72° C. 4 m), 10 m at 72° C. and stored at 4° C. for up to 16 h. DpnI (NEB) was added to the mixture to final concentration of 0.6 U/µL and incubated for 37° C. 1 h. 5 µL of each mixture was transformed into 50 µL of Chemically Competent E. coli cells according to manufactures procedure (Invitrogen, MultiShot™ 96-Well Plate TOP10). Transformed cells were recovered in 200 µL SOC (Invitrogen) 37° C. 1 h and plated onto Luria-Bertani (LB) agar supplemented with 50 µg/mL kanamycin (Teknova). After 24 h at 37° C., colonies were picked using Qpix2 (Genetix) into 200 µL LB with 7.5% glycerol and 50 µg/mL kanamycin, and grown at 37° C. for 24 h, 20 µL of culture was used for rolling circle amplification and sequenced by primer extension using T7 (5'-TAATACGACTCAC-TATAGG-3'; SEQ ID NO:147) and T7 term (5'-GCTAGT-TATTGCTCAGCG-3'; SEQ ID NO:148) primers (Sequetech). Sequence was analyzed by Sequencher (Gene Codes).

TABLE 6

Primers for introducing amber codons at the indicated positions of Herceptin.

| Variant | Sense Oligo (SEQ ID NO:) | Antisense Oligo (SEQ ID NO:) |
|---|---|---|
| SP-00067_V422 | CGTTGGCAGCAGGGTAATTAGTTCAGCTGCAGCGTTATG (149) | CATAACGCTGCAGCTGAACTAATTACCCTGCTGCCAACG (150) |
| SP-00127_S415 | GCAAGCTGACCGTCGATAAATAGCGTTGGCAGCAGGGTAATG (151) | CATTACCCTGCTGCCAACGCTATTTATCGACGGTCAGCTTGC (152) |
| SP-00128_Q418 | CGATAAAAGCCGTTGGTAGCAGGGTAATGTGTTCAG (153) | CTGAACACATTACCCTGCTACCAACGGCTTTTATCG (154) |
| SP-00114_P343 | GCAAAGCGAAAGGCCAATAGCGTGAACCGCAGGTC (155) | GACCTGCGGTTCACGCTATTGGCCTTTCGCTTTGC (156) |
| SP-00112_G341 | GACGATCAGCAAAGCGAAATAGCAACCGCGTGAACCGCAG (157) | CTGCGGTTCACGCGGTTGCTATTTCGCTTTGCTGATCGTC (158) |
| SP-00102_K320 | GCTGAATGGTAAAGAATACTAGTGCAAAGTGAGCAACAAGG (159) | CCTTGTTGCTCACTTTGCACTAGTATTCTTTACCATTCAGC (160) |
| SP-00066_F404 | CTGGACAGCGACGGTAGCTAGTTTCTGTATAGCAAGCTG (161) | CAGCTTGCTATACAGAAACTAGCTACCGTCGCTGTCCAG (162) |
| SP-00113_Q342 | GCAAAGCGAAAGGCTAGCCGCGTGAACCGCAG (163) | CTGCGGTTCACGCGGCTAGCCTTTCGCTTTGC (164) |
| SP-00096_T299 | GTGAGGAACAATACAATAGCTAGTATCGCGTAGTGAGCGTGC (165) | GCACGCTCACTACGCGATACTAGCTATTGTATTGTTCCTCAC (166) |
| SP-00120_Y373 | GGTGAAGGGCTTTTAGCCGAGCGACATCGC (167) | GCGATGTCGCTCGGCTAAAAGCCCTTCACC (168) |
| SP-00094_N297 | CGCGTGAGGAACAATACTAGAGCACGTATCGCGTAGTG (169) | CACTACGCGATACGTGCTCTAGTATTGTTCCTCACGCG (170) |
| SP-00125_F405 | GACAGCGACGGTAGCTTCTAGCTGTATAGCAAGCTGAC (171) | GTCAGCTTGCTATACAGCTAGAAGCTACCGTCGCTGTC (172) |

Extract Preparation

E. coli strain SBHS016 with modified RF1 variant A18 was harvested at a final density of 40-55 OD, and centrifuged at 14,000 g in a Sharples Model AS14 centrifuge for 10 minutes to remove spent medium. The cell paste was re-suspended to homogeneity with a ratio of 6 mL/g cells S30 buffer (14 mM MgAcO, 60 mM KAcO, 10 mM Tris), and centrifuged again at 14,000 g for 10 minutes using the Sharples AS14 for further removal of spent medium. The resulting clarified cell paste was re-suspended in S30 with a ratio of 2 mL/g cells, and the cells were lysed by single pass through an Avestin Emulsiflex C-55 homogenizer at 17,000 psi. The homogenate is clarified by centrifugation at 14,000 g twice for 30 minutes each, and the resulting pellets were discarded. The resultant cell extract solution was incubated at 30° C. for 2 hours, and then centrifuged again at 14,000 g using the Sharples AS14 for particulate removal. This final solution was frozen in $LN_2$ and stored at −80° C. until needed for cell-free protein synthesis.

Cell-free extracts were thawed to room temperature and incubated with 50 uM iodoacetamide for 30 min. Cell-free reactions were run at 30 C for up to 10 h containing 30% (v/v) iodoacetamide-treated extract with 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (1 mM for tyrosine), 4 mM sodium oxalate, 1 mM putrescine, 1.5 mM spermidine, 15 mM potassium phosphate,100 nM T7 RNAP, 2.5 uM E. coli DsbC, 5 uM yeast PDI, 2 mM oxidized (GSSG) glutathione and 15 uM yeast tRNA pN3F aminoacyl tRNA. To label synthesized protein with $^{14}C$, 3.33% (v/v) 1-[U-$^{14}C$]-leucine (300 mCi/mmole; GE Life Sciences, Piscataway, N.J.) was added to reaction as well. The concentrations of heavy chain TAG variant plasmid and wild type light chain plasmid were 7.5 ug/mL and 2.5 ug/mL respectively. As control, the cell-free expression of wild type light chain was done in parallel with TAG variants.

12 difficult to suppress sites were selected from heavy chain based on our internal study, including N297, T299, K320, G341, Q342, P343, Y373, F404, F405, S415, Q418, and V422. S136 was chosen as positive control, which has relatively high suppression. Two cell extracts, from strains SBJY001 (which expresses wild-type RF1) and SBHS016 (which expresses modified RF1), were used to compare the capability of the extracts to incorporate nnAA into these difficult to suppress sites.

60 uL cell-free reactions were run in 24 well plates. After the cell-free reactions were completed, TCA precipitation was performed to measure total and soluble proteins synthesized. In parallel, non reducing and reducing gels were for autoradiography assay. For non reducing gel, 4 uL of sample, 8 uL of DI $H_2O$ and 4 uL of 4× LDS buffer (Invitrogen, Carlsbad, Calif.) were mixed before being loaded on gel. For reducing gel, 4 uL of sample, 1 uL of 1 M DTT, 7 uL of DI $H_2O$ and 4 uL of 4× LDS buffer (Invitrogen, Carlsbad, Calif.) were mixed and heated in hot blot at 70 C for 5 minutes. Samples were analyzed by 4~12% Bis-Tris SDS-PAGE gels (Invitrogen, Carlsbad, Calif.) according to the manufacturer's recommendations. Gels were dried and analyzed by autoradiography using a Storm 840 PhosphoImager after about 16 hours exposure.

$$IgG\ yield = \frac{IgG\ \text{full length band intensity from non reducing gel}}{\text{the sum of all bands intensity from reducing gel} \times [\text{soluble protein}]}$$

where the band intensity is determined by ImageQuant™ software and the [soluble protein] was estimated by TCA precipitation method.

The suppressions of amber codon at different sites of heavy chain were determined by [$^{14}C$]-autoradiograhy of reducing SDS-AGE gels. Full length wild type heavy chain and suppressed heavy chain TAG variants run at 49 Kd on SDS-PAGE. Non suppressed (truncated) heavy chain of TAG variants run at a lower molecular weight.

The suppression of TAG in heavy chain is predicted by:

$$\text{suppression} = \frac{\text{band intensity of suppressed heavy chain } TAG \text{ variant}}{\text{band intensity of wild type heavy chain}}$$

where the band intensity is determined by ImageQuant™ software.

To generate materials for purification, the reactions were scaled up to 1 mL in 10 cm petri dishes under the same condition.

Production of tRNA

Transcriptions of all $tRNA^{phe}_{CUA}$ transcripts were done under the following conditions: 20-50 ng/µl pYD318-tRNAphe AAA-HDV-T7trm, 40 mM NaCl, 10 mM $MgCl_2$, 10 mM DTT, 4 mM dNTPs, 2.5 mM spermidine, 1 U/ml PPiase, 2.5 mg/ml T7 RNA polymerase, and 40 mM Tris (pH 7.9). tRNA molecules were separated from parental RNA and HDV ribozyme RNA product by gel filtration chromatography using a tandem Sephacryl 100 or 300 resin in XK50/100 columns. Sizing columns were developed in 50 mM Tris (pH 6.5) and 250 mM NaCl. Fractions containing tRNA were pooled, mixed with 1/10 volume of 3 M sodium acetate (pH 5.2), and an equal volume of isopropanol was added to precipitate the RNA. tRNA was stored as a pellet or resuspended in 10 mM Tris (pH 6.5) and 0.1 mM EDTA.

tRNAs for use in aminoacylation reactions are treated with T4 polynucleotide kinase in 100 mM MES pH 5.5, 10 mM $MgCl_2$ and 10 mM 2-mercaptoethanol for 1 hr to remove the 2',3'-cyclic phosphate leaving 2',3'-OH groups at the 3' terminus of the tRNA. T4 PNK treated tRNA was phenol:chloroform:isoamylalcohol extracted and buffer exchanged using a G25 column which removed inorganic phosphate and excess phenol. tRNA was isopropanol or ethanol precipitated, resuspended in 10 mM Tris (pH 6.5) and 0.1 mM EDTA. The tRNA was refolded by heating the tRNA to 70° C. for 20 minutes. Then 10 mM $MgCl_2$ was added and the mixture was slowly equilibrated to room temperature.

HDV ribozyme cleavage of tRNA transcripts, while producing homogenous 3' ends, leaves a 2'-3' cyclic phosphate moiety that interferes with subsequent aminoacylation. It has been found that this can be removed using T4 polynucleotide kinase (PNK). 40 µM tRNA was incubated at 37° C. with 0.050 mg/ml PNK in 50 mM MES (pH 5.5), 10 mM $MgCl_2$, 300 mM NaCl, and 0.1 mM EDTA. Dephosphorylation was assayed by two different methods. Dephosphoryation was confirmed using denaturing gel electrophoresis. As has been reported, dephophoylated tRNA has a reduced mobility in acid/urea gels electrophoresis. Aliquots containing 3 µg of dephosphorylated tRNA were diluted 2-fold in loading buffer (100 mM sodium acetate (pH 5.2), 7 M urea, 1 mg/ml bromophenol blue dye) and loaded on a 6.5% 19:1 acrylamide, 100 mM sodium acetate (pH 5.2), 7 M urea gel (40 cm×34 cm) and electrophoresed overnight at 40 W. Gels were stained using 0.06% Methylene Blue, 0.5 M sodium acetate (pH 5.2) for 30 minutes and destained with deionized water. Both assays indicated significant dephosphorylation after only 5 minutes. Dephosphorylation was essentially complete after 1 hour tRNA was refolded by heating to 70° C., addition of 10 mM $MgCl_2$, and then slowly cooled to room temperature. RNA concentration was measured using a Nano-Drop 1000 spectrophotometer (Thermo Scientific) and confirmed by gel electrophoresis.

Amber Suppressor tRNA Aminoacylation

The conditions for non-natural aminoacylation are 50 mM HEPES pH 8.1, 40 mM KCl, 75 mM MgCl$_2$, 5 mM ATP, 8-40 µM tRNA$^{phe}_{CUA}$, 10 mM DTT, 2 mM amino acid (pN$_3$F), and 40 µM PheRS T415A D243A. Determination of the percent aminoacylation of tRNA$^{phe}_{CUA}$ is accomplished by HPLC HIC resolution of the aminoacylated and unaminoacylated moieties of tRNA. This method allows us to monitor the extent of aminoacylation of our tRNA after is has been processed and is ready to be used for incorporation into proteins. Reactions are incubated at 37° C. for 15 min and quenched with 2.5 volumes of 300 mM sodium acetate pH 5.5. The quenched sample is extracted with 25:24:1 phenol:chloroform:isoamyl alcohol pH 5.2 (ambion) and vortexed for 2 min. These are then centrifuged at 14,000 rcf for 10-30 min at 4° C. to separate the aqueous (tRNA) and organic phases (protein). The aqueous phase (containing tRNA) is removed and added to a pre-equilibrated (300 mM NaOAC) G25 sephadex resin size exclusion column that separates based on the size of the molecule. The elutant is mixed with 2.5 volumes of 100% ethanol and incubated at −80° C. for 15-30 minutes and centrifuged at 12,000-14,000 rcf for 30-45 minutes. The aminoacylated tRNA is now in a pellet that can be stored at −80° C. or resuspended in a slightly acidic buffer for injection into the HPLC and/or use in OCFS reactions.

The HPLC C5 HIC column is equilibrated in buffer A (50 mM potassium phosphate and 1.5 M ammonium sulfate pH 5.7) until the UV trace doesn't fluctuate from zero. 1-10 µg tRNA is mixed with 100 µl of 2× buffer A (100 mM potassium phosphate and 3 M ammonium sulfate). The sample is injected and run in a gradient from buffer A to buffer B (50 mM potassium phosphate and 5% isopropanol) over 50 minutes.

Incorporation of pN$_3$F into turboGFP TAG Mutants:

To monitor fluorescence of Green Fluorescent protein in a construct where there is an amber codon (stop codon), the DNA encoding turboGFP (Evrogen, Russia) was cloned into our OCFS expression vector pYD317. A stop codon (TAG) was inserted by overlapping PCR mutagenesis at the nucleotides corresponding to the amino acid Lysine 37, Tyrosine 50, and Glutamate 205 (and combinations) according to the crystal structure of turboGFP (pdb 2G6X). Therefore any suppression of the stop codon with a charged tRNA will result in fluorescence. Reactions were incubated at 30° C. in a spectrophotometer (Molecular Devices, SpectraMaxM5) for five hours with an adhesive cover (VWR, 9503130) and fluorescence intensity measured at 10-minute intervals, $\lambda_{Ex}$=476 nm and $\lambda_{Em}$=510. OCFS reaction mix was immediately added to microplate with inhibitor for a 25 µL final reaction volume containing 30% S30 extract, 24 ug/mL T7 RNA polymerase, 1 mM L-tyrosine (Sigma, T8566), premix*, 10-60 µM pN$_3$F-tRNA$^{phe}_{CUA}$ or uncharged tRNA$^{phe}_{CUA}$, and 3 nM turboGFP plasmid in DEPC-treated water (G Biosciences, 786-109). A positive control reaction using turboGFP without the stop codon was used to ensure that the reactions proceeded with rates similar previously observed, while reactions containing turboGFP Y50TAG were also run without tRNA to ensure no fluorescence was detected (negative control). Suppression efficiencies were calculated by comparison of positive control fluorescence to the amber codon containing template fluorescence.

Figure 2:
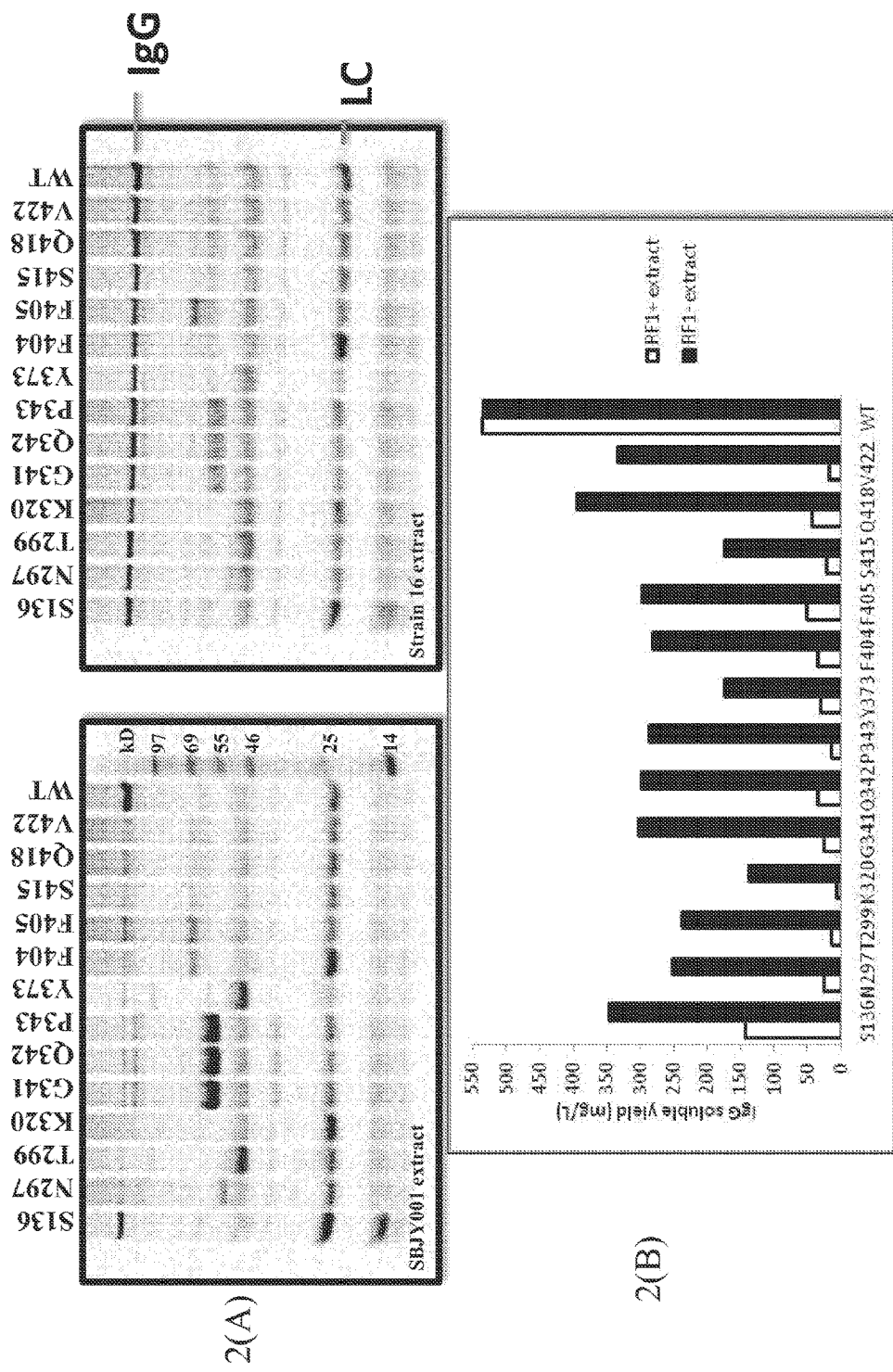
FIG. 2 shows that cell-free extracts from a bacterial strain engineered to express a modified RF1 variant (A18) produce a substantial increase in the yield of full-length IgG when nnAA were introduced at various positions of heavy chain, as compared to a bacterial strain expressing a wild-type RF1. 2(A) left panel: SBJY001 extract, containing intact OmpT and wild-type RF1. 2(A) right panel: SBHS016 extract (strain 16), containing intact OmpT and RF1 variant A18. The band intensity of full-length (intact) IgG is stronger in strain 16 extract, indicating the incorporation of nnAA was substantially increased, with a decrease in truncated proteins. 2(B) shows the IgG soluble yield of proteins containing a nnAA at the indicated positions of heavy chain is substantially increased in strain 16 extract, indicating that OmpT cleavage of RF1 variant A18 results in less truncated heavy chain. "RF1+" (RF1 positive) extract refers to RF1 from strain 001 that is not cleaved by OmpT. "RF1−" (RF1 negative) extract refers to RF1 from strain 16 that is modified to include OmpT cleavage sites, and is thus degraded by OmpT activity.
Figure 3:
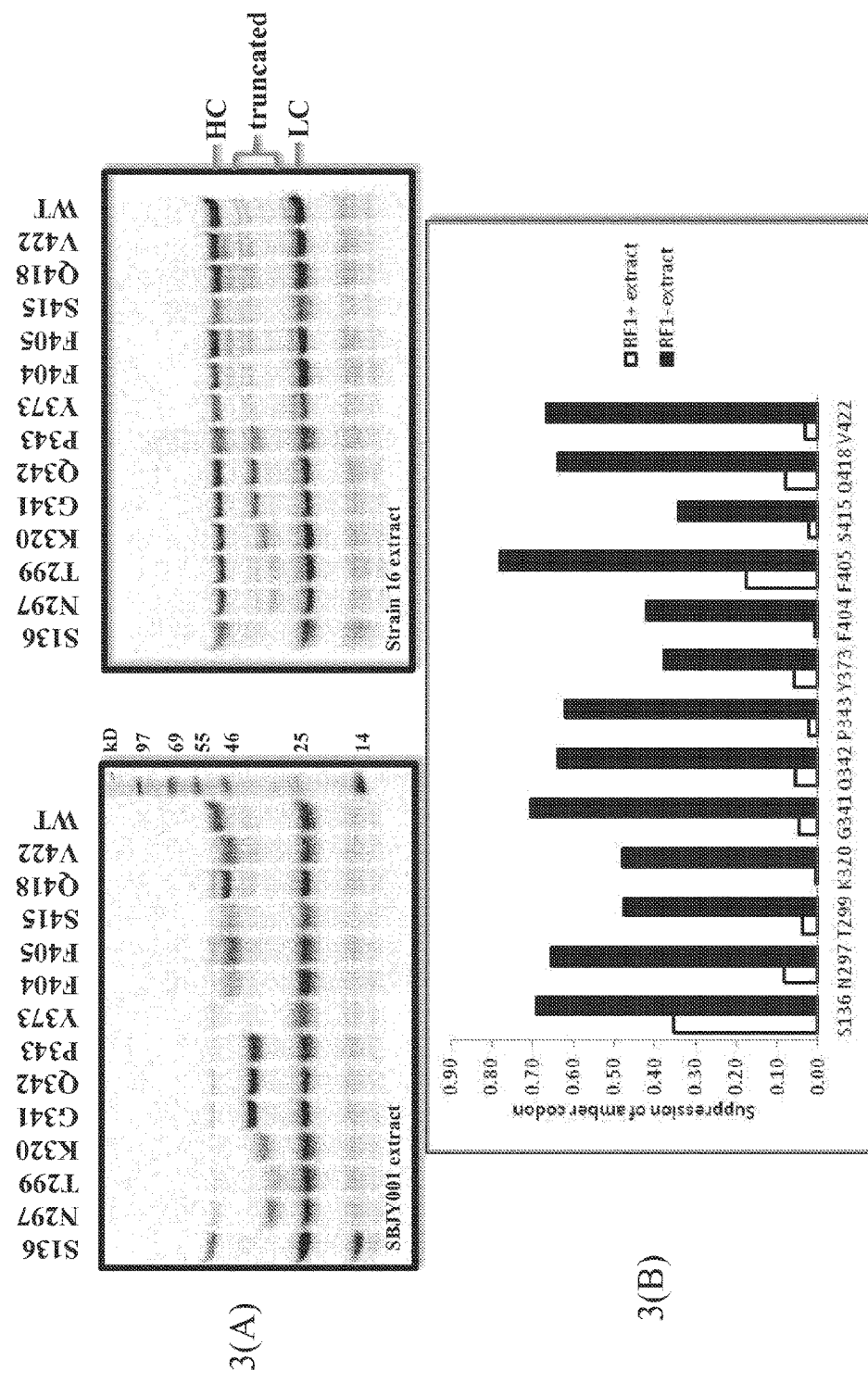
FIG. 3 shows that cell-free extracts from a bacterial strain engineered to express a modified RF1 variant (A18) produce a substantial increase in amber suppression corresponding to increased incorporation of nnAA at the indicated positions of heavy chain. 3(A) left panel: SBJY001 extract, containing intact OmpT and wild-type RF1. 3(A) right panel: SBHS016 (strain 16) extract, containing intact OmpT and RF1 variant A18. The band intensity of full-length (intact) heavy chain (Hc) is stronger in strain 16 extract, indicating the incorporation of nnAA was substantially increased, with a decrease in truncated proteins. 3(B) shows amber suppression of proteins containing a nnAA at the indicated positions of heavy chain is substantially increased in strain 16 extract, indicating that OmpT cleavage of RF1 variant A18 results in increased amber suppression. "RF1+" (RF1 positive) extract refers to RF1 from strain 001 that is not cleaved by OmpT. "RF1−" (RF1 negative) extract refers to RF1 from strain 16 that is modified to include OmpT cleavage sites, and is thus degraded by OmpT activity.

As shown in FIG. 2, expression of the IgG heavy chain TAG variants in the SBJY001 cell free extract, which expresses OmpT1 and wild-type RF-1, resulted in relatively poor yield of soluble full length IgG. In contrast, expression of the IgG heavy chain TAG variants in the SBHS016 cell free extract, which expresses OmpT1 and a modified RF-1 protein (variant A18) containing the triple substitution N296K/L297R/L298R, resulted in relatively high yield of full length IgG. Further, as shown in FIG. 3, expression of the IgG heavy chain TAG variants in the SBJY001 cell free extract resulted in relatively poor amber suppression (i.e., the heavy chain protein was truncated). In contrast, expression of the IgG heavy chain TAG variants in the SBHS016 cell free extract resulted in relatively high amber suppression (i.e., much less of the heavy chain protein was truncated), which corresponds to the substantially higher yields of full length IgG observed in FIG. 2.

This example demonstrates that OmpT1 cleavage of RF1 provides a dramatic improvement in the yield of heavy chains incorporating the desired nnAA at an amber codon in the coding sequence, as compared to intact RF1 that is not cleavable by OmpT1.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

LIST OF SEQUENCES

*Escherichia coli* Release Factor 1 (RF1)

SEQ ID NO: 1

MKPSIVAKLEALHERHEEVQALLGDAQTIADQERFRALSREYAQLSDVSRCFTDWQ

QVQEDIETAQMMLDDPEMREMAQDELREAKEKSEQLEQQLQVLLLPKDPDDERNA

FLEVRAGTGGDEAALFAGDLFRMYSRYAEARRWRVEIMSASEGEHGGYKEIIAKISG

DGVYGRLKFESGGHRVQRVPATESQGRIHTSACTVAVMPELPDAELPDINPADLRID

TFRSSGAGGQHVNTTDSAIRITHLPTGIVVECQDERSQHKNKAKALSVLGARIHAAE

MAKRQQAEASTRRNLLGSGDRSDRNRTYNFPQGRVTDHRINLTLYRLDEVMEGKLD

MLIEPIIQEHQADQLAALSEQE

-continued

*Escherichia coli* Release Factor 2 (RF2)
SEQ ID NO: 2

MFEINPVNNRIQDLTERSDVLRGYLDYDAKKERLEEVNAELEQPDVWNEPERAQAL

GKERSSLEAVVDTLDQMKQGLEDVSGLLELAVEADDEETFNEAVAELDALEEKLAQ

LEFRRMFSGEYDSADCYLDIQAGSGGTEAQDWASMLERMYLRWAESRGFKTEIIEES

EGEVAGIKSVTIKISGDYAYGWLRTETGVHRLVRKSPFDSGGRRHTSFSSAFVYPEVD

DDIDIEINPADLRIDVYRTSGAGGQHVNRTESAVRITHIPTGIVTQCQNDRSQHKNKD

QAMKQMKAKLYELEMQKKNAEKQAMEDNKSDIGWGSQIRSYVLDDSRIKDLRTGV

ETRNTQAVLDGSLDQFIEASLKAGL

*Escherichia coli* Outer Membrane Protein T1 (OmpT)
(signal peptide underlined)
SEQ ID NO: 3

<u>MRAKLLGIVLTTPIAISSFA</u>STETLSFTPDNINADISLGTLSGKTKERVYLAEEGGRKVS

QLDWKFNNAAIIKGAINWDLMPQISIGAAGWTTLGSRGGNMVDQDWMDSSNPGTW

TDESRHPDTQLNYANEFDLNIKGWLLNEPNYRLGLMAGYQESRYSFTARGGSYIYSS

EEGFRDDIGSFPNGERAIGYKQRFKMPYIGLTGSYRYEDFELGGTFKYSGWVESSDN

DEHYDPGKRITYRSKVKDQNYYSVAVNAGYYVTPNAKVYVEGAWNRVTNKKGNT

SLYDHNNNTSDYSKNGAGIENYNFITTAGLKYTF

Switch loop region of Release Factor 1 (RF1), amino acids
287 to 304
SEQ ID NO: 4
QQAEASTRRNLLGSGDRS N296K mutation in the switch loop region of Release
Factor 1 (RF1), amino acids 287 to 304
SEQ ID NO: 5
QQAEASTRRKLLGSGDRS N296R mutation in the switch loop region of Release
Factor 1 (RF1), amino acids 287 to 304
SEQ ID NO: 6
QQAEASTRRRLLGSGDRS L297K mutation in the switch loop region of Release
Factor 1 (RF1), amino acids 287 to 304
SEQ ID NO: 7
QQAEASTRRNKLGSGDRS L297R mutation in the switch loop region of Release
Factor 1 (RF1), amino acids 287 to 304
SEQ ID NO: 8
QQAEASTRRNRLGSGDRS L297V mutation in the switch loop region of Release
Factor 1 (RF1), amino acids 287 to 304
SEQ ID NO: 9
QQAEASTRRNVLGSGDRS L298K mutation in the switch loop region of Release
Factor 1 (RF1), amino acids 287 to 304
SEQ ID NO: 10
QQAEASTRRNLKGSGDRS L298R mutation in the switch loop region of Release
Factor 1 (RF1), amino acids 287 to 304
SEQ ID NO: 11
QQAEASTRRNLRGSGDRS N296K, L297K mutation in the switch loop region of
Release Factor 1 (RF1), amino acids 287 to 304
SEQ ID NO: 12
QQAEASTRRKKLGSGDRS N296K, L297R = A13 mutation in the switch loop
region of Release Factor 1 (RF1), amino acids
287 to 304
SEQ ID NO: 13

-continued

QQAEASTRRKRLGSGDRS

N296K, L297V mutation in the switch loop region of
Release Factor 1 (RF1), amino acids 287 to 304

SEQ ID NO: 14

QQAEASTRRKVLGSGDRS

N296K, L297V mutation in the switch loop region of
Release Factor 1 (RF1), amino acids 287 to 304

SEQ ID NO: 15

QQAEASTRRRKLGSGDRS

N296R, L297R mutation in the switch loop region of
Release Factor 1 (RF1), amino acids 287 to 304

SEQ ID NO: 16

QQAEASTRRRRLGSGDRS

N296R, L297V mutation in the switch loop region of
Release Factor 1 (RF1), amino acids 287 to 304

SEQ ID NO: 17

QQAEASTRRRVLGSGDRS

N296K, L297K, L298K mutation in the switch loop
region of Release Factor 1 (RF1), amino acids
287 to 304

SEQ ID NO: 18

QQAEASTRRKKKGSGDRS

N296K, L297K, L298R mutation in the switch loop
region of Release Factor 1 (RF1), amino acids
287 to 304

SEQ ID NO: 19

QQAEASTRRKKRGSGDRS

N296K, L297R, L298K = A17 mutation in the switch
loop region of Release Factor 1 (RF1), amino
acids
287 to 304

SEQ ID NO: 20

QQAEASTRRKRKGSGDRS

N296K, L297R, L298R = A18 mutation in the switch
loop region of Release Factor 1 (RF1), amino
acids 287 to 304

SEQ ID NO: 21

QQAEASTRRKRRGSGDRS

N296R, L297R, L298R mutation in the switch loop
region of Release Factor 1 (RF1), amino acids
287 to 304

SEQ ID NO: 22

QQAEASTRRRRRGSGDRS

N296R, L297K, L298R mutation in the switch loop
region of Release Factor 1 (RF1), amino acids
287 to 304

SEQ ID NO: 23

QQAEASTRRRKRGSGDRS

N296R, L297R, L298K mutation in the switch loop
region of Release Factor 1 (RF1), amino acids
287 to 304

SEQ ID NO: 24

QQAEASTRRRRKGSGDRS

N296R, L297K, L298K mutation in the switch loop
region of Release Factor 1 (RF1), amino acids
287 to 304

SEQ ID NO: 25

QQAEASTRRRKKGSGDRS

OmpT cleavage peptide sequence inserted in the
switch loop of Release Factor 1 (RF1), amino acids
287 to 304

SEQ ID NO: 26

Q<u>ARRG</u>STRRNLLGSGDRS

OmpT cleavage peptide sequence inserted in the
switch loop of Release Factor 1 (RF1), amino
acids 287 to 304

SEQ ID NO: 27

-continued

QQ<u>ARRG</u>TRRNLLGSGDRS

OmpT cleavage peptide sequence inserted in the switch loop of Release Factor 1 (RF1), amino acids 287 to 304

SEQ ID NO: 28

QQA<u>ARRG</u>RRNLLGSGDRS

OmpT cleavage peptide sequence inserted in the switch loop of Release Factor 1 (RF1), amino acids 287 to 304

SEQ ID NO: 29

QQAE<u>ARRG</u>RNLLGSGDRS

OmpT cleavage peptide sequence inserted in the switch loop of Release Factor 1 (RF1), amino acids 287 to 304

SEQ ID NO: 30

QQAEA<u>ARRG</u>NLLGSGDRS

OmpT cleavage peptide sequence inserted in the switch loop of Release Factor 1 (RF1), amino acids 287 to 304

SEQ ID NO: 31

QQAEAS<u>ARRG</u>LLGSGDRS

OmpT cleavage peptide sequence inserted in the switch loop of Release Factor 1 (RF1), amino acids 287 to 304

SEQ ID NO: 32

QQAEAST<u>ARRG</u>LGSGDRS

OmpT cleavage peptide sequence inserted in the switch loop of Release Factor 1 (RF1), amino acids 287 to 304

SEQ ID NO: 33

QQAEASTR<u>ARRG</u>GSGDRS

OmpT cleavage peptide sequence inserted in the switch loop of Release Factor 1 (RF1), amino acids 287 to 304

SEQ ID NO: 34

QQAEASTRR<u>ARRG</u>SGDRS

OmpT cleavage peptide sequence inserted in the switch loop of Release Factor 1 (RF1), amino acids 287 to 304

SEQ ID NO: 35

QQAEASTRRN<u>ARRG</u>GDRS

OmpT cleavage peptide sequence inserted in the switch loop of Release Factor 1 (RF1), amino acids 287 to 304

SEQ ID NO: 36

QQAEASTRRNL<u>ARRG</u>DRS

OmpT cleavage peptide sequence inserted in the switch loop of Release Factor 1 (RF1), amino acids 287 to 304

SEQ ID NO: 37

QQAEASTRRNLL<u>ARRG</u>RS

OmpT cleavage peptide sequence inserted in the switch loop of Release Factor 1 (RF1), amino acids 287 to 304

SEQ ID NO: 38

QQAEASTRRNLLG<u>ARRG</u>S

OmpT cleavage peptide sequence inserted in the switch loop of Release Factor 1 (RF1), amino acids 287 to 304

SEQ ID NO: 39

QQAEASTRRNLLGS<u>ARRG</u>

OmpT cleavage peptide sequence inserted in the switch loop of Release Factor 1 (RF1), amino acids 287 to 304

SEQ ID NO: 40

QQAEASTRRNLLGSG<u>ARR</u>

OmpT cleavage peptide sequence inserted in the

-continued switch loop of Release Factor 1 (RF1), amino acids 287 to 304

SEQ ID NO: 41

QQAWLAARRGRGGSGDRS

OmpT cleavage peptide sequence inserted in the switch loop of Release Factor 1 (RF1), amino acids 287 to 304

SEQ ID NO: 42

QQAEWLAARRGRGSGDRS

OmpT cleavage peptide sequence inserted in the switch loop of Release Factor 1 (RF1), amino acids 287 to 304

SEQ ID NO: 43

QQAEAWLAARRGRGGDRS

OmpT cleavage peptide sequence inserted in the switch loop of Release Factor 1 (RF1), amino acids 287 to 304

SEQ ID NO: 44

QQWGGRWARKKGTIGDRS

OmpT cleavage peptide sequence inserted in the switch loop of Release Factor 1 (RF1), amino acids 287 to 304

SEQ ID NO: 45

QQAWGGRWARKKGTIDRS

OmpT cleavage peptide sequence inserted in the switch loop of Release Factor 1 (RF1), amino acids 287 to 304

SEQ ID NO: 46

QQAEWGGRWARKKGTIRS

OmpT cleavage peptide

SEQ ID NO: 47

ARRG

OmpT cleavage peptide

SEQ ID NO: 48

WLAARRGRG

OmpT cleavage peptide

SEQ ID NO: 49

WGGRWARKKGTI

C-terminal sequence of short form of λ phage Gam protein (GamS)

SEQ ID NO: 50

GGSHHHHHH short form of λ phage Gam protein (GamS) gene amplification primer

SEQ ID NO: 51

ATATATCATATGAACGCTTATTACATTCAGGATCGTCTTGAG short form of λ phage Gam protein (GamS) gene amplification primer

SEQ ID NO: 52

ATATATGTCGACTTAATGATGATGATGATGATGAGAACCCCCTACCTCTGAATCA

ATATCAACCTGGTGGTG

5'-fragment including T7 promoter, constant region of the N-terminal sequence and the mutation site first step PCR amplification primer 5chiT2PT7

SEQ ID NO: 53

GCGTACTAGCGTACCACGTGGCTGGTGGCCCGATTCATTAATGCAGCTGGCACGAC

AGG

3'-fragment including mutation site, constant C-terminal region and T7 terminator sequences first step PCR amplification primer 3chiT2TT7

SEQ ID NO: 54

GCGTACTAGCGTACCACGTGGCTGGTGGCGGTGAGTTTTCTCCTTCATTACAGAA

ACGGC single primer 5chiT2 for 5'-fragment and 3'-fragment

-continued assembly by overlapping PCR
SEQ ID NO: 55
GCGTACTAGCGTACCACGTGGCTGGTGG WT RF1 variant OmpT cleavage site screening forward
primer
SEQ ID NO: 56
GCTCGATGATCCTGAAATGCGTGAGATGGCGCAGG M74R RF1 variant OmpT cleavage site screening forward
primer
SEQ ID NO: 57
GCTCGATGATCCTGAACGCCGTGAGATGGCGCAGG E76K RF1 variant OmpT cleavage site screening forward
primer
SEQ ID NO: 58
CGATGATCCTGAAATGCGTAAGATGGCGCAGGATGAAC E84K RF1 variant OmpT cleavage site screening forward
primer
SEQ ID NO: 59
CAGGATGAACTGCGCAAAGCTAAAGAAAAAAGCGAGCAAC A85R RF1 variant OmpT cleavage site screening forward
primer
SEQ ID NO: 60
CAGGATGAACTGCGCGAACGTAAAGAAAAAAGCGAGCAAC E87R RF1 variant OmpT cleavage site screening forward
primer
SEQ ID NO: 61
GGATGAACTGCGCGAAGCTAAACGTAAAAGCGAGCAACTGGAAC E108R RF1 variant OmpT cleavage site screening forward
primer
SEQ ID NO: 62
GCCAAAAGATCCTGATGACCGTCGTAACGCCTTCCTCG T293R RF1 variant OmpT cleavage site screening forward
primer
SEQ ID NO: 63
CAACAGGCCGAAGCGTCTCGCCGTCGTAACCTGC N296K RF1 variant OmpT cleavage site screening forward
primer
SEQ ID NO: 64
GCGTCTACCCGTCGTAAACTGCTGGGGAGTGGCG S304K RF1 variant OmpT cleavage site screening forward
primer
SEQ ID NO: 65
GGGAGTGGCGATCGCAAGGACCGTAACCGTACTTAC N296K/L297V RF1 variant OmpT cleavage site screening
forward primer
SEQ ID NO: 66
CGAAGCGTCTACCCGTCGTAAAGTTCTGGGGAGTGGCGATCGCAGC N296K/L297K RF1 variant OmpT cleavage site screening
forward primer
SEQ ID NO: 67
CGAAGCGTCTACCCGTCGTAAAAAGCTGGGGAGTGGCGATCGCAGC N296K/L297R RF1 variant OmpT cleavage site screening
forward primer
SEQ ID NO: 68
CGAAGCGTCTACCCGTCGTAAACGTCTGGGGAGTGGCGATCGCAGC N296R/L297V RF1 variant OmpT cleavage site screening
forward primer
SEQ ID NO: 69
CGAAGCGTCTACCCGTCGTCGCGTTCTGGGGAGTGGCGATCGCAGC N296R/L297K RF1 variant OmpT cleavage site screening
forward primer
SEQ ID NO: 70
CGAAGCGTCTACCCGTCGTCGCAAGCTGGGGAGTGGCGATCGCAGC N296R/L297R RF1 variant OmpT cleavage site screening
forward primer -continued

CGAAGCGTCTACCCGTCGTCGCCGTCTGGGGAGTGGCGATCGCAGC  
SEQ ID NO: 71

N296K/L297R/L298K RF1 variant OmpT cleavage site screening forward primer  
SEQ ID NO: 72  
CAGGCCGAAGCGTCTACCCGTCGTAAACGTAAGGGGAGTGGCGATCGCAGCGAC  
C N296K/L297R/L298R RF1 variant OmpT cleavage site screening forward primer  
SEQ ID NO: 73  
CAGGCCGAAGCGTCTACCCGTCGTAAACGTCGCGGGAGTGGCGATCGCAGCGAC  
C WT RF1 variant OmpT cleavage site screening reverse primer  
SEQ ID NO: 74  
CCTGCGCCATCTCACGCATTTCAGGATCATCGAGC M74R RF1 variant OmpT cleavage site screening reverse primer  
SEQ ID NO: 75  
CCTGCGCCATCTCACGGCGTTCAGGATCATCGAGC E76K RF1 variant OmpT cleavage site screening reverse primer  
SEQ ID NO: 76  
GTTCATCCTGCGCCATCTTACGCATTTCAGGATCATCG E84K RF1 variant OmpT cleavage site screening reverse primer  
SEQ ID NO: 77  
GTTGCTCGCTTTTTTCTTTAGCTTTGCGCAGTTCATCCTG A85R RF1 variant OmpT cleavage site screening reverse primer  
SEQ ID NO: 78  
GTTGCTCGCTTTTTTCTTTACGTTCGCGCAGTTCATCCTG E87R RF1 variant OmpT cleavage site screening reverse primer  
SEQ ID NO: 79  
GTTCCAGTTGCTCGCTTTTACGTTTAGCTTCGCGCAGTTCATCC E108R RF1 variant OmpT cleavage site screening reverse primer  
SEQ ID NO: 80  
CGAGGAAGGCGTTACGACGGTCATCAGGATCTTTTGGC T293R RF1 variant OmpT cleavage site screening reverse primer  
SEQ ID NO: 81  
GCAGGTTACGACGGCGAGACGCTTCGGCCTGTTG N296K RF1 variant OmpT cleavage site screening reverse primer  
SEQ ID NO: 82  
CGCCACTCCCCAGCAGTTTACGACGGGTAGACGC S304K RF1 variant OmpT cleavage site screening reverse primer  
SEQ ID NO: 83  
GTAAGTACGGTTACGGTCCTTGCGATCGCCACTCCC N296K/L297V RF1 variant OmpT cleavage site screening reverse primer  
SEQ ID NO: 84  
GCTGCGATCGCCACTCCCCAGAACTTTACGACGGGTAGACGCTTCG N296K/L297K RF1 variant OmpT cleavage site screening reverse primer  
SEQ ID NO: 85  
GCTGCGATCGCCACTCCCCAGCTTTTTACGACGGGTAGACGCTTCG N296K/L297R RF1 variant OmpT cleavage site screening reverse primer  
SEQ ID NO: 86  
GCTGCGATCGCCACTCCCCAGACGTTTACGACGGGTAGACGCTTCG -continued N296R/L297V RF1 variant OmpT cleavage site screening
reverse primer
                                                SEQ ID NO: 87
GCTGCGATCGCCACTCCCCAG<u>AACGCG</u>ACGACGGGTAGACGCTTCG N296R/L297K RF1 variant OmpT cleavage site screening
reverse primer
                                                SEQ ID NO: 88
GCTGCGATCGCCACTCCCCAG<u>CTTGCG</u>ACGACGGGTAGACGCTTCG N296R/L297R RF1 variant OmpT cleavage site screening
reverse primer
                                                SEQ ID NO: 89
GCTGCGATCGCCACTCCCCAG<u>ACGGCG</u>ACGACGGGTAGACGCTTCG N296K/L297R/L298K RF1 variant OmpT cleavage site
screening reverse primer
                                                SEQ ID NO: 90
GGTCGCTGCGATCGCCACTCCCC<u>CTTACGTTT</u>ACGACGGGTAGACGCTTCGGCCTG N296K/L297R/L298R RF1 variant OmpT cleavage site
screening reverse primer
                                                SEQ ID NO: 91
GGTCGCTGCGATCGCCACTCCC<u>GCGACGTTT</u>ACGACGGGTAGACGCTTCGGCCTG No. 0 RF1 variant OmpT cleavage peptide insertion
forward oligo primer
                                                SEQ ID NO: 92
GCCGAAGCGTCTACCCGTCGTAACCTGCTGGGGAGTGGCGATCGCAGCGACCGT

AACCGTACTTACAACTTCCCG

No. 1 RF1 variant OmpT cleavage peptide insertion
forward oligo primer
                                                SEQ ID NO: 93
<u>CGCCGTGGTT</u>CTACCCGTCGTAACCTGCTGGGGAGTGGCGATCGCAGCGACCGTA

ACCGTACTTACAACTTCCCG

No. 2 RF1 variant OmpT cleavage peptide insertion
forward oligo primer
                                                SEQ ID NO: 94
<u>GCACGCCGTGGT</u>ACCCGTCGTAACCTGCTGGGGAGTGGCGATCGCAGCGACCGT

AACCGTACTTACAACTTCCCG

No. 3 RF1 variant OmpT cleavage peptide insertion
forward oligo primer
                                                SEQ ID NO: 95
GCC<u>GCACGCCGTGGT</u>CGTCGTAACCTGCTGGGGAGTGGCGATCGCAGCGACCGT

AACCGTACTTACAACTTCCCG

No. 4 RF1 variant OmpT cleavage peptide insertion
forward oligo primer
                                                SEQ ID NO: 96
GCCGAA<u>GCACGCCGTGGT</u>CGTAACCTGCTGGGGAGTGGCGATCGCAGCGACCGT

AACCGTACTTACAACTTCCCG

No. 5 RF1 variant OmpT cleavage peptide insertion
forward oligo primer
                                                SEQ ID NO: 97
GCCGAAGCG<u>GCACGCCGTGGT</u>AACCTGCTGGGGAGTGGCGATCGCAGCGACCGT

AACCGTACTTACAACTTCCCG

No. 6 RF1 variant OmpT cleavage peptide insertion
forward oligo primer
                                                SEQ ID NO: 98
GCCGAAGCGTCT<u>GCACGCCGTGGT</u>CTGCTGGGGAGTGGCGATCGCAGCGACCGT

AACCGTACTTACAACTTCCCG

No. 7 RF1 variant OmpT cleavage peptide insertion
forward oligo primer
                                                SEQ ID NO: 99
GCCGAAGCGTCTACC<u>GCACGCCGTGGT</u>CTGGGGAGTGGCGATCGCAGCGACCGT

AACCGTACTTACAACTTCCCG

-continued

No. 8 RF1 variant OmpT cleavage peptide insertion
forward oligo primer
SEQ ID NO: 100
GCCGAAGCGTCTACCCGT<u>GCACGCCGTGGT</u>GGGAGTGGCGATCGCAGCGACCGT

AACCGTACTTACAACTTCCCG

No. 9 RF1 variant OmpT cleavage peptide insertion
forward oligo primer
SEQ ID NO: 101
GCCGAAGCGTCTACCCGTCGT<u>GCACGCCGTGGT</u>AGTGGCGATCGCAGCGACCGT

AACCGTACTTACAACTTCCCG

No. 10 RF1 variant OmpT cleavage peptide insertion
forward oligo primer
SEQ ID NO: 102
GCCGAAGCGTCTACCCGTCGTAAC<u>GCACGCCGTGGT</u>GGCGATCGCAGCGACCGT

AACCGTACTTACAACTTCCCG

No. 11 RF1 variant OmpT cleavage peptide insertion
forward oligo primer
SEQ ID NO: 103
GCCGAAGCGTCTACCCGTCGTAACCTG<u>GCACGCCGTGGT</u>GATCGCAGCGACCGT

AACCGTACTTACAACTTCCCG

No. 12 RF1 variant OmpT cleavage peptide insertion
forward oligo primer
SEQ ID NO: 104
GCCGAAGCGTCTACCCGTCGTAACCTGCTG<u>GCACGCCGTGGT</u>CGCAGCGACCGTA

ACCGTACTTACAACTTCCCG

No. 13 RF1 variant OmpT cleavage peptide insertion
forward oligo primer
SEQ ID NO: 105
GCCGAAGCGTCTACCCGTCGTAACCTGCTGGGG<u>GCACGCCGTGGT</u>AGCGACCGT

AACCGTACTTACAACTTCCCG

No. 14 RF1 variant OmpT cleavage peptide insertion
forward oligo primer
SEQ ID NO: 106
GCCGAAGCGTCTACCCGTCGTAACCTGCTGGGGAGT<u>GCACGCCGTGGT</u>GACCGT

AACCGTACTTACAACTTCCCG

No. 15 RF1 variant OmpT cleavage peptide insertion
forward oligo primer
SEQ ID NO: 107
GCCGAAGCGTCTACCCGTCGTAACCTGCTGGGGAGTGGC<u>GCACGCCGT</u>GACCGT

AACCGTACTTACAACTTCCCG

No. 16 RF1 variant OmpT cleavage peptide insertion
forward oligo primer
SEQ ID NO: 108
GCCGAAGCGTCTACCCGTCGT<u>CGT</u>CTGCTGGGGAGTGGCGATCGCAGCGACCGT

AACCGTACTTACAACTTCCCG

No. 17 RF1 variant OmpT cleavage peptide insertion
forward oligo primer
SEQ ID NO: 109
GCC<u>TGGCTGGCAGCGCGTCGCGGTCGTGGC</u>GGGAGTGGCGATCGCAGCGACCGT

AACCGTACTTACAACTTCCCG

No. 18 RF1 variant OmpT cleavage peptide insertion
forward oligo primer
SEQ ID NO: 110
GCCGAA<u>TGGCTGGCAGCGCGTCGCGGTCGTGGC</u>AGTGGCGATCGCAGCGACCGT

AACCGTACTTACAACTTCCCG

No. 19 RF1 variant OmpT cleavage peptide insertion
forward oligo primer
SEQ ID NO: 111

GCCGAAGCGTGGCTGGCAGCGCGTCGCGGTCGTGGCGGCGATCGCAGCGACCGT

AACCGTACTTACAACTTCCCG

No. 20 RF1 variant OmpT cleavage peptide insertion
forward oligo primer
SEQ ID NO: 112
TGGGGTGGCCGTTGGGCTCGCAAGAAAGGTACTATTGGCGATCGCAGCGACCGT

AACCGTACTTACAACTTCCCG

No. 21 RF1 variant OmpT cleavage peptide insertion
forward oligo primer
SEQ ID NO: 113
GCCTGGGGTGGCCGTTGGGCTCGCAAGAAAGGTACTATTGATCGCAGCGACCGT

AACCGTACTTACAACTTCCCG

No. 22 RF1 variant OmpT cleavage peptide insertion
forward oligo primer
SEQ ID NO: 114
GCCGAATGGGGTGGCCGTTGGGCTCGCAAGAAAGGTACTATTCGCAGCGACCGT

AACCGTACTTACAACTTCCCG

No. 0 RF1 variant OmpT cleavage peptide insertion
reverse oligo primer
SEQ ID NO: 115
GCTGCGATCGCCACTCCCCAGCAGGTTACGACGGGTAGACGCTTCGGCCTGTTGG

CGTTTTGCCATTTCAGCAGC

No. 1 RF1 variant OmpT cleavage peptide insertion
reverse oligo primer
SEQ ID NO: 116
GCTGCGATCGCCACTCCCCAGCAGGTTACGACGGGTAGAACCACGGCGTGCTTG

GCGTTTTGCCATTTCAGCAGC

No. 2 RF1 variant OmpT cleavage peptide insertion
reverse oligo primer
SEQ ID NO: 117
GCTGCGATCGCCACTCCCCAGCAGGTTACGACGGGTACCACGGCGTGCCTGTTGG

CGTTTTGCCATTTCAGCAGC

No. 3 RF1 variant OmpT cleavage peptide insertion
reverse oligo primer
SEQ ID NO: 118
GCTGCGATCGCCACTCCCCAGCAGGTTACGACGACCACGGCGTGCGGCCTGTTGG

CGTTTTGCCATTTCAGCAGC

No. 4 RF1 variant OmpT cleavage peptide insertion
reverse oligo primer
SEQ ID NO: 119
GCTGCGATCGCCACTCCCCAGCAGGTTACGACCACGGCGTGCTTCGGCCTGTTGG

CGTTTTGCCATTTCAGCAGC

No. 5 RF1 variant OmpT cleavage peptide insertion
reverse oligo primer
SEQ ID NO: 120
GCTGCGATCGCCACTCCCCAGCAGGTTACCACGGCGTGCCGCTTCGGCCTGTTGG

CGTTTTGCCATTTCAGCAGC

No. 6 RF1 variant OmpT cleavage peptide insertion
reverse oligo primer
SEQ ID NO: 121
GCTGCGATCGCCACTCCCCAGCAGACCACGGCGTGCAGACGCTTCGGCCTGTTGG

CGTTTTGCCATTTCAGCAGC

No. 7 RF1 variant OmpT cleavage peptide insertion
reverse oligo primer
SEQ ID NO: 122
GCTGCGATCGCCACTCCCCAGACCACGGCGTGCGGTAGACGCTTCGGCCTGTTGG

CGTTTTGCCATTTCAGCAGC

-continued

No. 8 RF1 variant OmpT cleavage peptide insertion reverse oligo primer
SEQ ID NO: 123
GCTGCGATCGCCACTCCC<u>ACCACGGCGTGC</u>ACGGGTAGACGCTTCGGCCTGTTGG

CGTTTTGCCATTTCAGCAGC

No. 9 RF1 variant OmpT cleavage peptide insertion reverse oligo primer
SEQ ID NO: 124
GCTGCGATCGCCACT<u>ACCACGGCGTGC</u>ACGACGGGTAGACGCTTCGGCCTGTTGG

CGTTTTGCCATTTCAGCAGC

No. 10 RF1 variant OmpT cleavage peptide insertion reverse oligo primer
SEQ ID NO: 125
GCTGCGATCGCC<u>ACCACGGCGTGC</u>GTTACGACGGGTAGACGCTTCGGCCTGTTGG

CGTTTTGCCATTTCAGCAGC

No. 11 RF1 variant OmpT cleavage peptide insertion reverse oligo primer
SEQ ID NO: 126
GCTGCGATC<u>ACCACGGCGTGC</u>CAGGTTACGACGGGTAGACGCTTCGGCCTGTTGG

CGTTTTGCCATTTCAGCAGC

No. 12 RF1 variant OmpT cleavage peptide insertion reverse oligo primer
SEQ ID NO: 127
GCTGCG<u>ACCACGGCGTGC</u>CAGCAGGTTACGACGGGTAGACGCTTCGGCCTGTTG

GCGTTTTGCCATTTCAGCAGC

No. 13 RF1 variant OmpT cleavage peptide insertion reverse oligo primer
SEQ ID NO: 128
GCT<u>ACCACGGCGTGC</u>CCCCAGCAGGTTACGACGGGTAGACGCTTCGGCCTGTTGG

CGTTTTGCCATTTCAGCAGC

No. 14 RF1 variant OmpT cleavage peptide insertion reverse oligo primer
SEQ ID NO: 129
<u>ACCACGGCGTGC</u>ACTCCCCAGCAGGTTACGACGGGTAGACGCTTCGGCCTGTTGG

CGTTTTGCCATTTCAGCAGC

No. 15 RF1 variant OmpT cleavage peptide insertion reverse oligo primer
SEQ ID NO: 130
<u>ACGGCGTGC</u>GCCACTCCCCAGCAGGTTACGACGGGTAGACGCTTCGGCCTGTTGG

CGTTTTGCCATTTCAGCAGC

No. 16 RF1 variant OmpT cleavage peptide insertion reverse oligo primer
SEQ ID NO: 131
GCTGCGATCGCCACTCCCCAGCAG<u>ACGA</u>CGACGGGTAGACGCTTCGGCCTGTTG

GCGTTTTGCCATTTCAGCAGC

No. 17 RF1 variant OmpT cleavage peptide insertion reverse oligo primer
SEQ ID NO: 132
GCTGCGATCGCCACTCCC<u>GCCACGACCGCGACGCGCTGCCAGCCA</u>GGCCTGTTGG

CGTTTTGCCATTTCAGCAGC

No. 18 RF1 variant OmpT cleavage peptide insertion reverse oligo primer
SEQ ID NO: 133
GCTGCGATCGCCACT<u>GCCACGACCGCGACGCGCTGCCAGCCA</u>TTCGGCCTGTTGG

CGTTTTGCCATTTCAGCAGC

No. 19 RF1 variant OmpT cleavage peptide insertion reverse oligo primer
SEQ ID NO: 134
GCTGCGATCGCC<u>GCCACGACCGCGACGCGCTGCCAGCCA</u>CGCTTCGGCCTGTTGG -continued

CGTTTTGCCATTTCAGCAGC

No. 20 RF1 variant OmpT cleavage peptide insertion
reverse oligo primer
SEQ ID NO: 135
GCTGCGATCGCCAATAGTACCTTTCTTGCGAGCCCAACGGCCACCCCACTGTTGG

CGTTTTGCCATTTCAGCAGC

No. 21 RF1 variant OmpT cleavage peptide insertion
reverse oligo primer
SEQ ID NO: 136
GCTGCGATCAATAGTACCTTTCTTGCGAGCCCAACGGCCACCCCAGGCCTGTTGG

CGTTTTGCCATTTCAGCAGC

No. 22 RF1 variant OmpT cleavage peptide insertion
reverse oligo primer
SEQ ID NO: 137
GCTGCGAATAGTACCTTTCTTGCGAGCCCAACGGCCACCCCATTCGGCCTGTTGG

CGTTTTGCCATTTCAGCAGC

RF1 amplification primer 5His-RF1
SEQ ID NO: 138
CATATGCATCACCATCACCATCACGGTGGTGGCTCTAAGCCTTCTATCGTTGCCA

AACTGGAAGCC

RF1 amplification primer 3RF1
SEQ ID NO: 139
GTCGACTTATTCCTGCTCGGACAACGCCGCCAG

Oligonucleotide-Mediated Allelic Replacement (OMAR) PCR
oligo 1opRF1 KR
SEQ ID NO: 140
GGGAAGTTGTAAGTACGGTTACGGTCGCTGCGATCcCCtgaaCCaAGacGcTTtCGACGGGTA

GACGCTTCGGCCTGTTGGCGTTTTGCC

Oligonucleotide-Mediated Allelic Replacement (OMAR) PCR
oligo 1opRF1 KRR
SEQ ID NO: 141
GGGAAGTTGTAAGTACGGTTACGGTCGCTGCGATCcCCtgaaCCacgacGcTTtCGACG

GGTAGACGCTTCGGCCTGTTGGCGTTTTGCC

Oligonucleotide-Mediated Allelic Replacement (OMAR) PCR
oligo 1opRF1 KRK
SEQ ID NO: 142
GGGAAGTTGTAAGTACGGTTACGGTCGCTGCGATCcCCtgaaCCcttacGcTTtCGACGG

GTAGACGCTTCGGCCTGTTGGCGTTTTGCC

Mismatch Amplification Mutation Assay (MAMA)
PCR oligo 3KR op-PCR
SEQ ID NO: 143
GCG ATC CCC TGA ACC AAG ACG C Mismatch Amplification Mutation Assay (MAMA)
PCR oligo 3 KRR op-PCR
SEQ ID NO: 144
CGATCcCCtgaaCCacgacGc Mismatch Amplification Mutation Assay (MAMA)
PCR oligo 3KRK op-PCR
SEQ ID NO: 145
TGCGATCcCCtgaaCCcttacGc Mismatch Amplification Mutation Assay (MAMA)
PCR oligo 5 RF1 op-PCR
SEQ ID NO: 146
CGTGACGGGGATAACGAACGCC rolling circle amplification and primer extension
sequencing primer T7
SEQ ID NO: 147
TAATACGACTCACTATAGG rolling circle amplification and primer extension -continued sequencing primer T7 term
SEQ ID NO: 148
GCTAGTTATTGCTCAGCG Site directed mutagenesis variant SP-00067_V422
sense oligo
SEQ ID NO: 149
CGTTGGCAGCAGGGTAATTAGTTCAGCTGCAGCGTTATG Site directed mutagenesis variant SP-00067 V422
antisense oligo
SEQ ID NO: 150
CATAACGCTGCAGCTGAACTAATTACCCTGCTGCCAACG Site directed mutagenesis variant SP-00127_S415
sense oligo
SEQ ID NO: 151
GCAAGCTGACCGTCGATAAATAGCGTTGGCAGCAGGGTAATG Site directed mutagenesis variant
SP-00127_S415 antisense oligo
SEQ ID NO: 152
CATTACCCTGCTGCCAACGCTATTTATCGACGGTCAGCTTGC Site directed mutagenesis variant
SP-00128_Q418 sense oligo
SEQ ID NO: 153
CGATAAAAGCCGTTGGTAGCAGGGTAATGTGTTCAG Site directed mutagenesis variant
SP-00128_Q418 antisense oligo
SEQ ID NO: 154
CTGAACACATTACCCTGCTACCAACGGCTTTTATCG Site directed mutagenesis variant
SP-00114_P343 sense oligo
SEQ ID NO: 155
GCAAAGCGAAAGGCCAATAGCGTGAACCGCAGGTC Site directed mutagenesis variant
SP-00114_P343 antisense oligo
SEQ ID NO: 156
GACCTGCGGTTCACGCTATTGGCCTTTCGCTTTGC Site directed mutagenesis variant
SP-00112_G341 sense oligo
SEQ ID NO: 157
GACGATCAGCAAAGCGAAATAGCAACCGCGTGAACCGCAG Site directed mutagenesis variant
SP-00112_G341 antisense oligo
SEQ ID NO: 158
CTGCGGTTCACGCGGTTGCTATTTCGCTTTGCTGATCGTC Site directed mutagenesis variant
SP-00102_K320 sense oligo
SEQ ID NO: 159
GCTGAATGGTAAAGAATACTAGTGCAAAGTGAGCAACAAGG Site directed mutagenesis variant
SP-00102_K320 antisense oligo
SEQ ID NO: 160
CCTTGTTGCTCACTTTGCACTAGTATTCTTTACCATTCAGC Site directed mutagenesis variant
SP-00066_F404 sense oligo
SEQ ID NO: 161
CTGGACAGCGACGGTAGCTAGTTTCTGTATAGCAAGCTG Site directed mutagenesis variant
SP-00066_F404 antisense oligo
SEQ ID NO: 162
CAGCTTGCTATACAGAAACTAGCTACCGTCGCTGTCCAG Site directed mutagenesis variant
SP-00113_Q342 sense oligo
SEQ ID NO: 163
GCAAAGCGAAAGGCTAGCCGCGTGAACCGCAG Site directed mutagenesis variant
SP-00113_Q342 antisense oligo -continued

SEQ ID NO: 164
CTGCGGTTCACGCGGCTAGCCTTTCGCTTTGC

Site directed mutagenesis variant
SP-00096_T299 sense oligo
SEQ ID NO: 165
GTGAGGAACAATACAATAGCTAGTATCGCGTAGTGAGCGTGC Site directed mutagenesis variant
SP-00096_T299 antisense oligo
SEQ ID NO: 166
GCACGCTCACTACGCGATACTAGCTATTGTATTGTTCCTCAC Site directed mutagenesis variant
SP-00120_Y373 sense oligo
SEQ ID NO: 167
GGTGAAGGGCTTTTAGCCGAGCGACATCGC Site directed mutagenesis variant
SP-00120_Y373 antisense oligo
SEQ ID NO: 168
GCGATGTCGCTCGGCTAAAAGCCCTTCACC Site directed mutagenesis variant
SP-00094_N297 sense oligo
SEQ ID NO: 169
CGCGTGAGGAACAATACTAGAGCACGTATCGCGTAGTG Site directed mutagenesis variant
SP-00094_N297 antisense oligo
SEQ ID NO: 170
CACTACGCGATACGTGCTCTAGTATTGTTCCTCACGCG Site directed mutagenesis variant
SP-00125_F405 sense oligo
SEQ ID NO: 171
GACAGCGACGGTAGCTTCTAGCTGTATAGCAAGCTGAC Site directed mutagenesis variant
SP-00125_F405 antisense oligo
SEQ ID NO: 172
GTCAGCTTGCTATACAGCTAGAAGCTACCGTCGCTGTC

---

SEQUENCE LISTING

<160> NUMBER OF SEQ ID NOS: 172

<210> SEQ ID NO 1
<211> LENGTH: 360
<212> TYPE: PRT
<213> ORGANISM: Escherichia coli
<220> FEATURE:
<223> OTHER INFORMATION: Release Factor 1 (RF1)

<400> SEQUENCE: 1

Met Lys Pro Ser Ile Val Ala Lys Leu Glu Ala Leu His Glu Arg His
1               5                   10                  15

Glu Glu Val Gln Ala Leu Leu Gly Asp Ala Gln Thr Ile Ala Asp Gln
                20                  25                  30

Glu Arg Phe Arg Ala Leu Ser Arg Glu Tyr Ala Gln Leu Ser Asp Val
            35                  40                  45

Ser Arg Cys Phe Thr Asp Trp Gln Gln Val Gln Glu Asp Ile Glu Thr
        50                  55                  60

Ala Gln Met Met Leu Asp Asp Pro Glu Met Arg Glu Met Ala Gln Asp
65                  70                  75                  80

Glu Leu Arg Glu Ala Lys Glu Lys Ser Glu Gln Leu Glu Gln Gln Leu
                85                  90                  95

Gln Val Leu Leu Leu Pro Lys Asp Pro Asp Asp Glu Arg Asn Ala Phe
            100                 105                 110

Leu Glu Val Arg Ala Gly Thr Gly Gly Asp Glu Ala Ala Leu Phe Ala
            115                 120                 125

Gly Asp Leu Phe Arg Met Tyr Ser Arg Tyr Ala Glu Ala Arg Arg Trp
130                 135                 140

Arg Val Glu Ile Met Ser Ala Ser Gly Glu His Gly Gly Tyr Lys
145                 150                 155                 160

Glu Ile Ile Ala Lys Ile Ser Gly Asp Gly Val Tyr Gly Arg Leu Lys
                165                 170                 175

Phe Glu Ser Gly Gly His Arg Val Gln Arg Val Pro Ala Thr Glu Ser
            180                 185                 190

Gln Gly Arg Ile His Thr Ser Ala Cys Thr Val Ala Val Met Pro Glu
        195                 200                 205

Leu Pro Asp Ala Glu Leu Pro Asp Ile Asn Pro Ala Asp Leu Arg Ile
    210                 215                 220

Asp Thr Phe Arg Ser Ser Gly Ala Gly Gly Gln His Val Asn Thr Thr
225                 230                 235                 240

Asp Ser Ala Ile Arg Ile Thr His Leu Pro Thr Gly Ile Val Val Glu
                245                 250                 255

Cys Gln Asp Glu Arg Ser Gln His Lys Asn Lys Ala Lys Ala Leu Ser
            260                 265                 270

Val Leu Gly Ala Arg Ile His Ala Ala Glu Met Ala Lys Arg Gln Gln
    275                 280                 285

Ala Glu Ala Ser Thr Arg Arg Asn Leu Leu Gly Ser Gly Asp Arg Ser
        290                 295                 300

Asp Arg Asn Arg Thr Tyr Asn Phe Pro Gln Gly Arg Val Thr Asp His
305                 310                 315                 320

Arg Ile Asn Leu Thr Leu Tyr Arg Leu Asp Glu Val Met Glu Gly Lys
                325                 330                 335

Leu Asp Met Leu Ile Glu Pro Ile Ile Gln Glu His Gln Ala Asp Gln
            340                 345                 350

Leu Ala Ala Leu Ser Glu Gln Glu
        355                 360

<210> SEQ ID NO 2
<211> LENGTH: 365
<212> TYPE: PRT
<213> ORGANISM: Escherichia coli
<220> FEATURE:
<223> OTHER INFORMATION: Release Factor 2 (RF2)

<400> SEQUENCE: 2

Met Phe Glu Ile Asn Pro Val Asn Asn Arg Ile Gln Asp Leu Thr Glu
1               5                   10                  15

Arg Ser Asp Val Leu Arg Gly Tyr Leu Asp Tyr Asp Ala Lys Lys Glu
                20                  25                  30

Arg Leu Glu Glu Val Asn Ala Glu Leu Glu Gln Pro Asp Val Trp Asn
            35                  40                  45

Glu Pro Glu Arg Ala Gln Ala Leu Gly Lys Glu Arg Ser Ser Leu Glu
        50                  55                  60

Ala Val Val Asp Thr Leu Asp Gln Met Lys Gln Gly Leu Glu Asp Val
65                  70                  75                  80

Ser Gly Leu Leu Glu Leu Ala Val Glu Ala Asp Asp Glu Glu Thr Phe
                85                  90                  95

Asn Glu Ala Val Ala Glu Leu Asp Ala Leu Glu Glu Lys Leu Ala Gln
            100                 105                 110

Leu Glu Phe Arg Arg Met Phe Ser Gly Glu Tyr Asp Ser Ala Asp Cys
            115                 120                 125

Tyr Leu Asp Ile Gln Ala Gly Ser Gly Gly Thr Glu Ala Gln Asp Trp
130                 135                 140

Ala Ser Met Leu Glu Arg Met Tyr Leu Arg Trp Ala Glu Ser Arg Gly
145                 150                 155                 160

Phe Lys Thr Glu Ile Ile Glu Ser Glu Glu Val Ala Gly Ile
                165                 170                 175

Lys Ser Val Thr Ile Lys Ile Ser Gly Asp Tyr Ala Tyr Gly Trp Leu
                180                 185                 190

Arg Thr Glu Thr Gly Val His Arg Leu Val Arg Lys Ser Pro Phe Asp
            195                 200                 205

Ser Gly Gly Arg Arg His Thr Ser Phe Ser Ser Ala Phe Val Tyr Pro
        210                 215                 220

Glu Val Asp Asp Asp Ile Asp Ile Glu Ile Asn Pro Ala Asp Leu Arg
225                 230                 235                 240

Ile Asp Val Tyr Arg Thr Ser Gly Ala Gly Gln His Val Asn Arg
                245                 250                 255

Thr Glu Ser Ala Val Arg Ile Thr His Ile Pro Thr Gly Ile Val Thr
            260                 265                 270

Gln Cys Gln Asn Asp Arg Ser Gln His Lys Asn Lys Asp Gln Ala Met
        275                 280                 285

Lys Gln Met Lys Ala Lys Leu Tyr Glu Leu Glu Met Gln Lys Lys Asn
            290                 295                 300

Ala Glu Lys Gln Ala Met Glu Asp Asn Lys Ser Asp Ile Gly Trp Gly
305                 310                 315                 320

Ser Gln Ile Arg Ser Tyr Val Leu Asp Asp Ser Arg Ile Lys Asp Leu
                325                 330                 335

Arg Thr Gly Val Glu Thr Arg Asn Thr Gln Ala Val Leu Asp Gly Ser
            340                 345                 350

Leu Asp Gln Phe Ile Glu Ala Ser Leu Lys Ala Gly Leu
        355                 360                 365

<210> SEQ ID NO 3
<211> LENGTH: 317
<212> TYPE: PRT
<213> ORGANISM: Escherichia coli
<220> FEATURE:
<223> OTHER INFORMATION: Outer Membrane Protein T1 (OmpT1)
<220> FEATURE:
<221> NAME/KEY: SIGNAL
<222> LOCATION: (1)...(20)
<223> OTHER INFORMATION: signal peptide

<400> SEQUENCE: 3

Met Arg Ala Lys Leu Leu Gly Ile Val Leu Thr Thr Pro Ile Ala Ile
-20                 -15                 -10                 -5

Ser Ser Phe Ala Ser Thr Glu Thr Leu Ser Phe Thr Pro Asp Asn Ile
                1                   5                   10

Asn Ala Asp Ile Ser Leu Gly Thr Leu Ser Gly Lys Thr Lys Glu Arg
            15                  20                  25

Val Tyr Leu Ala Glu Glu Gly Gly Arg Lys Val Ser Gln Leu Asp Trp
        30                  35                  40

Lys Phe Asn Asn Ala Ala Ile Ile Lys Gly Ala Ile Asn Trp Asp Leu
45                  50                  55                  60

Met Pro Gln Ile Ser Ile Gly Ala Ala Gly Trp Thr Thr Leu Gly Ser
                65                  70                  75

-continued

```
Arg Gly Gly Asn Met Val Asp Gln Asp Trp Met Asp Ser Ser Asn Pro
            80                  85                  90
Gly Thr Trp Thr Asp Glu Ser Arg His Pro Asp Thr Gln Leu Asn Tyr
        95                 100                 105
Ala Asn Glu Phe Asp Leu Asn Ile Lys Gly Trp Leu Leu Asn Glu Pro
    110                 115                 120
Asn Tyr Arg Leu Gly Leu Met Ala Gly Tyr Gln Glu Ser Arg Tyr Ser
125                 130                 135                 140
Phe Thr Ala Arg Gly Gly Ser Tyr Ile Tyr Ser Ser Glu Glu Gly Phe
                145                 150                 155
Arg Asp Asp Ile Gly Ser Phe Pro Asn Gly Glu Arg Ala Ile Gly Tyr
            160                 165                 170
Lys Gln Arg Phe Lys Met Pro Tyr Ile Gly Leu Thr Gly Ser Tyr Arg
        175                 180                 185
Tyr Glu Asp Phe Glu Leu Gly Gly Thr Phe Lys Tyr Ser Gly Trp Val
    190                 195                 200
Glu Ser Ser Asp Asn Asp Glu His Tyr Asp Pro Gly Lys Arg Ile Thr
205                 210                 215                 220
Tyr Arg Ser Lys Val Lys Asp Gln Asn Tyr Tyr Ser Val Ala Val Asn
                225                 230                 235
Ala Gly Tyr Tyr Val Thr Pro Asn Ala Lys Val Tyr Val Glu Gly Ala
            240                 245                 250
Trp Asn Arg Val Thr Asn Lys Lys Gly Asn Thr Ser Leu Tyr Asp His
        255                 260                 265
Asn Asn Asn Thr Ser Asp Tyr Ser Lys Asn Gly Ala Gly Ile Glu Asn
270                 275                 280
Tyr Asn Phe Ile Thr Thr Ala Gly Leu Lys Tyr Thr Phe
285                 290                 295

<210> SEQ ID NO 4
<211> LENGTH: 18
<212> TYPE: PRT
<213> ORGANISM: Artificial Sequence
<220> FEATURE:
<223> OTHER INFORMATION: synthetic switch loop region of Release Factor
      1 (RF1), amino acids 287 to 304

<400> SEQUENCE: 4

Gln Gln Ala Glu Ala Ser Thr Arg Arg Asn Leu Leu Gly Ser Gly Asp
1               5                   10                  15

Arg Ser

<210> SEQ ID NO 5
<211> LENGTH: 18
<212> TYPE: PRT
<213> ORGANISM: Artificial Sequence
<220> FEATURE:
<223> OTHER INFORMATION: synthetic N296K mutation in the switch loop
      region of Release Factor 1 (RF1), amino acids 287 to 304

<400> SEQUENCE: 5

Gln Gln Ala Glu Ala Ser Thr Arg Arg Lys Leu Leu Gly Ser Gly Asp
1               5                   10                  15

Arg Ser

<210> SEQ ID NO 6
<211> LENGTH: 18
<212> TYPE: PRT
```

<213> ORGANISM: Artificial Sequence
<220> FEATURE:
<223> OTHER INFORMATION: synthetic N296R mutation in the switch loop
      region of Release Factor 1 (RF1), amino acids 287 to 304

<400> SEQUENCE: 6

Gln Gln Ala Glu Ala Ser Thr Arg Arg Arg Leu Leu Gly Ser Gly Asp
1               5                  10                  15

Arg Ser

<210> SEQ ID NO 7
<211> LENGTH: 18
<212> TYPE: PRT
<213> ORGANISM: Artificial Sequence
<220> FEATURE:
<223> OTHER INFORMATION: synthetic L297K mutation in the switch loop
      region of Release Factor 1 (RF1), amino acids 287 to 304

<400> SEQUENCE: 7

Gln Gln Ala Glu Ala Ser Thr Arg Arg Asn Lys Leu Gly Ser Gly Asp
1               5                  10                  15

Arg Ser

<210> SEQ ID NO 8
<211> LENGTH: 18
<212> TYPE: PRT
<213> ORGANISM: Artificial Sequence
<220> FEATURE:
<223> OTHER INFORMATION: synthetic L297R mutation in the switch loop
      region of Release Factor 1 (RF1), amino acids 287 to 304

<400> SEQUENCE: 8

Gln Gln Ala Glu Ala Ser Thr Arg Arg Asn Arg Leu Gly Ser Gly Asp
1               5                  10                  15

Arg Ser

<210> SEQ ID NO 9
<211> LENGTH: 18
<212> TYPE: PRT
<213> ORGANISM: Artificial Sequence
<220> FEATURE:
<223> OTHER INFORMATION: synthetic L297V mutation in the switch loop
      region of Release Factor 1 (RF1), amino acids 287 to 304

<400> SEQUENCE: 9

Gln Gln Ala Glu Ala Ser Thr Arg Arg Asn Val Leu Gly Ser Gly Asp
1               5                  10                  15

Arg Ser

<210> SEQ ID NO 10
<211> LENGTH: 18
<212> TYPE: PRT
<213> ORGANISM: Artificial Sequence
<220> FEATURE:
<223> OTHER INFORMATION: synthetic L298K mutation in the switch loop
      region of Release Factor 1 (RF1), amino acids 287 to 304

<400> SEQUENCE: 10

Gln Gln Ala Glu Ala Ser Thr Arg Arg Asn Leu Lys Gly Ser Gly Asp
1               5                  10                  15

Arg Ser

<210> SEQ ID NO 11
<211> LENGTH: 18

```
<212> TYPE: PRT
<213> ORGANISM: Artificial Sequence
<220> FEATURE:
<223> OTHER INFORMATION: synthetic L298R mutation in the switch loop
      region of Release Factor 1 (RF1), amino acids 287 to 304

<400> SEQUENCE: 11

Gln Gln Ala Glu Ala Ser Thr Arg Arg Asn Leu Arg Gly Ser Gly Asp
1               5                   10                  15

Arg Ser

<210> SEQ ID NO 12
<211> LENGTH: 18
<212> TYPE: PRT
<213> ORGANISM: Artificial Sequence
<220> FEATURE:
<223> OTHER INFORMATION: synthetic N296K,L297K mutation in the switch
      loop region of Release Factor 1 (RF1), amino acids 287 to 304

<400> SEQUENCE: 12

Gln Gln Ala Glu Ala Ser Thr Arg Arg Lys Lys Leu Gly Ser Gly Asp
1               5                   10                  15

Arg Ser

<210> SEQ ID NO 13
<211> LENGTH: 18
<212> TYPE: PRT
<213> ORGANISM: Artificial Sequence
<220> FEATURE:
<223> OTHER INFORMATION: synthetic N296K,L297R = A13 mutation in the
      switch loop region of Release Factor 1 (RF1), amino acids 287 to
      304

<400> SEQUENCE: 13

Gln Gln Ala Glu Ala Ser Thr Arg Arg Lys Arg Leu Gly Ser Gly Asp
1               5                   10                  15

Arg Ser

<210> SEQ ID NO 14
<211> LENGTH: 18
<212> TYPE: PRT
<213> ORGANISM: Artificial Sequence
<220> FEATURE:
<223> OTHER INFORMATION: synthetic N296K,L297V mutation in the switch
      loop region of Release Factor 1 (RF1), amino acids 287 to 304

<400> SEQUENCE: 14

Gln Gln Ala Glu Ala Ser Thr Arg Arg Lys Val Leu Gly Ser Gly Asp
1               5                   10                  15

Arg Ser

<210> SEQ ID NO 15
<211> LENGTH: 18
<212> TYPE: PRT
<213> ORGANISM: Artificial Sequence
<220> FEATURE:
<223> OTHER INFORMATION: synthetic N296K,L297V mutation in the switch
      loop region of Release Factor 1 (RF1), amino acids 287 to 304

<400> SEQUENCE: 15

Gln Gln Ala Glu Ala Ser Thr Arg Arg Lys Leu Gly Ser Gly Asp
1               5                   10                  15

Arg Ser
```

```
<210> SEQ ID NO 16
<211> LENGTH: 18
<212> TYPE: PRT
<213> ORGANISM: Artificial Sequence
<220> FEATURE:
<223> OTHER INFORMATION: synthetic N296R,L297R mutation in the switch
      loop region of Release Factor 1 (RF1), amino acids 287 to 304

<400> SEQUENCE: 16

Gln Gln Ala Glu Ala Ser Thr Arg Arg Arg Arg Leu Gly Ser Gly Asp
1               5                   10                  15

Arg Ser

<210> SEQ ID NO 17
<211> LENGTH: 18
<212> TYPE: PRT
<213> ORGANISM: Artificial Sequence
<220> FEATURE:
<223> OTHER INFORMATION: synthetic N296R,L297V mutation in the switch
      loop region of Release Factor 1 (RF1), amino acids 287 to 304

<400> SEQUENCE: 17

Gln Gln Ala Glu Ala Ser Thr Arg Arg Arg Val Leu Gly Ser Gly Asp
1               5                   10                  15

Arg Ser

<210> SEQ ID NO 18
<211> LENGTH: 18
<212> TYPE: PRT
<213> ORGANISM: Artificial Sequence
<220> FEATURE:
<223> OTHER INFORMATION: synthetic N296K,L297K,L298K mutation in the
      switch loop region of Release Factor 1 (RF1), amino acids 287 to
      304

<400> SEQUENCE: 18

Gln Gln Ala Glu Ala Ser Thr Arg Arg Lys Lys Lys Gly Ser Gly Asp
1               5                   10                  15

Arg Ser

<210> SEQ ID NO 19
<211> LENGTH: 18
<212> TYPE: PRT
<213> ORGANISM: Artificial Sequence
<220> FEATURE:
<223> OTHER INFORMATION: synthetic N296K,L297K,L298R mutation in the
      switch loop region of Release Factor 1 (RF1), amino acids 287 to
      304

<400> SEQUENCE: 19

Gln Gln Ala Glu Ala Ser Thr Arg Arg Lys Lys Arg Gly Ser Gly Asp
1               5                   10                  15

Arg Ser

<210> SEQ ID NO 20
<211> LENGTH: 18
<212> TYPE: PRT
<213> ORGANISM: Artificial Sequence
<220> FEATURE:
<223> OTHER INFORMATION: synthetic N296K,L297R,L298K = A17 mutation in
      the switch loop region of Release Factor 1 (RF1), amino acids 287
      to 304

<400> SEQUENCE: 20

Gln Gln Ala Glu Ala Ser Thr Arg Arg Lys Arg Lys Gly Ser Gly Asp
1               5                   10                  15
```

Arg Ser

<210> SEQ ID NO 21
<211> LENGTH: 18
<212> TYPE: PRT
<213> ORGANISM: Artificial Sequence
<220> FEATURE:
<223> OTHER INFORMATION: synthetic N296K,L297R,L298R = A18 mutation in
      the switch loop region of Release Factor 1 (RF1), amino acids 287
      to 304

<400> SEQUENCE: 21

Gln Gln Ala Glu Ala Ser Thr Arg Arg Lys Arg Arg Gly Ser Gly Asp
1               5                   10                  15

Arg Ser

<210> SEQ ID NO 22
<211> LENGTH: 18
<212> TYPE: PRT
<213> ORGANISM: Artificial Sequence
<220> FEATURE:
<223> OTHER INFORMATION: synthetic N296R,L297R,L298R mutation in the
      switch loop region of Release Factor 1 (RF1), amino acids 287 to
      304

<400> SEQUENCE: 22

Gln Gln Ala Glu Ala Ser Thr Arg Arg Arg Arg Arg Gly Ser Gly Asp
1               5                   10                  15

Arg Ser

<210> SEQ ID NO 23
<211> LENGTH: 18
<212> TYPE: PRT
<213> ORGANISM: Artificial Sequence
<220> FEATURE:
<223> OTHER INFORMATION: synthetic N296R,L297K,L298R mutation in the
      switch loop region of Release Factor 1 (RF1), amino acids 287 to
      304

<400> SEQUENCE: 23

Gln Gln Ala Glu Ala Ser Thr Arg Arg Arg Lys Arg Gly Ser Gly Asp
1               5                   10                  15

Arg Ser

<210> SEQ ID NO 24
<211> LENGTH: 18
<212> TYPE: PRT
<213> ORGANISM: Artificial Sequence
<220> FEATURE:
<223> OTHER INFORMATION: synthetic N296R,L297R,L298K mutation in the
      switch loop region of Release Factor 1 (RF1), amino acids 287 to
      304

<400> SEQUENCE: 24

Gln Gln Ala Glu Ala Ser Thr Arg Arg Arg Lys Gly Ser Gly Asp
1               5                   10                  15

Arg Ser

<210> SEQ ID NO 25
<211> LENGTH: 18
<212> TYPE: PRT
<213> ORGANISM: Artificial Sequence
<220> FEATURE:
<223> OTHER INFORMATION: synthetic N296R,L297K,L298K mutation in the
      switch loop region of Release Factor 1 (RF1), amino acids 287 to

304

<400> SEQUENCE: 25

Gln Gln Ala Glu Ala Ser Thr Arg Arg Lys Lys Gly Ser Gly Asp
1               5                   10                  15

Arg Ser

<210> SEQ ID NO 26
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 26

Gln Ala Arg Arg Gly Ser Thr Arg Arg Asn Leu Leu Gly Ser Gly Asp
1               5                   10                  15

Arg Ser

<210> SEQ ID NO 27
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 27

Gln Gln Ala Arg Arg Gly Thr Arg Arg Asn Leu Leu Gly Ser Gly Asp
1               5                   10                  15

Arg Ser

<210> SEQ ID NO 28
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 28

Gln Gln Ala Ala Arg Arg Gly Arg Arg Asn Leu Leu Gly Ser Gly Asp
1               5                   10                  15

Arg Ser

<210> SEQ ID NO 29
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 29

Gln Gln Ala Glu Ala Arg Arg Gly Arg Asn Leu Leu Gly Ser Gly Asp
1               5                   10                  15

Arg Ser

<210> SEQ ID NO 30

-continued

```
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 30

Gln Gln Ala Glu Ala Ala Arg Arg Gly Asn Leu Leu Gly Ser Gly Asp
1               5                   10                  15

Arg Ser

<210> SEQ ID NO 31
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 31

Gln Gln Ala Glu Ala Ser Ala Arg Arg Gly Leu Leu Gly Ser Gly Asp
1               5                   10                  15

Arg Ser

<210> SEQ ID NO 32
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 32

Gln Gln Ala Glu Ala Ser Thr Ala Arg Arg Gly Leu Gly Ser Gly Asp
1               5                   10                  15

Arg Ser

<210> SEQ ID NO 33
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 33

Gln Gln Ala Glu Ala Ser Thr Arg Ala Arg Arg Gly Gly Ser Gly Asp
1               5                   10                  15

Arg Ser

<210> SEQ ID NO 34
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 34

Gln Gln Ala Glu Ala Ser Thr Arg Arg Ala Arg Arg Gly Ser Gly Asp
```

<210> SEQ ID NO 35
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 35

Gln Gln Ala Glu Ala Ser Thr Arg Arg Asn Ala Arg Arg Gly Gly Asp
1               5                   10                  15

Arg Ser

<210> SEQ ID NO 36
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 36

Gln Gln Ala Glu Ala Ser Thr Arg Arg Asn Leu Ala Arg Arg Gly Asp
1               5                   10                  15

Arg Ser

<210> SEQ ID NO 37
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 37

Gln Gln Ala Glu Ala Ser Thr Arg Arg Asn Leu Leu Ala Arg Arg Gly
1               5                   10                  15

Arg Ser

<210> SEQ ID NO 38
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 38

Gln Gln Ala Glu Ala Ser Thr Arg Arg Asn Leu Leu Gly Ala Arg Arg
1               5                   10                  15

Gly Ser

<210> SEQ ID NO 39
<211> LENGTH: 18
<212> TYPE: PRT
<213> ORGANISM: Artificial Sequence
<220> FEATURE:
<223> OTHER INFORMATION: synthetic OmpT cleavage peptide sequence inserted in the switch loop region of Release Factor 1
(RF1), amino acids 287 to 304

<400> SEQUENCE: 39

Gln Gln Ala Glu Ala Ser Thr Arg Arg Asn Leu Leu Gly Ser Ala Arg
1               5                   10                  15

Arg Gly

<210> SEQ ID NO 40
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 40

Gln Gln Ala Glu Ala Ser Thr Arg Arg Asn Leu Leu Gly Ser Gly Ala
1               5                   10                  15

Arg Arg

<210> SEQ ID NO 41
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 41

Gln Gln Ala Trp Leu Ala Ala Arg Arg Gly Arg Gly Gly Ser Gly Asp
1               5                   10                  15

Arg Ser

<210> SEQ ID NO 42
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 42

Gln Gln Ala Glu Trp Leu Ala Ala Arg Arg Gly Arg Gly Ser Gly Asp
1               5                   10                  15

Arg Ser

<210> SEQ ID NO 43
<211> LENGTH: 18
<212> TYPE: PRT
<213> ORGANISM: Artificial Sequence
<220> FEATURE:
<223> OTHER INFORMATION: synthetic OmpT cleavage peptide sequence
      inserted in the switch loop region of Release Factor 1
      (RF1), amino acids 287 to 304

<400> SEQUENCE: 43

Gln Gln Ala Glu Ala Trp Leu Ala Ala Arg Arg Gly Arg Gly Gly Asp
1               5                   10                  15

Arg Ser

```
<210> SEQ ID NO 44
<211> LENGTH: 18
<212> TYPE: PRT
<213> ORGANISM: Artificial Sequence
<220> FEATURE:
<223> OTHER INFOR

```
<212> TYPE: PRT
<213> ORGANISM: Artificial Sequence
<220> FEATURE:
<223> OTHER INFORMATION: synthetic OmpT cleavage peptide

<400> SEQUENCE: 49

Trp Gly Gly Arg Trp Ala Arg Lys Lys Gly Thr Ile
1               5                   10

<210> SEQ ID NO 50
<211> LENGTH: 9
<212> TYPE: PRT
<213> ORGANISM: Artificial Sequence
<220> FEATURE:
<223> OTHER INFORMATION: synthetic C-terminal sequence of short form of
      lambda phage Gam protein (GamS)

<400> SEQUENCE: 50

Gly Gly Ser His His His His His His
1               5

<210> SEQ ID NO 51
<211> LENGTH: 42
<212> TYPE: DNA
<213> ORGANISM: Artificial Sequence
<220> FEATURE:
<223> OTHER INFORMATION: synthetic short form of lambda phage Gam
      protein (GamS) gene amplification primer

<400> SEQUENCE: 51
atatatcata tgaacgctta ttacattcag gatcgtcttg ag                           42

<210> SEQ ID NO 52
<211> LENGTH: 72
<212> TYPE: DNA
<213> ORGANISM: Artificial Sequence
<220> FEATURE:
<223> OTHER INFORMATION: synthetic short form of lambda phage Gam
      protein (GamS) gene amplification primer

<400> SEQUENCE: 52
atatatgtcg acttaatgat gatgatgatg atgagaaccc cctacctctg aatcaatatc        60
aacctggtgg tg                                                            72

<210> SEQ ID NO 53
<211> LENGTH: 58
<212> TYPE: DNA
<213> ORGANISM: Artificial Sequence
<220> FEATURE:
<223> OTHER INFORMATION: synthetic 5'-fragment including T7 promoter,
      constant region of the N-terminal sequence and the mutation site
      first step PCR amplification oligo primer 5chiT2PT7

<400> SEQUENCE: 53
gcgtactagc gtaccacgtg gctggtggcc gattcattaa tgcagctggc acgacagg          58

<210> SEQ ID NO 54
<211> LENGTH: 60
<212> TYPE: DNA
<213> ORGANISM: Artificial Sequence
<220> FEATURE:
<223> OTHER INFORMATION: synthetic 3'-fragment including mutation site,
      constant C-terminal region and T7 terminator sequences first step
      PCR amplification oligo primer 3chiT2TT7

<400> SEQUENCE: 54
gcgtactagc gtaccacgtg gctggtggcg gtgagttttc tccttcatta cagaaacggc        60
```

<210> SEQ ID NO 55
<211> LENGTH: 28
<212> TYPE: DNA
<213> ORGANISM: Artificial Sequence
<220> FEATURE:
<223> OTHER INFORMATION: synthetic 5'-fragment and 3'-fragment assembly
      overlapping second step PCR single primer 5chiT2

<400> SEQUENCE: 55
gcgtactagc gtaccacgtg gctggtgg                                       28

<210> SEQ ID NO 56
<211> LENGTH: 35
<212> TYPE: DNA
<213> ORGANISM: Artificial Sequence
<220> FEATURE:
<223> OTHER INFORMATION: synthetic WT RF1 variant OmpT cleavage site
      screening forward primer

<400> SEQUENCE: 56
gctcgatgat cctgaaatgc gtgagatggc gcagg                               35

<210> SEQ ID NO 57
<211> LENGTH: 35
<212> TYPE: DNA
<213> ORGANISM: Artificial Sequence
<220> FEATURE:
<223> OTHER INFORMATION: synthetic M74R RF1 variant OmpT cleavage site
      screening forward primer

<400> SEQUENCE: 57
gctcgatgat cctgaacgcc gtgagatggc gcagg                               35

<210> SEQ ID NO 58
<211> LENGTH: 38
<212> TYPE: DNA
<213> ORGANISM: Artificial Sequence
<220> FEATURE:
<223> OTHER INFORMATION: synthetic E76K RF1 variant OmpT cleavage site
      screening forward primer

<400> SEQUENCE: 58
cgatgatcct gaaatgcgta agatggcgca ggatgaac                            38

<210> SEQ ID NO 59
<211> LENGTH: 40
<212> TYPE: DNA
<213> ORGANISM: Artificial Sequence
<220> FEATURE:
<223> OTHER INFORMATION: synthetic E84K RF1 variant OmpT cleavage site
      screening forward primer

<400> SEQUENCE: 59
caggatgaac tgcgcaaagc taaagaaaaa agcgagcaac                          40

<210> SEQ ID NO 60
<211> LENGTH: 40
<212> TYPE: DNA
<213> ORGANISM: Artificial Sequence
<220> FEATURE:
<223> OTHER INFORMATION: synthetic A85R RF1 variant OmpT cleavage site
      screening forward primer

<400> SEQUENCE: 60
caggatgaac tgcgcgaacg taaagaaaaa agcgagcaac                          40

<210> SEQ ID NO 61
<211> LENGTH: 44
<212> TYPE: DNA
<213> ORGANISM: Artificial Sequence
<220> FEATURE:
<223> OTHER INFORMATION: synthetic E87R RF1 variant OmpT cleavage site
      screening forward primer

<400> SEQUENCE: 61
ggatgaactg cgcgaagcta aacgtaaaag cgagcaactg gaac                    44

<210> SEQ ID NO 62
<211> LENGTH: 38
<212> TYPE: DNA
<213> ORGANISM: Artificial Sequence
<220> FEATURE:
<223> OTHER INFORMATION: synthetic E108R RF1 variant OmpT cleavage site
      screening forward primer

<400> SEQUENCE: 62
gccaaaagat cctgatgacc gtcgtaacgc cttcctcg                           38

<210> SEQ ID NO 63
<211> LENGTH: 34
<212> TYPE: DNA
<213> ORGANISM: Artificial Sequence
<220> FEATURE:
<223> OTHER INFORMATION: synthetic T293R RF1 variant OmpT cleavage site
      screening forward primer

<400> SEQUENCE: 63
caacaggccg aagcgtctcg ccgtcgtaac ctgc                               34

<210> SEQ ID NO 64
<211> LENGTH: 34
<212> TYPE: DNA
<213> ORGANISM: Artificial Sequence
<220> FEATURE:
<223> OTHER INFORMATION: synthetic N296K RF1 variant OmpT cleavage site
      screening forward primer

<400> SEQUENCE: 64
gcgtctaccc gtcgtaaact gctggggagt ggcg                               34

<210> SEQ ID NO 65
<211> LENGTH: 36
<212> TYPE: DNA
<213> ORGANISM: Artificial Sequence
<220> FEATURE:
<223> OTHER INFORMATION: synthetic S304K RF1 variant OmpT cleavage site
      screening forward primer

<400> SEQUENCE: 65
gggagtggcg atcgcaagga ccgtaaccgt acttac                             36

<210> SEQ ID NO 66
<211> LENGTH: 46
<212> TYPE: DNA
<213> ORGANISM: Artificial Sequence
<220> FEATURE:
<223> OTHER INFORMATION: synthetic N296K/L297V RF1 variant OmpT cleavage
      site screening forward primer

<400> SEQUENCE: 66
cgaagcgtct acccgtcgta aagttctggg gagtggcgat cgcagc                  46

<210> SEQ ID NO 67
<211> LENGTH: 46
<212> TYPE: DNA
<213> ORGANISM: Artificial Sequence
<220> FEATURE:
<223> OTHER INFORMATION: synthetic N296K/L297K RF1 variant OmpT cleavage
      site screening forward primer

<400> SEQUENCE: 67
cgaagcgtct acccgtcgta aaaagctggg gagtggcgat cgcagc         46

<210> SEQ ID NO 68
<211> LENGTH: 46
<212> TYPE: DNA
<213> ORGANISM: Artificial Sequence
<220> FEATURE:
<223> OTHER INFORMATION: synthetic N296K/L297R RF1 variant OmpT cleavage
      site screening forward primer

<400> SEQUENCE: 68
cgaagcgtct acccgtcgta aacgtctggg gagtggcgat cgcagc         46

<210> SEQ ID NO 69
<211> LENGTH: 46
<212> TYPE: DNA
<213> ORGANISM: Artificial Sequence
<220> FEATURE:
<223> OTHER INFORMATION: synthetic N296R/L297V RF1 variant OmpT cleavage
      site screening forward primer

<400> SEQUENCE: 69
cgaagcgtct acccgtcgtc gcgttctggg gagtggcgat cgcagc         46

<210> SEQ ID NO 70
<211> LENGTH: 46
<212> TYPE: DNA
<213> ORGANISM: Artificial Sequence
<220> FEATURE:
<223> OTHER INFORMATION: synthetic N296R/L297K RF1 variant OmpT cleavage
      site screening forward primer

<400> SEQUENCE: 70
cgaagcgtct acccgtcgtc gcaagctggg gagtggcgat cgcagc         46

<210> SEQ ID NO 71
<211> LENGTH: 46
<212> TYPE: DNA
<213> ORGANISM: Artificial Sequence
<220> FEATURE:
<223> OTHER INFORMATION: synthetic N296R/L297R RF1 variant OmpT cleavage
      site screening forward primer

<400> SEQUENCE: 71
cgaagcgtct acccgtcgtc gccgtctggg gagtggcgat cgcagc         46

<210> SEQ ID NO 72
<211> LENGTH: 55
<212> TYPE: DNA
<213> ORGANISM: Artificial Sequence
<220> FEATURE:
<223> OTHER INFORMATION: synthetic N296K/L297R/L298K RF1 variant OmpT
      cleavage site screening forward primer

<400> SEQUENCE: 72
caggccgaag cgtctacccg tcgtaaacgt aagggagtg gcgatcgcag cgacc         55

<210> SEQ ID NO 73

```
<211> LENGTH: 55
<212> TYPE: DNA
<213> ORGANISM: Artificial Sequence
<220> FEATURE:
<223> OTHER INFORMATION: synthetic N296K/L297R/L298R RF1 variant OmpT
      cleavage site screening forward primer

<400> SEQUENCE: 73
caggccgaag cgtctacccg tcgtaaacgt cgcgggagtg gcgatcgcag cgacc          55

<210> SEQ ID NO 74
<211> LENGTH: 35
<212> TYPE: DNA
<213> ORGANISM: Artificial Sequence
<220> FEATURE:
<223> OTHER INFORMATION: synthetic WT RF1 variant OmpT cleavage site
      screening reverse primer

<400> SEQUENCE: 74
cctgcgccat ctcacgcatt tcaggatcat cgagc                                35

<210> SEQ ID NO 75
<211> LENGTH: 35
<212> TYPE: DNA
<213> ORGANISM: Artificial Sequence
<220> FEATURE:
<223> OTHER INFORMATION: synthetic M74R RF1 variant OmpT cleavage site
      screening reverse primer

<400> SEQUENCE: 75
cctgcgccat ctcacggcgt tcaggatcat cgagc                                35

<210> SEQ ID NO 76
<211> LENGTH: 38
<212> TYPE: DNA
<213> ORGANISM: Artificial Sequence
<220> FEATURE:
<223> OTHER INFORMATION: synthetic E76K RF1 variant OmpT cleavage site
      screening reverse primer

<400> SEQUENCE: 76
gttcatcctg cgccatctta cgcatttcag gatcatcg                             38

<210> SEQ ID NO 77
<211> LENGTH: 40
<212> TYPE: DNA
<213> ORGANISM: Artificial Sequence
<220> FEATURE:
<223> OTHER INFORMATION: synthetic E84K RF1 variant OmpT cleavage site
      screening reverse primer

<400> SEQUENCE: 77
gttgctcgct tttttcttta gctttgcgca gttcatcctg                           40

<210> SEQ ID NO 78
<211> LENGTH: 40
<212> TYPE: DNA
<213> ORGANISM: Artificial Sequence
<220> FEATURE:
<223> OTHER INFORMATION: synthetic A85R RF1 variant OmpT cleavage site
      screening reverse primer

<400> SEQUENCE: 78
gttgctcgct tttttcttta cgttcgcgca gttcatcctg                           40

<210> SEQ ID NO 79
<211> LENGTH: 44
```

```
<212> TYPE: DNA
<213> ORGANISM: Artificial Sequence
<220> FEATURE:
<223> OTHER INFORMATION: synthetic E87R RF1 variant OmpT cleavage site
      screening reverse primer

<400> SEQUENCE: 79
gttccagttg ctcgcttttta cgtttagctt cgcgcagttc atcc                    44

<210> SEQ ID NO 80
<211> LENGTH: 38
<212> TYPE: DNA
<213> ORGANISM: Artificial Sequence
<220> FEATURE:
<223> OTHER INFORMATION: synthetic E108R RF1 variant OmpT cleavage site
      screening reverse primer

<400> SEQUENCE: 80
cgaggaaggc gttacgacgg tcatcaggat cttttggc                            38

<210> SEQ ID NO 81
<211> LENGTH: 34
<212> TYPE: DNA
<213> ORGANISM: Artificial Sequence
<220> FEATURE:
<223> OTHER INFORMATION: synthetic T293R RF1 variant OmpT cleavage site
      screening reverse primer

<400> SEQUENCE: 81
gcaggttacg acggcgagac gcttcggcct gttg                                34

<210> SEQ ID NO 82
<211> LENGTH: 34
<212> TYPE: DNA
<213> ORGANISM: Artificial Sequence
<220> FEATURE:
<223> OTHER INFORMATION: synthetic N296K RF1 variant OmpT cleavage site
      screening reverse primer

<400> SEQUENCE: 82
cgccactccc cagcagttta cgacgggtag acgc                                34

<210> SEQ ID NO 83
<211> LENGTH: 36
<212> TYPE: DNA
<213> ORGANISM: Artificial Sequence
<220> FEATURE:
<223> OTHER INFORMATION: synthetic S304K RF1 variant OmpT cleavage site
      screening reverse primer

<400> SEQUENCE: 83
gtaagtacgg ttacggtcct tgcgatcgcc actccc                              36

<210> SEQ ID NO 84
<211> LENGTH: 46
<212> TYPE: DNA
<213> ORGANISM: Artificial Sequence
<220> FEATURE:
<223> OTHER INFORMATION: synthetic N296K/L297V RF1 variant OmpT cleavage
      site screening reverse primer

<400> SEQUENCE: 84
gctgcgatcg ccactcccca gaactttacg acgggtagac gcttcg                   46

<210> SEQ ID NO 85
<211> LENGTH: 46
<212> TYPE: DNA
```

<210> SEQ ID NO 85
<211> LENGTH: 46
<212> TYPE: DNA
<213> ORGANISM: Artificial Sequence
<220> FEATURE:
<223> OTHER INFORMATION: synthetic N296K/L297K RF1 variant OmpT cleavage site screening reverse primer

<400> SEQUENCE: 85
gctgcgatcg ccactcccca gcttttacg acgggtagac gcttcg        46

<210> SEQ ID NO 86
<211> LENGTH: 46
<212> TYPE: DNA
<213> ORGANISM: Artificial Sequence
<220> FEATURE:
<223> OTHER INFORMATION: synthetic N296K/L297R RF1 variant OmpT cleavage site screening reverse primer

<400> SEQUENCE: 86
gctgcgatcg ccactcccca gacgtttacg acgggtagac gcttcg        46

<210> SEQ ID NO 87
<211> LENGTH: 46
<212> TYPE: DNA
<213> ORGANISM: Artificial Sequence
<220> FEATURE:
<223> OTHER INFORMATION: synthetic N296R/L297V RF1 variant OmpT cleavage site screening reverse primer

<400> SEQUENCE: 87
gctgcgatcg ccactcccca gaacgcgacg acgggtagac gcttcg        46

<210> SEQ ID NO 88
<211> LENGTH: 46
<212> TYPE: DNA
<213> ORGANISM: Artificial Sequence
<220> FEATURE:
<223> OTHER INFORMATION: synthetic N296R/L297K RF1 variant OmpT cleavage site screening reverse primer

<400> SEQUENCE: 88
gctgcgatcg ccactcccca gcttgcgacg acgggtagac gcttcg        46

<210> SEQ ID NO 89
<211> LENGTH: 46
<212> TYPE: DNA
<213> ORGANISM: Artificial Sequence
<220> FEATURE:
<223> OTHER INFORMATION: synthetic N296R/L297R RF1 variant OmpT cleavage site screening reverse primer

<400> SEQUENCE: 89
gctgcgatcg ccactcccca gacggcgacg acgggtagac gcttcg        46

<210> SEQ ID NO 90
<211> LENGTH: 55
<212> TYPE: DNA
<213> ORGANISM: Artificial Sequence
<220> FEATURE:
<223> OTHER INFORMATION: synthetic N296K/L297R/L298K RF1 variant OmpT cleavage site screening reverse primer

<400> SEQUENCE: 90
ggtcgctgcg atcgccactc cccttacgtt tacgacgggt agacgcttcg gcctg        55

<210> SEQ ID NO 91
<211> LENGTH: 55
<212> TYPE: DNA
<213> ORGANISM: Artificial Sequence

```
<220> FEATURE:
<223> OTHER INFORMATION: synthetic N296K/L297R/L298R RF1 variant OmpT
      cleavage site screening reverse primer

<400> SEQUENCE: 91
ggtcgctgcg atcgccactc ccgcgacgtt tacgacgggt agacgcttcg gcctg            55

<210> SEQ ID NO 92
<211> LENGTH: 75
<212> TYPE: DNA
<213> ORGANISM: Artificial Sequence
<220> FEATURE:
<223> OTHER INFORMATION: synthetic No. 0 RF1 variant OmpT cleavage
      peptide insertion forward oligo primer

<400> SEQUENCE: 92
gccgaagcgt ctacccgtcg taacctgctg gggagtggcg atcgcagcga ccgtaaccgt      60
acttacaact tcccg                                                       75

<210> SEQ ID NO 93
<211> LENGTH: 75
<212> TYPE: DNA
<213> ORGANISM: Artificial Sequence
<220> FEATURE:
<223> OTHER INFORMATION: synthetic No. 1 RF1 variant OmpT cleavage
      peptide insertion forward oligo primer

<400> SEQUENCE: 93
cgccgtggtt ctacccgtcg taacctgctg gggagtggcg atcgcagcga ccgtaaccgt      60
acttacaact tcccg                                                       75

<210> SEQ ID NO 94
<211> LENGTH: 75
<212> TYPE: DNA
<213> ORGANISM: Artificial Sequence
<220> FEATURE:
<223> OTHER INFORMATION: synthetic No. 2 RF1 variant OmpT cleavage
      peptide insertion forward oligo primer

<400> SEQUENCE: 94
gcacgccgtg gtacccgtcg taacctgctg gggagtggcg atcgcagcga ccgtaaccgt      60
acttacaact tcccg                                                       75

<210> SEQ ID NO 95
<211> LENGTH: 75
<212> TYPE: DNA
<213> ORGANISM: Artificial Sequence
<220> FEATURE:
<223> OTHER INFORMATION: synthetic No. 3 RF1 variant OmpT cleavage
      peptide insertion forward oligo primer

<400> SEQUENCE: 95
gccgcacgcc gtggtcgtcg taacctgctg gggagtggcg atcgcagcga ccgtaaccgt      60
acttacaact tcccg                                                       75

<210> SEQ ID NO 96
<211> LENGTH: 75
<212> TYPE: DNA
<213> ORGANISM: Artificial Sequence
<220> FEATURE:
<223> OTHER INFORMATION: synthetic No. 4 RF1 variant OmpT cleavage
      peptide insertion forward oligo primer

<400> SEQUENCE: 96
```

```
gccgaagcac gccgtggtcg taacctgctg gggagtggcg atcgcagcga ccgtaaccgt    60
acttacaact tcccg                                                    75
```

<210> SEQ ID NO 97
<211> LENGTH: 75
<212> TYPE: DNA
<213> ORGANISM: Artificial Sequence
<220> FEATURE:
<223> OTHER INFORMATION: synthetic No. 5 RF1 variant OmpT cleavage
      peptide insertion forward oligo primer

<400> SEQUENCE: 97

```
gccgaagcgg cacgccgtgg taacctgctg gggagtggcg atcgcagcga ccgtaaccgt    60
acttacaact tcccg                                                    75
```

<210> SEQ ID NO 98
<211> LENGTH: 75
<212> TYPE: DNA
<213> ORGANISM: Artificial Sequence
<220> FEATURE:
<223> OTHER INFORMATION: synthetic No. 6 RF1 variant OmpT cleavage
      peptide insertion forward oligo primer

<400> SEQUENCE: 98

```
gccgaagcgt ctgcacgccg tggtctgctg gggagtggcg atcgcagcga ccgtaaccgt    60
acttacaact tcccg                                                    75
```

<210> SEQ ID NO 99
<211> LENGTH: 75
<212> TYPE: DNA
<213> ORGANISM: Artificial Sequence
<220> FEATURE:
<223> OTHER INFORMATION: synthetic No. 7 RF1 variant OmpT cleavage
      peptide insertion forward oligo primer

<400> SEQUENCE: 99

```
gccgaagcgt ctaccgcacg ccgtggtctg gggagtggcg atcgcagcga ccgtaaccgt    60
acttacaact tcccg                                                    75
```

<210> SEQ ID NO 100
<211> LENGTH: 75
<212> TYPE: DNA
<213> ORGANISM: Artificial Sequence
<220> FEATURE:
<223> OTHER INFORMATION: synthetic No. 8 RF1 variant OmpT cleavage
      peptide insertion forward oligo primer

<400> SEQUENCE: 100

```
gccgaagcgt ctacccgtgc acgccgtggt gggagtggcg atcgcagcga ccgtaaccgt    60
acttacaact tcccg                                                    75
```

<210> SEQ ID NO 101
<211> LENGTH: 75
<212> TYPE: DNA
<213> ORGANISM: Artificial Sequence
<220> FEATURE:
<223> OTHER INFORMATION: synthetic No. 9 RF1 variant OmpT cleavage
      peptide insertion forward oligo primer

<400> SEQUENCE: 101

```
gccgaagcgt ctacccgtcg tgcacgccgt ggtagtggcg atcgcagcga ccgtaaccgt    60
acttacaact tcccg                                                    75
```

<210> SEQ ID NO 102
<211> LENGTH: 75
<212> TYPE: DNA
<213> ORGANISM: Artificial Sequence
<220> FEATURE:
<223> OTHER INFORMATION: synthetic No. 10 RF1 variant OmpT cleavage
      peptide insertion forward oligo primer

<400> SEQUENCE: 102
gccgaagcgt ctacccgtcg taacgcacgc cgtggtggcg atcgcagcga ccgtaaccgt    60
acttacaact tcccg                                                     75

<210> SEQ ID NO 103
<211> LENGTH: 75
<212> TYPE: DNA
<213> ORGANISM: Artificial Sequence
<220> FEATURE:
<223> OTHER INFORMATION: synthetic No. 11 RF1 variant OmpT cleavage
      peptide insertion forward oligo primer

<400> SEQUENCE: 103
gccgaagcgt ctacccgtcg taacctggca cgccgtggtg atcgcagcga ccgtaaccgt    60
acttacaact tcccg                                                     75

<210> SEQ ID NO 104
<211> LENGTH: 75
<212> TYPE: DNA
<213> ORGANISM: Artificial Sequence
<220> FEATURE:
<223> OTHER INFORMATION: synthetic No. 12 RF1 variant OmpT cleavage
      peptide insertion forward oligo primer

<400> SEQUENCE: 104
gccgaagcgt ctacccgtcg taacctgctg gcacgccgtg gtcgcagcga ccgtaaccgt    60
acttacaact tcccg                                                     75

<210> SEQ ID NO 105
<211> LENGTH: 75
<212> TYPE: DNA
<213> ORGANISM: Artificial Sequence
<220> FEATURE:
<223> OTHER INFORMATION: synthetic No. 13 RF1 variant OmpT cleavage
      peptide insertion forward oligo primer

<400> SEQUENCE: 105
gccgaagcgt ctacccgtcg taacctgctg ggggcacgcc gtggtagcga ccgtaaccgt    60
acttacaact tcccg                                                     75

<210> SEQ ID NO 106
<211> LENGTH: 75
<212> TYPE: DNA
<213> ORGANISM: Artificial Sequence
<220> FEATURE:
<223> OTHER INFORMATION: synthetic No. 14 RF1 variant OmpT cleavage
      peptide insertion forward oligo primer

<400> SEQUENCE: 106
gccgaagcgt ctacccgtcg taacctgctg gggagtgcac gccgtggtga ccgtaaccgt    60
acttacaact tcccg                                                     75

<210> SEQ ID NO 107
<211> LENGTH: 75
<212> TYPE: DNA

```
<213> ORGANISM: Artificial Sequence
<220> FEATURE:
<223> OTHER INFORMATION: synthetic No. 15 RF1 variant OmpT cleavage
      peptide insertion forward oligo primer

<400> SEQUENCE: 107
gccgaagcgt ctacccgtcg taacctgctg gggagtggcg cacgccgtga ccgtaaccgt    60
acttacaact tcccg                                                     75

<210> SEQ ID NO 108
<211> LENGTH: 75
<212> TYPE: DNA
<213> ORGANISM: Artificial Sequence
<220> FEATURE:
<223> OTHER INFORMATION: synthetic No. 16 RF1 variant OmpT cleavage
      peptide insertion forward oligo primer

<400> SEQUENCE: 108
gccgaagcgt ctacccgtcg tcgtctgctg gggagtggcg atcgcagcga ccgtaaccgt    60
acttacaact tcccg                                                     75

<210> SEQ ID NO 109
<211> LENGTH: 75
<212> TYPE: DNA
<213> ORGANISM: Artificial Sequence
<220> FEATURE:
<223> OTHER INFORMATION: synthetic No. 17 RF1 variant OmpT cleavage
      peptide insertion forward oligo primer

<400> SEQUENCE: 109
gcctggctgg cagcgcgtcg cggtcgtggc gggagtggcg atcgcagcga ccgtaaccgt    60
acttacaact tcccg                                                     75

<210> SEQ ID NO 110
<211> LENGTH: 75
<212> TYPE: DNA
<213> ORGANISM: Artificial Sequence
<220> FEATURE:
<223> OTHER INFORMATION: synthetic No. 18 RF1 variant OmpT cleavage
      peptide insertion forward oligo primer

<400> SEQUENCE: 110
gccgaatggc tggcagcgcg tcgcggtcgt ggcagtggcg atcgcagcga ccgtaaccgt    60
acttacaact tcccg                                                     75

<210> SEQ ID NO 111
<211> LENGTH: 75
<212> TYPE: DNA
<213> ORGANISM: Artificial Sequence
<220> FEATURE:
<223> OTHER INFORMATION: synthetic No. 19 RF1 variant OmpT cleavage
      peptide insertion forward oligo primer

<400> SEQUENCE: 111
gccgaagcgt ggctggcagc gcgtcgcggt cgtggcggcg atcgcagcga ccgtaaccgt    60
acttacaact tcccg                                                     75

<210> SEQ ID NO 112
<211> LENGTH: 75
<212> TYPE: DNA
<213> ORGANISM: Artificial Sequence
<220> FEATURE:
<223> OTHER INFORMATION: synthetic No. 20 RF1 variant OmpT cleavage
      peptide insertion forward oligo primer
```

<400> SEQUENCE: 112
tggggtggcc gttgggctcg caagaaaggt actattggcg atcgcagcga ccgtaaccgt    60
acttacaact tcccg                                                    75

<210> SEQ ID NO 113
<211> LENGTH: 75
<212> TYPE: DNA
<213> ORGANISM: Artificial Sequence
<220> FEATURE:
<223> OTHER INFORMATION: synthetic No. 21 RF1 variant OmpT cleavage
      peptide insertion forward oligo primer

<400> SEQUENCE: 113
gcctggggtg gccgttgggc tcgcaagaaa ggtactattg atcgcagcga ccgtaaccgt    60
acttacaact tcccg                                                    75

<210> SEQ ID NO 114
<211> LENGTH: 75
<212> TYPE: DNA
<213> ORGANISM: Artificial Sequence
<220> FEATURE:
<223> OTHER INFORMATION: synthetic No. 22 RF1 variant OmpT cleavage
      peptide insertion forward oligo primer

<400> SEQUENCE: 114
gccgaatggg gtggccgttg ggctcgcaag aaaggtacta ttcgcagcga ccgtaaccgt    60
acttacaact tcccg                                                    75

<210> SEQ ID NO 115
<211> LENGTH: 75
<212> TYPE: DNA
<213> ORGANISM: Artificial Sequence
<220> FEATURE:
<223> OTHER INFORMATION: synthetic No. 0 RF1 variant OmpT cleavage
      peptide insertion reverse oligo primer

<400> SEQUENCE: 115
gctgcgatcg ccactcccca gcaggttacg acgggtagac gcttcggcct gttggcgttt    60
tgccatttca gcagc                                                    75

<210> SEQ ID NO 116
<211> LENGTH: 75
<212> TYPE: DNA
<213> ORGANISM: Artificial Sequence
<220> FEATURE:
<223> OTHER INFORMATION: synthetic No. 1 RF1 variant OmpT cleavage
      peptide insertion reverse oligo primer

<400> SEQUENCE: 116
gctgcgatcg ccactcccca gcaggttacg acgggtagaa ccacggcgtg cttggcgttt    60
tgccatttca gcagc                                                    75

<210> SEQ ID NO 117
<211> LENGTH: 75
<212> TYPE: DNA
<213> ORGANISM: Artificial Sequence
<220> FEATURE:
<223> OTHER INFORMATION: synthetic No. 2 RF1 variant OmpT cleavage
      peptide insertion reverse oligo primer

<400> SEQUENCE: 117
gctgcgatcg ccactcccca gcaggttacg acgggtacca cggcgtgcct gttggcgttt    60
tgccatttca gcagc                                                          75

<210> SEQ ID NO 118
<211> LENGTH: 75
<212> TYPE: DNA
<213> ORGANISM: Artificial Sequence
<220> FEATURE:
<223> OTHER INFORMATION: synthetic No. 3 RF1 variant OmpT cleavage
      peptide insertion reverse oligo primer

<400> SEQUENCE: 118
gctgcgatcg ccactcccca gcaggttacg acgaccacgg cgtgcggcct gttggcgttt    60
tgccatttca gcagc                                                          75

<210> SEQ ID NO 119
<211> LENGTH: 75
<212> TYPE: DNA
<213> ORGANISM: Artificial Sequence
<220> FEATURE:
<223> OTHER INFORMATION: synthetic No. 4 RF1 variant OmpT cleavage
      peptide insertion reverse oligo primer

<400> SEQUENCE: 119
gctgcgatcg ccactcccca gcaggttacg accacggcgt gcttcggcct gttggcgttt    60
tgccatttca gcagc                                                          75

<210> SEQ ID NO 120
<211> LENGTH: 75
<212> TYPE: DNA
<213> ORGANISM: Artificial Sequence
<220> FEATURE:
<223> OTHER INFORMATION: synthetic No. 5 RF1 variant OmpT cleavage
      peptide insertion reverse oligo primer

<400> SEQUENCE: 120
gctgcgatcg ccactcccca gcaggttacc acggcgtgcc gcttcggcct gttggcgttt    60
tgccatttca gcagc                                                          75

<210> SEQ ID NO 121
<211> LENGTH: 75
<212> TYPE: DNA
<213> ORGANISM: Artificial Sequence
<220> FEATURE:
<223> OTHER INFORMATION: synthetic No. 6 RF1 variant OmpT cleavage
      peptide insertion reverse oligo primer

<400> SEQUENCE: 121
gctgcgatcg ccactcccca gcagaccacg gcgtgcagac gcttcggcct gttggcgttt    60
tgccatttca gcagc                                                          75

<210> SEQ ID NO 122
<211> LENGTH: 75
<212> TYPE: DNA
<213> ORGANISM: Artificial Sequence
<220> FEATURE:
<223> OTHER INFORMATION: synthetic No. 7 RF1 variant OmpT cleavage
      peptide insertion reverse oligo primer

<400> SEQUENCE: 122
gctgcgatcg ccactcccca gaccacggcg tgcggtagac gcttcggcct gttggcgttt    60
tgccatttca gcagc                                                          75

-continued

<210> SEQ ID NO 123
<211> LENGTH: 75
<212> TYPE: DNA
<213> ORGANISM: Artificial Sequence
<220> FEATURE:
<223> OTHER INFORMATION: synthetic No. 8 RF1 variant OmpT cleavage
      peptide insertion reverse oligo primer

<400> SEQUENCE: 123
gctgcgatcg ccactcccac cacggcgtgc acgggtagac gcttcggcct gttggcgttt    60
tgccatttca gcagc                                                     75

<210> SEQ ID NO 124
<211> LENGTH: 75
<212> TYPE: DNA
<213> ORGANISM: Artificial Sequence
<220> FEATURE:
<223> OTHER INFORMATION: synthetic No. 9 RF1 variant OmpT cleavage
      peptide insertion reverse oligo primer

<400> SEQUENCE: 124
gctgcgatcg ccactaccac ggcgtgcacg acgggtagac gcttcggcct gttggcgttt    60
tgccatttca gcagc                                                     75

<210> SEQ ID NO 125
<211> LENGTH: 75
<212> TYPE: DNA
<213> ORGANISM: Artificial Sequence
<220> FEATURE:
<223> OTHER INFORMATION: synthetic No. 10 RF1 variant OmpT cleavage
      peptide insertion reverse oligo primer

<400> SEQUENCE: 125
gctgcgatcg ccaccacggc gtgcgttacg acgggtagac gcttcggcct gttggcgttt    60
tgccatttca gcagc                                                     75

<210> SEQ ID NO 126
<211> LENGTH: 75
<212> TYPE: DNA
<213> ORGANISM: Artificial Sequence
<220> FEATURE:
<223> OTHER INFORMATION: synthetic No. 11 RF1 variant OmpT cleavage
      peptide insertion reverse oligo primer

<400> SEQUENCE: 126
gctgcgatca ccacggcgtg ccaggttacg acgggtagac gcttcggcct gttggcgttt    60
tgccatttca gcagc                                                     75

<210> SEQ ID NO 127
<211> LENGTH: 75
<212> TYPE: DNA
<213> ORGANISM: Artificial Sequence
<220> FEATURE:
<223> OTHER INFORMATION: synthetic No. 12 RF1 variant OmpT cleavage
      peptide insertion reverse oligo primer

<400> SEQUENCE: 127
gctgcgacca cggcgtgcca gcaggttacg acgggtagac gcttcggcct gttggcgttt    60
tgccatttca gcagc                                                     75

<210> SEQ ID NO 128
<211> LENGTH: 75
<212> TYPE: DNA
<213> ORGANISM: Artificial Sequence
<220> FEATURE:
<223> OTHER INFORMATION: synthetic No. 13 RF1 variant OmpT cleavage
      peptide insertion reverse oligo primer

<400> SEQUENCE: 128
gctaccacgg cgtgccccca gcaggttacg acgggtagac gcttcggcct gttggcgttt     60
tgccatttca gcagc     75

<210> SEQ ID NO 129
<211> LENGTH: 75
<212> TYPE: DNA
<213> ORGANISM: Artificial Sequence
<220> FEATURE:
<223> OTHER INFORMATION: synthetic No. 14 RF1 variant OmpT cleavage
      peptide insertion reverse oligo primer

<400> SEQUENCE: 129
accacggcgt gcactcccca gcaggttacg acgggtagac gcttcggcct gttggcgttt     60
tgccatttca gcagc     75

<210> SEQ ID NO 130
<211> LENGTH: 75
<212> TYPE: DNA
<213> ORGANISM: Artificial Sequence
<220> FEATURE:
<223> OTHER INFORMATION: synthetic No. 15 RF1 variant OmpT cleavage
      peptide insertion reverse oligo primer

<400> SEQUENCE: 130
acggcgtgcg ccactcccca gcaggttacg acgggtagac gcttcggcct gttggcgttt     60
tgccatttca gcagc     75

<210> SEQ ID NO 131
<211> LENGTH: 75
<212> TYPE: DNA
<213> ORGANISM: Artificial Sequence
<220> FEATURE:
<223> OTHER INFORMATION: synthetic No. 16 RF1 variant OmpT cleavage
      peptide insertion reverse oligo primer

<400> SEQUENCE: 131
gctgcgatcg ccactcccca gcagacgacg acgggtagac gcttcggcct gttggcgttt     60
tgccatttca gcagc     75

<210> SEQ ID NO 132
<211> LENGTH: 75
<212> TYPE: DNA
<213> ORGANISM: Artificial Sequence
<220> FEATURE:
<223> OTHER INFORMATION: synthetic No. 17 RF1 variant OmpT cleavage
      peptide insertion reverse oligo primer

<400> SEQUENCE: 132
gctgcgatcg ccactcccgc cacgaccgcg acgcgctgcc agccaggcct gttggcgttt     60
tgccatttca gcagc     75

<210> SEQ ID NO 133
<211> LENGTH: 75
<212> TYPE: DNA
<213> ORGANISM: Artificial Sequence
<220> FEATURE:
<223> OTHER INFORMATION: synthetic No. 18 RF1 variant OmpT cleavage
      peptide insertion reverse oligo primer

<400> SEQUENCE: 133
gctgcgatcg ccactgccac gaccgcgacg cgctgccagc cattcggcct gttggcgttt    60
tgccatttca gcagc                                                    75

<210> SEQ ID NO 134
<211> LENGTH: 75
<212> TYPE: DNA
<213> ORGANISM: Artificial Sequence
<220> FEATURE:
<223> OTHER INFORMATION: synthetic No. 19 RF1 variant OmpT cleavage
      peptide insertion reverse oligo primer

<400> SEQUENCE: 134
gctgcgatcg ccgccacgac cgcgacgcgc tgccagccac gcttcggcct gttggcgttt    60
tgccatttca gcagc                                                    75

<210> SEQ ID NO 135
<211> LENGTH: 75
<212> TYPE: DNA
<213> ORGANISM: Artificial Sequence
<220> FEATURE:
<223> OTHER INFORMATION: synthetic No. 20 RF1 variant OmpT cleavage
      peptide insertion reverse oligo primer

<400> SEQUENCE: 135
gctgcgatcg ccaatagtac ctttcttgcg agcccaacgg ccaccccact gttggcgttt    60
tgccatttca gcagc                                                    75

<210> SEQ ID NO 136
<211> LENGTH: 75
<212> TYPE: DNA
<213> ORGANISM: Artificial Sequence
<220> FEATURE:
<223> OTHER INFORMATION: synthetic No. 21 RF1 variant OmpT cleavage
      peptide insertion reverse oligo primer

<400> SEQUENCE: 136
gctgcgatca atagtaccttt tcttgcgagc ccaacggcca ccccaggcct gttggcgttt    60
tgccatttca gcagc                                                    75

<210> SEQ ID NO 137
<211> LENGTH: 75
<212> TYPE: DNA
<213> ORGANISM: Artificial Sequence
<220> FEATURE:
<223> OTHER INFORMATION: synthetic No. 22 RF1 variant OmpT cleavage
      peptide insertion reverse oligo primer

<400> SEQUENCE: 137
gctgcgaata gtacctttct tgcgagccca acggccaccc cattcggcct gttggcgttt    60
tgccatttca gcagc                                                    75

<210> SEQ ID NO 138
<211> LENGTH: 66
<212> TYPE: DNA
<213> ORGANISM: Artificial Sequence
<220> FEATURE:
<223> OTHER INFORMATION: synthetic RF1 amplification primer 5His-RF1

<400> SEQUENCE: 138
catatgcatc accatcacca tcacggtggt ggctctaagc ttctatcgt tgccaaactg    60 gaagcc                                                              66

<210> SEQ ID NO 139
<211> LENGTH: 33
<212> TYPE: DNA
<213> ORGANISM: Artificial Sequence
<220> FEATURE:
<223> OTHER INFORMATION: synthetic RF1 amplification primer 3RF1

<400> SEQUENCE: 139
gtcgacttat tcctgctcgg acaacgccgc cag                              33

<210> SEQ ID NO 140
<211> LENGTH: 90
<212> TYPE: DNA
<213> ORGANISM: Artificial Sequence
<220> FEATURE:
<223> OTHER INFORMATION: synthetic Oligonucleotide-Mediated Allelic
      Replacement (OMAR) PCR oligo 1opRF1 KR

<400> SEQUENCE: 140
gggaagttgt aagtacggtt acggtcgctg cgatcccctg aaccaagacg ctttcgacgg    60
gtagacgctt cggcctgttg gcgttttgcc                                    90

<210> SEQ ID NO 141
<211> LENGTH: 90
<212> TYPE: DNA
<213> ORGANISM: Artificial Sequence
<220> FEATURE:
<223> OTHER INFORMATION: synthetic Oligonucleotide-Mediated Allelic
      Replacement (OMAR) PCR oligo 1opRF1 KRR

<400> SEQUENCE: 141
gggaagttgt aagtacggtt acggtcgctg cgatcccctg aaccacgacg ctttcgacgg    60
gtagacgctt cggcctgttg gcgttttgcc                                    90

<210> SEQ ID NO 142
<211> LENGTH: 90
<212> TYPE: DNA
<213> ORGANISM: Artificial Sequence
<220> FEATURE:
<223> OTHER INFORMATION: synthetic Oligonucleotide-Mediated Allelic
      Replacement (OMAR) PCR oligo 1opRF1 KRK

<400> SEQUENCE: 142
gggaagttgt aagtacggtt acggtcgctg cgatcccctg aaccCttacg ctttcgacgg    60
gtagacgctt cggcctgttg gcgttttgcc                                    90

<210> SEQ ID NO 143
<211> LENGTH: 22
<212> TYPE: DNA
<213> ORGANISM: Artificial Sequence
<220> FEATURE:
<223> OTHER INFORMATION: synthetic Mismatch Amplification Mutation Assay
      (MAMA) PCR oligo 3KR op-PCR

<400> SEQUENCE: 143
gcgatcccct gaaccaagac gc                                            22

<210> SEQ ID NO 144
<211> LENGTH: 21
<212> TYPE: DNA
<213> ORGANISM: Artificial Sequence
<220> FEATURE:
<223> OTHER INFORMATION: synthetic Mismatch Amplification Mutation Assay
      (MAMA) PCR oligo 3 KRR op-PCR

<400> SEQUENCE: 144 cgatccctg aaccacgacg c                                          21

<210> SEQ ID NO 145
<211> LENGTH: 23
<212> TYPE: DNA
<213> ORGANISM: Artificial Sequence
<220> FEATURE:
<223> OTHER INFORMATION: synthetic Mismatch Amplification Mutation Assay
      (MAMA) PCR oligo 3KRK op-PCR

<400> SEQUENCE: 145
tgcgatcccc tgaaccctta cgc                                       23

<210> SEQ ID NO 146
<211> LENGTH: 22
<212> TYPE: DNA
<213> ORGANISM: Artificial Sequence
<220> FEATURE:
<223> OTHER INFORMATION: synthetic Mismatch Amplification Mutation Assay
      (MAMA) PCR oligo 5 RF1 op-PCR

<400> SEQUENCE: 146
cgtgacgggg ataacgaacg cc                                        22

<210> SEQ ID NO 147
<211> LENGTH: 19
<212> TYPE: DNA
<213> ORGANISM: Artificial Sequence
<220> FEATURE:
<223> OTHER INFORMATION: synthetic rolling circle amplification and
      primer extension sequencing primer T7

<400> SEQUENCE: 147
taatacgact cactatagg                                            19

<210> SEQ ID NO 148
<211> LENGTH: 18
<212> TYPE: DNA
<213> ORGANISM: Artificial Sequence
<220> FEATURE:
<223> OTHER INFORMATION: synthetic rolling circle amplification and
      primer extension sequencing primer T7 term

<400> SEQUENCE: 148
gctagttatt gctcagcg                                             18

<210> SEQ ID NO 149
<211> LENGTH: 39
<212> TYPE: DNA
<213> ORGANISM: Artificial Sequence
<220> FEATURE:
<223> OTHER INFORMATION: synthetic site directed mutagenesis variant
      SP-00067_V422 sense oligo primer for introducing
      amber codon in Herceptin

<400> SEQUENCE: 149
cgttggcagc agggtaatta gttcagctgc agcgttatg                      39

<210> SEQ ID NO 150
<211> LENGTH: 39
<212> TYPE: DNA
<213> ORGANISM: Artificial Sequence
<220> FEATURE:
<223> OTHER INFORMATION: synthetic site directed mutagenesis variant
      SP-00067_V422 antisense oligo primer for introducing amber codon in Herceptin

<400> SEQUENCE: 150
cataacgctg cagctgaact aattaccctg ctgccaacg        39

<210> SEQ ID NO 151
<211> LENGTH: 42
<212> TYPE: DNA
<213> ORGANISM: Artificial Sequence
<220> FEATURE:
<223> OTHER INFORMATION: synthetic site directed mutagenesis variant
     SP-00127_S415 sense oligo primer for introducing
     amber codon in Herceptin

<400> SEQUENCE: 151
gcaagctgac cgtcgataaa tagcgttggc agcagggtaa tg        42

<210> SEQ ID NO 152
<211> LENGTH: 42
<212> TYPE: DNA
<213> ORGANISM: Artificial Sequence
<220> FEATURE:
<223> OTHER INFORMATION: synthetic site directed mutagenesis variant
     SP-00127_S415 antisense oligo primer for
     introducing amber codon in Herceptin

<400> SEQUENCE: 152
cattaccctg ctgccaacgc tatttatcga cggtcagctt gc        42

<210> SEQ ID NO 153
<211> LENGTH: 36
<212> TYPE: DNA
<213> ORGANISM: Artificial Sequence
<220> FEATURE:
<223> OTHER INFORMATION: synthetic site directed mutagenesis variant
     SP-00128_Q418 sense oligo primer for introducing
     amber codon in Herceptin

<400> SEQUENCE: 153
cgataaaagc cgttggtagc agggtaatgt gttcag        36

<210> SEQ ID NO 154
<211> LENGTH: 36
<212> TYPE: DNA
<213> ORGANISM: Artificial Sequence
<220> FEATURE:
<223> OTHER INFORMATION: synthetic site directed mutagenesis variant
     SP-00128_Q418 antisense oligo primer for
     introducing amber codon in Herceptin

<400> SEQUENCE: 154
ctgaacacat taccctgcta ccaacggctt ttatcg        36

<210> SEQ ID NO 155
<211> LENGTH: 35
<212> TYPE: DNA
<213> ORGANISM: Artificial Sequence
<220> FEATURE:
<223> OTHER INFORMATION: synthetic site directed mutagenesis variant
     SP-00114_P343 sense oligo primer for introducing
     amber codon in Herceptin

<400> SEQUENCE: 155
gcaaagcgaa aggccaatag cgtgaaccgc aggtc        35

<210> SEQ ID NO 156
<211> LENGTH: 35

<210> SEQ ID NO 156
<211> LENGTH: 35
<212> TYPE: DNA
<213> ORGANISM: Artificial Sequence
<220> FEATURE:
<223> OTHER INFORMATION: synthetic site directed mutagenesis variant
SP-00114_P343 antisense oligo primer for
introducing amber codon in Herceptin

<400> SEQUENCE: 156
gacctgcggt tcacgctatt ggcctttcgc tttgc          35

<210> SEQ ID NO 157
<211> LENGTH: 40
<212> TYPE: DNA
<213> ORGANISM: Artificial Sequence
<220> FEATURE:
<223> OTHER INFORMATION: synthetic site directed mutagenesis variant
SP-00112_G341 sense oligo primer for introducing
amber codon in Herceptin

<400> SEQUENCE: 157
gacgatcagc aaagcgaaat agcaaccgcg tgaaccgcag          40

<210> SEQ ID NO 158
<211> LENGTH: 40
<212> TYPE: DNA
<213> ORGANISM: Artificial Sequence
<220> FEATURE:
<223> OTHER INFORMATION: synthetic site directed mutagenesis variant
SP-00112_G341 antisense oligo primer for
introducing amber codon in Herceptin

<400> SEQUENCE: 158
ctgcggttca cgcggttgct atttcgcttt gctgatcgtc          40

<210> SEQ ID NO 159
<211> LENGTH: 41
<212> TYPE: DNA
<213> ORGANISM: Artificial Sequence
<220> FEATURE:
<223> OTHER INFORMATION: synthetic site directed mutagenesis variant
SP-00102_K320 sense oligo primer for introducing
amber codon in Herceptin

<400> SEQUENCE: 159
gctgaatggt aaagaatact agtgcaaagt gagcaacaag g          41

<210> SEQ ID NO 160
<211> LENGTH: 41
<212> TYPE: DNA
<213> ORGANISM: Artificial Sequence
<220> FEATURE:
<223> OTHER INFORMATION: synthetic site directed mutagenesis variant
SP-00102_K320 antisense oligo primer for
introducing amber codon in Herceptin

<400> SEQUENCE: 160
ccttgttgct cactttgcac tagtattctt taccattcag c          41

<210> SEQ ID NO 161
<211> LENGTH: 39
<212> TYPE: DNA
<213> ORGANISM: Artificial Sequence
<220> FEATURE:
<223> OTHER INFORMATION: synthetic site directed mutagenesis variant
SP-00066_F404 sense oligo primer for introducing
amber codon in Herceptin

<400> SEQUENCE: 161
ctggacagcg acggtagcta gtttctgtat agcaagctg            39

<210> SEQ ID NO 162
<211> LENGTH: 39
<212> TYPE: DNA
<213> ORGANISM: Artificial Sequence
<220> FEATURE:
<223> OTHER INFORMATION: synthetic site directed mutagenesis variant
    SP-00066_F404 antisense oligo primer for
    introducing amber codon in Herceptin

<400> SEQUENCE: 162
cagcttgcta tacagaaact agctaccgtc gctgtccag            39

<210> SEQ ID NO 163
<211> LENGTH: 32
<212> TYPE: DNA
<213> ORGANISM: Artificial Sequence
<220> FEATURE:
<223> OTHER INFORMATION: synthetic site directed mutagenesis variant
    SP-00113_Q342 sense oligo primer for introducing
    amber codon in Herceptin

<400> SEQUENCE: 163
gcaaagcgaa aggctagccg cgtgaaccgc ag                   32

<210> SEQ ID NO 164
<211> LENGTH: 32
<212> TYPE: DNA
<213> ORGANISM: Artificial Sequence
<220> FEATURE:
<223> OTHER INFORMATION: synthetic site directed mutagenesis variant
    SP-00113_Q342 antisense oligo primer for
    introducing amber codon in Herceptin

<400> SEQUENCE: 164
ctgcggttca cgcggctagc ctttcgcttt gc                   32

<210> SEQ ID NO 165
<211> LENGTH: 42
<212> TYPE: DNA
<213> ORGANISM: Artificial Sequence
<220> FEATURE:
<223> OTHER INFORMATION: synthetic site directed mutagenesis variant
    SP-00096_T299 sense oligo primer for introducing
    amber codon in Herceptin

<400> SEQUENCE: 165
gtgaggaaca atacaatagc tagtatcgcg tagtgagcgt gc        42

<210> SEQ ID NO 166
<211> LENGTH: 42
<212> TYPE: DNA
<213> ORGANISM: Artificial Sequence
<220> FEATURE:
<223> OTHER INFORMATION: synthetic site directed mutagenesis variant
    SP-00096_T299 antisense oligo primer for
    introducing amber codon in Herceptin

<400> SEQUENCE: 166
gcacgctcac tacgcgatac tagctattgt attgttcctc ac        42

<210> SEQ ID NO 167
<211> LENGTH: 30
<212> TYPE: DNA
<213> ORGANISM: Artificial Sequence
<220> FEATURE:
<223> OTHER INFORMATION: synthetic site directed mutagenesis variant SP-00120_Y373 sense oligo primer for introducing
amber codon in Herceptin

<400> SEQUENCE: 167
ggtgaagggc ttttagccga gcgacatcgc                                           30

<210> SEQ ID NO 168
<211> LENGTH: 30
<212> TYPE: DNA
<213> ORGANISM: Artificial Sequence
<220> FEATURE:
<223> OTHER INFORMATION: synthetic site directed mutagenesis variant
      SP-00120_Y373 antisense oligo primer for
      introducing amber codon in Herceptin

<400> SEQUENCE: 168
gcgatgtcgc tcggctaaaa gcccttcacc                                           30

<210> SEQ ID NO 169
<211> LENGTH: 38
<212> TYPE: DNA
<213> ORGANISM: Artificial Sequence
<220> FEATURE:
<223> OTHER INFORMATION: synthetic site directed mutagenesis variant
      SP-00094_N297 sense oligo primer for introducing
      amber codon in Herceptin

<400> SEQUENCE: 169
cgcgtgagga acaatactag agcacgtatc gcgtagtg                                  38

<210> SEQ ID NO 170
<211> LENGTH: 38
<212> TYPE: DNA
<213> ORGANISM: Artificial Sequence
<220> FEATURE:
<223> OTHER INFORMATION: synthetic site directed mutagenesis variant
      SP-00094_N297 antisense oligo primer for
      introducing amber codon in Herceptin

<400> SEQUENCE: 170
cactacgcga tacgtgctct agtattgttc ctcacgcg                                  38

<210> SEQ ID NO 171
<211> LENGTH: 38
<212> TYPE: DNA
<213> ORGANISM: Artificial Sequence
<220> FEATURE:
<223> OTHER INFORMATION: synthetic site directed mutagenesis variant
      SP-00125_F405 sense oligo primer for introducing
      amber codon in Herceptin

<400> SEQUENCE: 171
gacagcgacg gtagcttcta gctgtatagc aagctgac                                  38

<210> SEQ ID NO 172
<211> LENGTH: 38
<212> TYPE: DNA
<213> ORGANISM: Artificial Sequence
<220> FEATURE:
<223> OTHER INFORMATION: synthetic site directed mutagenesis variant
      SP-00125_F405 antisense oligo primer for
      introducing amber codon in Herceptin

<400> SEQUENCE: 172
gtcagcttgc tatacagcta gaagctaccg tcgctgtc                                  38

What is claimed is:

1. A mutant Releasing Factor 1 (RF1) protein, wherein the mutant RF1 protein comprises an amino acid sequence having at least 95% sequence identity to the amino acid sequence of SEQ ID NO: 1, wherein the mutant RF1 protein has activity to recognize a stop codon in an mRNA sequence and terminate translation, wherein the amino acid sequence of the mutant RF1 protein corresponding to amino acids 287-304 of SEQ ID NO: 1 comprises a cleavage site for a wild-type Outer Membrane Protein T1 (OmpT1), wherein the amino acid sequence of the cleavage site for the wild-type OmpT1 comprises an amino acid sequence selected from the group consisting of ARR, ARRG (SEQ ID NO:47), WLAARRGRG (SEQ ID NO:48), and WGGRWARKKGTI (SEQ ID NO:49).

2. The mutant RF1 protein of claim 1, wherein the amino acid sequence of the cleavage site for the wild-type OmpT1 comprises an amino acid sequence selected from the group consisting of:
QARRGSTRRNLLGSGDRS (SEQ ID NO:26);
QQARRGTRRNLLGSGDRS (SEQ ID NO:27);
QQAARRGRRNLLGSGDRS (SEQ ID NO:28);
QQAEARRGRNLLGSGDRS (SEQ ID NO:29);
QQAEAARRGNLLGSGDRS (SEQ ID NO:30);
QQAEASARRGLLGSGDRS (SEQ ID NO:31);
QQAEASTARRGLGSGDRS (SEQ ID NO:32);
QQAEASTRRARRGSGDRS (SEQ ID NO:34);
QQAEASTRRNARRGGDRS (SEQ ID NO:35);
QQAEASTRRNLARRGDRS (SEQ ID NO:36);
QQAEASTRRNLLARRGRS (SEQ ID NO:37);
QQAEASTRRNLLGARRGS (SEQ ID NO:38);
QQAEASTRRNLLGSARRG (SEQ ID NO:39);
QQAEASTRRNLLGSGARR (SEQ ID NO:40)
QQAWLAARRGRGGSGDRS (SEQ ID NO:41);
QQAEWLAARRGRGSGDRS (SEQ ID NO:42);
QQAEAWLAARRGRGGDRS (SEQ ID NO:43)
QQWGGRWARKKGTIGDRS (SEQ ID NO:44);
QQAWGGRWARKKGTIDRS (SEQ ID NO:45); and
QQAEWGGRWARKKGTIRS (SEQ ID NO:46).

3. A bacterial cell comprising both an OmpT1 and the mutant RF1 protein of claim 1.

4. A nucleic acid encoding the mutant RF1 protein of claim 1.

5. A bacterial cell comprising the nucleic acid of claim 4, wherein the nucleic acid is incorporated into a genome of the bacterial cell.

6. A bacterial cell extract comprising the mutant RF1 protein of claim 1.

7. A cell free synthesis system comprising in a single reaction mixture:
i) components from a bacterial lysate sufficient to translate a nucleic acid template encoding a protein;
ii) a nucleic acid template encoding a protein of interest and having at least one amber codon;
iii) tRNA complementary to the amber codon; and,
iv) the mutant RF1 protein of claim 1.

8. The cell free synthesis system of claim 7, wherein the single reaction mixture further comprises a non-natural amino acid and corresponding amino acid tRNA synthetase, the tRNA synthetase able to charge the tRNA complimentary to the amber codon with the non-natural amino acid.

9. The cell free synthesis system of claim 8, wherein the system generates ATP via an active oxidative phosphorylation system.

10. The mutant RF1 protein of claim 1, wherein the wild-type OmpT1 comprises the amino acid sequence of SEQ ID NO: 3.

11. A method for expressing a protein of interest in a bacterial cell-free synthesis system, comprising:
i. combining a nucleic acid template encoding the protein of interest with a bacterial cell free synthesis extract to produce a bacterial cell-free synthesis system, wherein the bacterial cell free synthesis extract comprises the mutant RF1 protein of claim 1 and a wild-type OmpT1;
ii. allowing the mutant RF1 protein to be cleaved by the wild-type OmpT1; and
iii. expressing the protein of interest from the nucleic acid template.

12. A method for preparing a cell free synthesis extract, the method comprising the steps of:
i) culturing OmpT1 positive bacteria comprising the nucleic acid of claim 4 to express the mutant RF1 protein; and
ii) lysing the OmpT1 positive bacteria to create the cell free synthesis extract.

13. The method of claim 12, wherein the OmpT1 positive bacteria is *Escherichia coli*.

* * * * *